US009682157B2

(12) United States Patent
Gao et al.

(10) Patent No.: US 9,682,157 B2
(45) Date of Patent: Jun. 20, 2017

(54) PH-SENSITIVE IMAGING AGENTS

(71) Applicant: Board of Trustees of Southern Illinois University, Carbondale, IL (US)

(72) Inventors: Yong Gao, Carbondale, IL (US); Boyd Goodson, Carbondale, IL (US)

(73) Assignee: BOARD OF TRUSTEES OF SOUTHERN ILLINOIS UNIVERSITY, Carbondale, IL (US)

( * ) Notice: Subject to any disclaimer, the term of this patent is extended or adjusted under 35 U.S.C. 154(b) by 454 days.

(21) Appl. No.: 14/072,637

(22) Filed: Nov. 5, 2013

(65) Prior Publication Data
US 2014/0127138 A1 May 8, 2014

Related U.S. Application Data

(60) Provisional application No. 61/722,631, filed on Nov. 5, 2012.

(51) Int. Cl.
A61K 49/18 (2006.01)
(52) U.S. Cl.
CPC ........ *A61K 49/1872* (2013.01); *A61K 49/186* (2013.01); *A61K 49/1857* (2013.01)
(58) Field of Classification Search
None
See application file for complete search history.

(56) References Cited

PUBLICATIONS

Zhou et al. Synthesis, characterization, and controllable drug release of pH-sensitive hybrid magnetic nanoparticles. 2009 J. Magn. Magn. Mater. 321: 2799-2804.*
Branca et al. Molecular MRI for sensitive and specific detection of lung metastases. 2010 Proc. Natl. Acad. Sci. USA 107: 3693-3697.*
Chertok et al. Iron oxide nanoparticles as a drug delivery vehicle for MRI monitored magnetic targeting of brain tumors. 2008 Biomaterials 29: 487-496.*
Chang et al. Novel water-soluble and pH-responsive anticancer drug nanocarriers: doxorubicin-PAMAM dendrimer conjugates attached to superparamagnetic iron oxide nanoparticles (IONPs). 2011 J. Colloid Interface Sci. 363: 403-409. Published online Jul. 23, 2011.*
Yang et al. Fabrication of biocompatible temperature- and pH-responsive magnetic nanoparticles and their reversible agglomeration in aqueous milieu. 2010 Ind. Eng. Chem. Res. 49: 8518-8525.*
Ge et al. Superparamagnetic magnetite colloidal nanocrystal clusters. 2007 Angew. Chem. Int. Ed. Engl. 46: 4342-4345.*
Aime et al. A macromolecular Gd(III) complex as pH-responsive relaxometric probe for MRI applications. 1999 Chem. Commun. 1577-1578.*
Morgan et al. Biochemical characterisation of polycation-induced cytotoxicity to human vascular endothelial cells. 1989 J. Cell Sci. 94: 553-559.*

Ali MM et al. Synthesis and Relaxometric Studies of a Dendrimer-Based pH-Responsive MRI Contrast Agent. Chemistry: A European Journal, 2008, vol. 14, pp. 7250-7258.
Atanasijevic T et al. Calcium-Sensitive MRI Contrast Agents Based on Superparamagnetic Iron Oxide Nanoparticles and Calmodulin. Proceedings of the National Academy of Sciences of the United States of America, 2006, vol. 103, pp. 14707-14712.
Beauregard DA et al. Relaxation-Based Mapping of Tumour pH. Proceedings of the International Society for Magnetic Resonance in Medicine, 1998, vol. 6, p. 53.
Belhoussine R et al. Characeterization of Intracellular pH Gradients in Human Multidrug-Resistant Tumor Cells by Means of Scanning Microspectrofluorometry and Dual-Emission-Ratio Probes. International Journal of Cancer, 1999, vol. 81, pp. 81-89.
Bjornerud A et al. Assessment of $T_1$ and $T_2$ Effects In Vivo and Ex Vivo Using Iron Oxide Nanoaprticles in Steady State-Dependence on Blood Volume and Water Exchange. Magnetic Resonance in Medicine, 2002, vol. 47, pp. 461-471.
Bowen CV et al. Application of the Statis Dephasing Regime Theory to Superparamagnetic Iron-Oxide Loaded Cells. Magnetic Resonance in Medicine, 2002, vol. 48, pp. 52-61.
Brooks RA et al. On $T_2$-Shortening by Weakly Magnetized Particles: The Chemical Exchange Model. Magnetic Resonance in Medicine, 2001, vol. 45, pp. 1014-1020.
Bulte JWM et al. Relaxometry and Magnetometry of the MR Contrast Agent MION-46L. Magnetic Resonance in Medicine, 1999, vol. 42, pp. 379-384.
Bulte JWM et al. Magnetodendrimers Allow Endosomal Magnetic Labeling and In Vivo Tracking of Stem Cells. Nature Biotechnology, 2001, vol. 19, pp. 1141-1147.
Chaudhry M et al. Culture pH and Osmolality Influence Proliferation and Embryoid Body Yields of Murine Embryonic Stem Cells. Biochemical Engineering Journal, 2009, vol. 45, pp. 126-135.
Chen T et al. Targeted Folic Acid-PEG Nanoparticles for Noninvasive Imaging of Folate Receptor by MRI. Journal of Biomedical Materials Research Part A, 2008, vol. 87, pp. 165-175.
Dahnke H et al. Susceptibility Gradient Mapping (SG): A New Postprocessing Method for Positive Contrast Generation Applied to Superparamagnetic Iron Oxide Particle (SPOI)-Labeled Cells. Magnetic Resonance in Medicine, 2008, vol. 60, pp. 595-603.
Duanmu C et al. Dendron-Functionalized Superparamagnetic Nanoparticles with Switchable Solubility in Organic and Aqueous Media: Matrices for Homogeneous Catalysis and Potential MRI Contrast Agents. Chemistry of Materials, 2006, vol. 18, pp. 5973-5981.
Frank JA et al. Magnetic Intracellular Labeling of Mammalian Cells by Combining (FDA-Approved) Superparamagnetic Iron Oxide MR Contrast Agents and Commonly Used Transfection Agents. Academic Radiology, 2002, vol. 9, pp. S484-S487.
Frank JA et al. Clinically Applicable Labeling of Mammalian and Stem Cells by Combining Superparamagnetic Iron Oxides and Transfection Agents. Radiology, 2003, vol. 228, pp. 480-487.
Gao X et al. In Vivo Cancer Targeting and Imaging with Semiconductor Quantum Dots. Nature Biotechnology, 2004, vol. 22, pp. 969-976.
Gillies RJ et al. $^{31}$P-MRS Measurements of Extracellular pH of Tumors Using 3-Aminopropylphosphonate. The American Journal of Physiology, 1994, vol. 267, pp. C195-C203.
Gunn J et al. A simple and Highly Sensitive Method for Magnetic Nanoparticle Quantitation Using $^1$H-NMR Spectroscopy. Biophysical Journal, 2009, vol. 97, pp. 2640-2647.

(Continued)

Primary Examiner — Michael G Hartley
Assistant Examiner — Jennifer Lamberski
(74) Attorney, Agent, or Firm — Dentons US LLP

(57) ABSTRACT

Composition and method for surface-functionalized SPION-based agents. Such agents can provide highly pH-sensitive MRI contrast in tissue.

21 Claims, 24 Drawing Sheets

(56) References Cited

PUBLICATIONS

Hirt RC & Schmitt RG. Ultraviolet Absorption Spectra of Derivatives of Symmetric Triazine-II Oxo-Triazines and their Acyclic Analogs. Spectrochimica Acta, 1958, vol. 12, pp. 127-138.

Jensen JH & Chandra R. NMR Relaxation in Tissues with Weak Magnetic Inhomogeneities. Magnetic Resonance in Medicine, 2000, vol. 44, pp. 144-156.

Kalish H et al. Combination of Transfection Agents and Magnetic Resonance Contrast Agents for Cellular Imaging: Relationship Between Relaxivities, Electrostatic Forces, and Chemical Composition. Magnetic Resonance in Medicine, 2003, vol. 50, pp. 275-282.

Kalman FK et al. Potentiometric and Relaxometric Properties of a Gadolinium-Based MRI Contrast Agent for Sensing Tissue pH. Inorganic Chemistry, 2007, vol. 46, pp. 5260-5270.

Kievit FM et al. PEI-PEG-Chitosan Copolymer Coated Iron Oxide Nanoparticles for Safe Gene Delivery: Synthesis, Complexation, and Transfection. Advanced Functional Materials, 2009, vol. 19, pp. 2244-2251.

Kim M et al. Super-Stable, High-Quality $Fe_3O_4$ Dendron-Nanocrystals Dispersible in Both Organic and Aqueous Solutions. Advanced Materials, 2005, vol. 17, pp. 1429-1432.

Kneen M et al. Green Fluorescent Protein as a Noninvasive Intracellular pH Indicator. Biophysical Journal, 1998, vol. 74, pp. 1591-1599.

Kohler N et al. A Bifunctional Poly(ethylene glycol) Silane Immobilized on Metallic Oxide-Based Nanoparticles for Conjugation with Cell Targeting Agents. Journal of the American Chemical Society, 2004, vol. 126, pp. 7206-7211.

Laconte LE et al. Coating Thickness of Magnetic Iron Oxide Nanoparticles Affects R2 Relaxivity. Journal of Magnetic Resonance Imaging, 2007, vol. 26, pp. 1634-1641.

Lee H et al. Antibiofouling Polymer-Coated Superparamagnetic Iron Oxide nanoparticles as Potential Magnetic Resonance Contrast Agents for In Vivo Cancer Imaging. Journal of the American Chemical Society, 2006, vol. 128, pp. 7388-7389.

Lim J & Simanek EE. Toward the Next-Generation Drug Delivery Vehicle: Synthesis of a Dendrimer with Four Orthogonally Reactive Groups. Molecular Pharmaceutics, 2005, vol. 2, pp. 273-277.

Lu J et al. Synthesis of Alkyl Sulfonate/Alcohol-Protected $\gamma$-Fe2O3 Nanocrystals with Narrow Size Distributions. Journal of Colloid and Interface Science, 2003, vol. 258, pp. 427-431.

Lu Y et al. Modifying the Surface Properties of Superparamagnetic Iton Oxide Nanoparticles through a Sol-Gel Approach. Nano Letters, 2002, vol. 2, pp. 183-186.

Matsumoto Y & Jasanoff A. T2 Relaxation Induced by Clusters of Superparamagnetic Nanoparticles: Monte Carlo Simulations. Magnetic Resonance Imaging, 2008, vol. 26, pp. 994-998.

Paradiso AM et al. $Na^+$—$H^+$ Exchange in Gastric Glands as Measured with a Cytoplasmic-Trapped, Fluorescent pH Indicator. Proceedings of the National Acedemy of Sciences of the United States of America, 1985, vol. 81, pp. 7436-7440.

Park J et al. Ultra-Large-Scale Syntheses of Monodisperse Nanocrystals. Nature Materials, 2004, vol. 3, pp. 891-895.

Perez JM et al. Magnetic Relaxation Switches Capable of Sensing Molecular Interactions. Nature Biotechnology, 2002, vol. 20, pp. 816-820.

Perez JM et al. Viral-Induced Self-Assembly of Magnetic Nanoparticles Allows the Detection of Viral Particles in Biological Media. Journal of the American Chemical Society, 2003, vol. 125, pp. 10192-10193.

Raghunand N et al. Renal and Systemic pH Imaging by Contrast-Enhanced MRI. Magnetic Resonance in Medicine, 2003, vol. 49, pp. 249-257.

Rink TJ et al. Cytoplasmic pH and Free $Mg^{2+}$ in Lymphocytes. The Journal of Cell Biology, 1982, vol. 95, pp. 189-196.

Rozenman Y & Kantor HL. Heterotopic Transplanted Rat Heart: A Model for In Vivo Determination of Phosphorous Metabolites During Ischemia and Reperfusion. Magnetic Resonance in Medicine, 1990, vol. 13, pp. 450-457.

Shapiro MG et al. Dynamic Imaging with MRI Contrast Agents: Quantitative Considerations. Magnetic Resonance Imaging, 2006, vol. 24, pp. 449-462.

Strable E et al. Synthesis and Characterization of Soluble Iron Oxide-Dendrimer Composites. Chemistry of Materials, 2001, vol. 13, pp. 2201-2209.

Venditto VJ et al. PAMAM Dendrimer Based Macromolecules as Improved Contrast Agents. Molecular Pharmaceutics, 2005, vol. 2, pp. 302-311.

Wang Y et al. "Pulling" Nanoparticles into Water: Phase Transfer of Oleic Acid Stabilized Monodisperse Nanoparticles into Aqueous Solutions of $\alpha$-Cyclodextrin. Nano Letters, 2003, vol. 3, pp. 1555-1559.

Weissleder R et al. Ultrasmall Superparamagnetic Iron Oxide: An Intravenous Contrast Agent for Assessing Lymph Nodes with MR Imaging. Radiology, 1990, vol. 175, pp. 494-498.

Weissleder R. Molecular Imaging in Cancer. Science, 2006, vol. 312, pp. 1168-1171.

Xu C et al. Dopamine as a Robust Anchor to Immobilize Functional Molecules on the Iron Oxide Shell of Magnetic Nanoparticles. Journal of the American Chemical Society, 2004, vol. 126, pp. 9938-9939.

Yablonskiy DA & Haacke EM. Theory of NMR Signal Behavior in Magnetically Inhomogeneous Tissues: The Static Dephasing Regime. Magnetic Resonance in Medicine, 1994, vol. 32, pp. 749-763.

Zhang S et al. A Novel pH-Sensitive MRI Contrast Agent. Angewandte Chemie International Edition in English, 1999, vol. 38, pp. 3192-3194.

Zhang W & Simanek EE. Dendrimers Based on Melamine. Divergent and Orthogonal, Convergent Synthesis of a G3 Dendrimer. Organic Letters, 2000, vol. 2, pp. 843-845.

Zhou J et al. Using the Amide Proton Signals of Intracellular Proteins and Peptides to Detect pH Effects in MRI. Nature Medicine, 2003, vol. 9, pp. 1085-1090.

Zielinksi LJ et al. Relaxation of Nuclear Magnetization in a Nonuniform Magnetic Field Gradient and in a Restricted Geometry. Journal of Magnetic Resonance, 2000, vol. 147, pp. 95-103.

\* cited by examiner

PH-SENSITIVE IMAGING AGENTS

CROSS-REFERENCE TO RELATED APPLICATIONS

This application claims priority from U.S. Provisional Application Ser. No. 61/722,631 filed on 5 Nov. 2012, which is incorporated herein by reference in its entirety.

STATEMENT REGARDING FEDERALLY SPONSORED RESEARCH OR DEVELOPMENT

This invention was made with government support under grant number 1R15EB007074-01 awarded by National Institutes of Health; grant number 2R15EB007074-02 awarded by National Institutes of Health; grant number CHE-0343440 awarded by National Science Foundation; grant number CHE-0349255 awarded by National Science Foundation; grant number CHE-0421012 awarded by National Science Foundation; and grant number DMR-0552800 awarded by National Science Foundation. The government has certain rights in the invention.

BACKGROUND OF THE INVENTION

Molecular imaging techniques can provide detection, diagnoses, or tracking of pathological conditions, as well as insights into the underlying mechanisms of various diseases.[1] While many such approaches target specific biomolecular markers of disease, a more general biochemical parameter of increasing interest is pH. Because mammalian energy metabolism results in the production of acids (e.g., lactic acid and $CO_2/H_2CO_3$), the body must actively regulate pH in order to maintain normal healthy physiological conditions. Correspondingly, local variations (e.g., reductions) in extra- or intracellular pH can be associated with the heterogeneous blood flow and nutrient supply concomitant with a number of altered physiological states and pathological conditions, including injury, ischemia, and inflammation, as well as various cancers.[2-7]

A number of magnetic resonance (MR) modalities using either endogenous[8,9] or exogenous agents[10-27] as a more complete, less-invasive alternative to microelectrode-based pH measurements.[7] For example, increasingly elaborate exogenous agents have been developed that exploit pH-sensitive nuclear magnetic resonance (NMR) chemical shifts (e.g. $^{31}P$ or $^{19}F$)[10-16] chemical-exchange saturation transfer (CEST) effects,[9,17-20] or Gadolinium (Gd)-based $R_1$ relaxivity changes[21-24] to spectrally probe or image pH variations. Golman and co-workers[25,26] demonstrated the use of hyperpolarized $^{13}C$-bicarbonate for MRI pH mapping in vivo; while this approach avoids many aforementioned challenges, its application can be limited by the inherently short (10 s of sec) lifetime of the highly non-equilibrium nuclear spin magnetization induced by the dynamic nuclear polarization (DNP) process, and by its nature the approach requires specialized instrumentation and capabilities not generally available in hospitals and imaging clinics.

Superparamagnetic iron oxide nanoparticles (SPIONs) are a class of MRI contrast agents having high biological tolerability and large magnetic moments, giving rise to high (usually transverse) relaxivities (up to $\sim 10^2$-$10^3$ $mM^{-1} \cdot s^{-1}$ per Fe ion).[1,28-34] SPIONs can be synthesized with surface modifications to improve aqueous solubility/stability, limit aggregation, or modulate biological uptake (see e.g. Refs.[29,30]). It has been reported that certain surface functionalizations improved the information content of the SPIONs' MR response by binding specific ions[35] or biological molecules[36], thereby targeting specific tissue types or altering the SPIONs' transverse relaxivities (e.g., via analyte-modulated aggregation) to yield molecular 'switch'-based contrast.[33,37]

SUMMARY OF THE INVENTION

Among the various aspects of the present disclosure is the provision of a biocompatible imaging agent comprising a paramagnetic core; a linker group; and a pH sensitive macromolecule comprising a monomer unit, the monomer unit selected from the group consisting of a dendron, a dendrimer, and a polymer and having a pKa between 6 and 10; wherein, the linker group is affixed to the paramagnetic core; the pH sensitive macromolecule is attached to the linker group; and the imaging agent exhibits aqueous stability.

Another aspect provides a method of imaging a biological tissue comprising: administering the biocompatible imaging agent to a biological tissue; and detecting contrast associated with the imaging agent in the tissue, optionally, via magnetic resonance imaging.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1 shows dopamine-linked G1, G2, and G3 melamine dendron-functionalized SPIONs ('GX-SPIONs', where X is the dendron generation number). The inset corresponds to diagrams of dopamine-linked nitrilotriacetic acid functionalized SPIONs ('C-SPIONs') and dopamine-linked poly(1-vinylimidazole) functionalized SPIONs ('I-SPIONs').

FIG. 3A show results for control ('No SPIONs') and G2 SPION-loaded HeLa cells were obtained with the same pass of cell cultures. FIG. 3B show G1 SPIONs and G3 SPIONs along with the 'control' were achieved with the same pass of HeLa cell cultures. Note: HeLa cells used in FIG. 3A and FIG. 3B were obtained from the same HeLa cell line, but passed at different times.

FIG. 5A shows an example of a TEM image of melamine dendron-SPIONs (here, G3-SPIONs; bar is 25 nm). FIG. 5B, FIG. 5C, and FIG. 5D show high-field (7 T) relaxivity plots showing the dependencies of $R_2$ and $R_2^*$ on SPION loading for G1- (FIG. 5B), G2- (FIG. 5C), and G3-SPIONs (FIG. 5D) as a function of Fe concentration (slopes give relaxivities described, for example, in Table 1). FIG. 5E and FIG. 5F show corresponding relaxivity plots of $R_1$ (FIG. 5E) and $R_2$ (FIG. 5F) vs. Fe concentration at low field (0.5 T) for G1 and G3 SPIONs. Uncertainties for the individual data points were generally well within the graph symbols.

FIG. 6 shows SPION-loading-dependent transverse relaxation rates for PEG-G2-SPIONs, measured at 7 T; slopes of the linear fits (solid lines) give relaxivities.

FIG. 7A shows $R_2^m$ vs. pH at high-field (7 T) of gelatin phantoms (4% w/v, 150 mM acetate or phosphate buffer) loaded with G1- (green squares), G2- (red circles), or G3-SPIONs (blue triangles). FIG. 7B shows $R_2^{*m}/R_2^m$ ratio vs. pH at high-field (7 T) of gelatin phantoms (4% w/v, 150 mM acetate or phosphate buffer) loaded with G1- (green squares), G2- (red circles), or G3-SPIONs (blue triangles). Data points encircled by the white oval (at pH~5.8) and yellow oval (at pH~6.6) represent relaxivities obtained from gel samples prepared with DI water (no buffer) or PBS, respectively. Inset of FIG. 7A corresponds to plots of $R_1^m$ (purple symbols, dotted lines) and $R_2^m$ (blue symbols, solid lines) vs. pH obtained at lower field (0.5 T) for gel samples containing G3-SPIONs. Note that for each data point, values and error bars are derived from a linear fit of individual relaxation measurements performed as a function of SPION concentration under the given conditions. Connecting lines are meant only to guide the eye.

FIG. 8 is a series of plots depicting relaxivity values as a function of NaCl concentration and an illustration depicting ionic screening. FIG. 8B (inset) shows the same data as FIG. 8B, but shows the entire range of $R_2^*/R_2$ vs. [NaCl]. Connecting lines are meant only to guide the eye.

FIG. 10A shows a TEM micrograph taken from G3-SPION samples (created from 20 µg/mL aqueous solutions) at low pH (~3.5). FIG. 10B shows a TEM micrograph taken from G3-SPION samples (created from 20 µg/mL aqueous solutions) at higher pH (~8). Bars are 100 nm.

FIG. 11A shows HeLa cells cultured without SPIONs ('control'). FIG. 11B shows HeLa cells labeled with G2-SPIONs (24 hr incubation with 25 µg/mL SPIONs). FIG. 11C shows HeLa cells labeled with G1-SPIONs (24 hr incubation with 25 µg/mL SPIONs). FIG. 11D shows HeLa cells labeled with G3-SPIONs (24 hr incubation with 25 µg/mL SPIONs). Images in FIG. 11A and FIG. 11B were taken separately (with separate cultures) from those in FIG. 11C and FIG. 11D. FIG. 11E shows $R_2^*$ values for cell 'plug' samples comprising G1- or G3-loaded HeLa cells, compared to that of a control sample ('Only Cells'). FIG. 11F shows Fe loading of the cell plugs studied in FIG. 11E following acid digestion, reported in both pg Fe per cell (green, left bars) and Fe % (right blue bars). Note: values for the 'Only Cells' control sample represent the upper bound for the Fe content as determined by the detection limits of the measurements (and thus the values for this sample likely represent significant overestimates of the true Fe content).

FIG. 12A shows plots of $R_2^m$ (black open squares) and $R_2^{*m}/R_2^m$ ratio (blue closed circles) vs. pH at high-field (7 T) from gelatin phantoms (4% w/v, 20 mM acetate or phosphate buffer) loaded with I-SPIONs. Note the shift in the inflections and the opposite behavior in the trend lines compared to the melamine dendron GX-SPIONs. FIG. 12B shows corresponding plots of $R_2^m$ and $R_2^{*m}/R_2^m$ ratio (red closed circles) for samples loaded with C-SPIONs. Connecting lines are meant only to guide the eye.

DETAILED DESCRIPTION OF THE INVENTION

Figure 1:
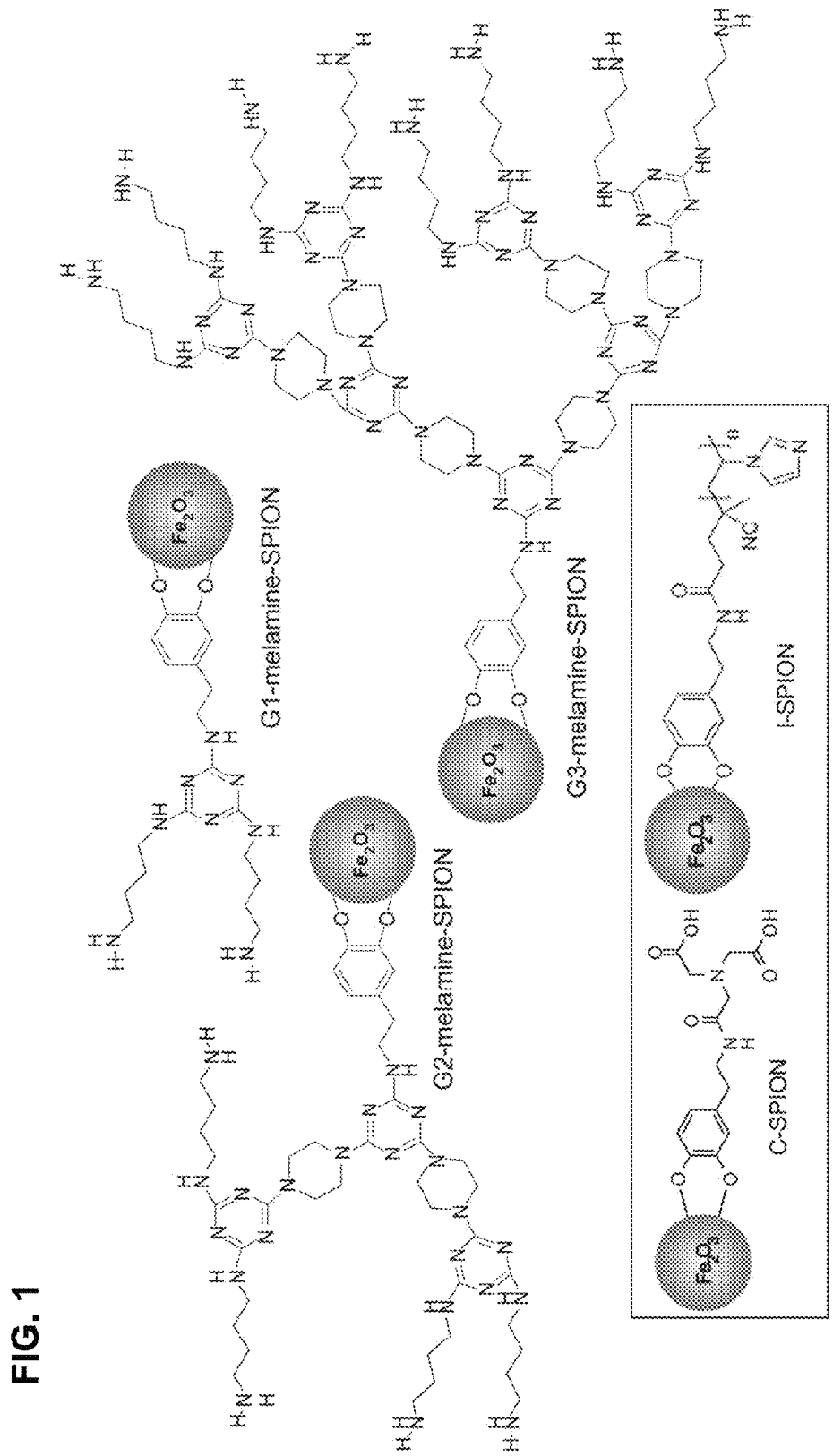
FIG. 1 is a series of chemical depicting the structure/morphology of various surface-functionalized SPIONs utilized (not to scale).

The present disclosure is based, at least in part, on the discovery that macromolecules attached to the surface of a magnetic core can cause a pH-dependent magnetic resonance response that can be detected to indicate pH variations in a sample. Studies described herein identified several functionalized cores that exhibited pH-sensitive MR response.

Magnetic resonance (MR) agents described herein can provide sufficient spectral sensitivity to local variations (e.g., modest local variations) in pH across different tissue types or physiological conditions, while also yielding sufficient detection sensitivity for high-resolution imaging, sufficient chemical stability and lifetime, low minimum dose, or high biological compatibility (e.g., low deposition of radio frequency radiation into tissues). Furthermore, MR agents described herein can provide a solution to concentration-dependency of pH-sensitive MR effects and more control of local concentration of such agents in vivo.

Studies described herein show highly pH-sensitive MR responses induced by a series of surface-functionalized superparamagnetic iron oxide nanoparticles (SPIONs) in aqueous media. In these experiments, the surface-functionalization of highly monocrystalline SPION cores (~12 nm) with three different generations of melamine-dendrons was optimized to give agents with high molar relaxivities and excellent aqueous stabilities. This allowed the sensitivity of their MR responses to the local chemical environment and the effects of dendron-generation number to be investigated in detail. $R_2^m$ and $R_2^{m*}$ values at 7 T were found to exhibit great sensitivity to pH at physiologically-relevant ionic strengths, with sharp inflections observed at pH values near the $pK_a$ of the melamine monomer (~$5.0^{38}$).

Among the various aspects described herein is a method for determining variations in pH in tissue. Such a method can be used as a diagnostic criterion for tissue pathology characterized by variations in tissue pH. Opposing behavior in the $R_2^m$ and $R_2^{m*}$ trends can be exploited to provide a ratiometric MR response to solution pH, allowing such SPIONs to act as concentration-independent pH-sensors for generating MRI contrast. Moreover, it was observed that the strength of the effect grows—and the position of the main pH inflection shifts—with increasing dendron generation, and the pH sensitivity was also manifested at lower field (0.5 T), including a strong $R_1^m$ dependence.

Provided herein is a biocompatible agent that can be used for imaging (e.g., magnetic resonance imaging or transmission electron microscopy imaging). In some embodiments, the agent includes a core molecule (e.g., a paramagnetic core), a linker group, and a macromolecule composed of a monomer unit (e.g. a dendron, a dendrimer, or a polymer), where the macromolecule can be a pH sensitive macromolecule. The monomer unit can have a pKa of, for example, between about 6 and about 10. The linker molecule can couple the core molecule and the pH sensitive macromolecule. For example, the linker group can be affixed to the paramagnetic core and the pH sensitive macromolecule, thereby coupling these components. The agent can be stable in an aqueous environment. Choice of surface-functionalization (e.g., choice of monomer unit) can increase or decrease the surface $pK_a$ to modulate the range of pH sensitivity. Thus is provided surface-functionalized imaging agent having a highly pH-sensitive imaging response.

Core Molecule

An agent (e.g., a biocompatible imaging agent) can include a core molecule coupled to a pH sensitive macromolecule via a linker group. A core molecule can be, for example, magnetic, paramagnetic, superparamagnetic, or hyperpolarized. A core molecule can include one of more of an iron oxide, gandolimium, iron paltinum, or manganese.

A core molecule as described herein can be a conventional imaging agent further modified with surface functionalization as described herein (e.g., attached to a linker in turn attach to a pH sensitive macromolecule).

An imaging agent described herein can be a contrast media used to, inter alia, improve visibility of internal body structures in magnetic resonance imaging (MRI). An MRI contrast agent can alter the relaxation times of atoms within body tissues where they are present after oral or intravenous administration. In MRI scanners, sections of the body are exposed to a very strong magnetic field, a radiofrequency pulse is applied causing some atoms (including those in contrast agents) to spin and then relax after the pulse stops. This relaxation emits energy which is detected by the scanner and can be mathematically converted into an image or the signal can be detected directly and analyzed without need for an image. The MR signal or image can be weighted in different ways giving a higher or lower signal.

Another aspect of the present disclosure provides an MR imaging agent exhibiting $T_1$, $T_2$, or $T_2^*$ weighted image enhancement, thus producing contrast in a MRI image modulated by pH (or variations thereof) of the sample.

An MRI contrast agent can work by shortening the $T_1$ relaxation time of protons located nearby. $T_1$ shortens with an increase in rate of stimulated emission from high energy states (spin anti-aligned with the main field) to low energy states (spin aligned). Thermal vibration of the strongly magnetic metal ions in the contrast agent creates oscillating electromagnetic fields at frequencies corresponding to the energy difference between the spin states (via E=hv), resulting in the requisite stimulation.

An MRI contrast agent described herein can be administered by routes used by other conventional agents. For example, an MRI agent described herein can be administered by injection (e.g., into the blood stream) or orally, which can depend on the subject, tissue or condition of interest. Oral administration can be used for, e.g., gastrointestinal tract scans. Injection administration can be used, e.g., for non-gastrointestinal tract scans.

In some embodiments, an MRI contrast agent can be administered orally. Exemplary contrast agents for oral administration include gadolinium and manganese chelates, or iron salts for $T_1$ signal enhancement. SPIO, barium sulfate, air and clay can be used to lower $T_2$ signal. Natural products with high manganese concentration such as blueberry and green tea can be used for $T_1$ increasing contrast enhancement. Perflubron, a type of perfluorocarbon, can be used as a gastrointestinal MRI contrast agent for pediatric imaging. It is thought that the contrast agent works by reducing the amount of protons (as hydrogen) in a body cavity, thus causing it to appear dark in the images.

A MRI contrast agent can be classified by, e.g., chemical composition, administration route, magnetic properties, effect on the image, metal center's presence and nature, or biodistribution or applications. MRI contrast agents classified by biodistribution can include: extracellular fluid agents (also known as intravenous contrast agents); blood pool agents (also known as intravascular contrast agents); organ specific agents (i.e., gastrointestinal contrast agents and hepatobiliary contrast agents); active targeting/cell labeling agents (i.e. tumor-specific agents); responsive (also known as smart or bioactivated) agents; and pH-sensitive agents.

An MRI contrast agent of the present disclosure can be a $T_1$, $T_2$, and $T_2^*$ contrast agent that can be administered as described herein.

Paramagnetic

Described herein are imaging agents containing a paramagnetic core molecule.

Paramagnetism is a form of magnetism whereby the paramagnetic material is attracted when in the presence of an externally applied magnetic field. In contrast with this behavior, diamagnetic materials are repelled by magnetic fields. Paramagnetic materials have a relative magnetic permeability greater or equal to unity (i.e., a positive magnetic susceptibility) and hence are attracted to magnetic fields. The magnetic moment induced by the applied field is linear in the field strength and rather weak. It typically requires a sensitive analytical balance to detect the effect and modern measurements on paramagnetic materials are often conducted with a SQUID magnetometer.

Paramagnetic materials have a small, positive susceptibility to magnetic fields. These materials are slightly attracted by a magnetic field and the material does not retain the magnetic properties when the external field is removed. Paramagnetic properties are due to the presence of some unpaired electrons, and from the realignment of the electron paths caused by the external magnetic field. Paramagnetic materials include magnesium, molybdenum, lithium, and tantalum.

Unlike ferromagnets, paramagnets do not retain any magnetization in the absence of an externally applied magnetic field, because thermal motion randomizes the spin orientations. Some paramagnetic materials retain spin disorder at absolute zero, meaning they are paramagnetic in the ground state. Thus the total magnetization drops to zero when the applied field is removed. Even in the presence of the field there is only a small induced magnetization because only a small fraction of the spins will be oriented by the field. This fraction is proportional to the field strength and this explains the linear dependency. The attraction experienced by ferromagnetic materials is non-linear and much stronger, so that it is easily observed, for instance, by the attraction between a refrigerator magnet and the iron of the refrigerator itself.

Superparamagnetic

Described herein are imaging agents containing a superparamagnetic core molecule.

Superparamagnetism is a type of paramagnetism. Some materials show induced magnetic behavior that follows a Curie type law but with exceptionally large values for the Curie constants. These materials are known as superparamagnets. They are characterized by a strong ferromagnetic or ferrimagnetic type of coupling into domains of a limited size that behave independently from one another. The bulk properties of such a system resembles that of a paramagnet, but on a microscopic level they are ordered. The materials do show an ordering temperature above which the behavior reverts to ordinary paramagnetism (with interaction). Ferrofluids are a good example, but the phenomenon can also occur inside solids, e.g., when dilute paramagnetic centers are introduced in a strong itinerant medium of ferromagnetic coupling such as when Fe is substituted in $TlCu_2Se_2$ or the alloy AuFe. Such systems contain ferromagnetically coupled clusters that freeze out at lower temperatures. They are also called micromagnets.

Hyperpolarized

Described herein are imaging agents containing a hyperpolarized core molecule.

As described herein, an imaging agent described herein can be formulated to include a hyperpolarized agent. Hyperpolarization can enhance nuclear magnetic response signal by factors of $10^4$-$10^5$ above thermal equilibrium. Magnetic resonance agents can quench or reduce the polarization of hyperpolarized agents. Quenching or reduction in hyperpolarization can cause a reduction in MR signal. A reduction in MR signal can result in contrast.

For example, a magnetic resonance (MR) agent can include a hyperpolarized agent. A hyperpolarized agent can include hyperpolarized gases, small organic molecules, dynamic nuclear polarization (DNP), field-induced polarization (FIP), or hyperpolarized nanoparticles.

A hyperpolarized gas, as described herein, can include xenon, krypton, or helium. A hyperpolarized agent can include nuclei such as $^{13}C$ or $^{15}N$ that can be polarized using DNP.

Iron Oxide

A core molecule can be an iron oxide. An iron oxide is understood to be a type of superparamagnetic contrast agent. Exemplary iron oxides include superparamagnetic iron oxide (SPIO) and ultrasmall superparamagnetic iron oxide (USPIO). These contrast agents consist of suspended colloids of iron oxide nanoparticles and when injected during imaging are known to reduce the $T_2$ signals of absorbing tissues. SPIO and USPIO contrast agents can be used, e.g., for liver tumor enhancement. Various SPIOs and USPIOs had or have regulatory approval (e.g., Lumirem/Gastromark).

An iron oxide contrast agent can be a commercially available iron oxide contrast agent, such as Feridex I.V. (also known as Endorem and ferumoxides); Resovist (also known as Cliavist); Sinerem (also known as Combidex); Lumirem (also known as Gastromark); or Clariscan™ (also known as PEG-fero, Feruglose, and NC100150).

Gadolinium (Gd)

A core molecule can be gadolinium. Gadolinium is understood to be a type of superparamagnetic contrast agent.

A gadolinium(III)-containing MRI contrast agent (often termed simply "gado" or "gad") can be used for, e.g., enhancement of vessels in MR angiography or for brain tumor enhancement associated with the degradation of the blood-brain barrier. For large vessels such as the aorta and its branches, the gadolinium(III) dose can be as low as 0.1 mmol per kg body mass. Higher concentrations can be used for finer vasculature. Gd(III) chelates do not pass the blood-brain barrier because they are hydrophilic. Thus, these can be useful in enhancing lesions or tumors where the Gd(III) leaks out. In the rest of the body, the Gd(III) can initially remain in circulation but then be distributed into the interstitial space or eliminated by the kidneys.

Types of Gadolinium(III) contrast agents include extracellular fluid agents, Blood pool agents, or organ-specific agents. Extracellular fluid agents can be ionic (e.g., Magnevist or Dotarem) or neutral (e.g., Omniscan, Prohance, Gadavist, or OptiMARK). Blood pool agents can be albumin-binding gadolinium complexes (e.g., Ablavar or Gadocoletic acid) or polymeric gadolinium complexes (e.g., Gadomelitol or Gadomer 17). Organ-specific agents can be hepatobiliary agents (e.g., Primovist and Multihance).

Gd chelated contrast agents approved by the European Medicines Agency (EMA) include: gadoterate (Dotarem); gadodiamide (Omniscan); gadobenate (MultiHance); gadopentetate (Magnevist, Magnegita, Gado-MRT ratiopharm); gadoteridol (ProHance); gadoversetamide (OptiMARK); gadoxetate (Primovist); and gadobutrol (Gadovist). Gd chelated contrast agents approved in the United States by the U.S. Food and Drug Administration (FDA) include: gadodiamide (Omniscan); gadobenate (MultiHance); gadopentetate (Magnevist); gadoteridol (ProHance); gadofosveset (Ablavar, formerly Vasovist); gadoversetamide (OptiMARK); and gadoxetate (Eovist); gadobutrol (Gadavist).

Gadolinium MRI contrast agents can be safer than an iodinated contrast agent used in X-ray radiography or computed tomography. Anaphylactoid reactions to Gadolinium MRI contrast agents are understood to be rare, occurring in approx. 0.03-0.1%.

As a free solubilized aqueous ion, gadolinium (III) can be somewhat toxic, but is generally regarded as safe when administered as a chelated compound. In animals the free Gd (III) ion can exhibit a 100-200 mg/kg 50% lethal dose, but the LD50 is increased by a factor of 100 when Gd (III) is chelated, so that its toxicity becomes comparable to iodinated X-ray contrast compounds. The chelating carrier molecule for Gd for MRI contrast use can be classified by whether they are macro-cyclic or have linear geometry and whether they are ionic or not. Cyclical ionic Gd(III) compounds are considered the least likely to release the Gd(III) ion, and hence the safest. Rare side effects of Gd(III) chelates have been reported (e.g., nephrogenic fibrosing dermopathy, also known as nephrogenic systemic fibrosis, NSF). The World Health Organization suggests "high-risk" gadolinium-containing contrast agents (e.g., Optimark, Omniscan, Magnevist, Magnegita or Gado-MRT ratiopharm) are contraindicated in subjects with severe kidney problems, in subjects who are scheduled for or have recently received a liver transplant, and in newborn babies up to four weeks of age.

Iron Platinum

A core molecule can be an iron platinum. Iron platinum oxide is understood to be a type of superparamagnetic contrast agent.

For example, superparamagnetic iron platinum particles (SIPPs) can have better $T_2$ relaxivities compared with the more common iron oxide nanoparticles. SIPPs can be encapsulated with phospholipids to create multifunctional SIPP stealth immunomicelles that specifically targeted cell types (e.g., human prostate cancer cells). Multifunctional SIPP micelles can be synthesized and conjugated to a monoclonal antibody against a tissue (e.g., prostate)-specific membrane antigen. Thus, SIPPs can be used as a tumor-specific contrast agent.

Manganese

A core molecule can be manganese.

A manganese chelate, such as Mn-DPDP, can enhance the $T_1$ signal. Exemplary use of a manganese chelate contrast agent includes detection of liver lesions. The chelate is understood to dissociate in vivo into manganese and DPDP, where the former is absorbed intra-cellularly and excreted in bile, while the latter is eliminated via the renal filtration.

Manganese ions ($Mn^{2+}$) can be used in MEMRI (Manganese Enhanced MRI). A manganese contrast agent can be used for functional brain imaging due to the ability of $Mn^{2+}$ to enter cells through Calcium $Ca^{2+}$ channels $Mn^{2+}$.

Linker Group

An agent (e.g., a biocompatible imaging agent) can include a linker group coupling a core molecule and a pH sensitive macromolecule.

A linker can be, for example, an organic molecule with at least one end having a functional group. Various linker groups are known in the art.; except as otherwise specified, compositions described herein can include state of the art linker groups. For example, a state of the art linker molecule can be any such molecule capable of coupling a core molecule and a pH sensitive macromolecule.

A linker group can include one or more of the following exemplary functional groups: carboxylic acid or carboxylate groups (e.g., Fmoc-protected-2,3-diaminopropanoic acid, ascorbic acid), silane linkers (e.g., aminopropyltrimethoxysilane (APTMS)), or dopamine. Iron on the surface of an iron oxide molecule can be under-coordinated. A linker group, such as carboxylic acid, dopamine, or silane (or another state of the art linker group), can provide missing coordination sites (e.g., two oxygen coordination sites) for binding.

A linker group can be any one or more of the following: carboxylic acid or carboxylate groups, Fmoc-protected-2,3-diaminopropanoic acid, ascorbic acid, silane linkers, aminopropyltrimethoxysilane (APTMS), or dopamine.

Macromolecule and Monomer Unit

An agent (e.g., a biocompatible imaging agent) can include a pH sensitive macromolecule coupled to a core molecule via a linker group. A macromolecule can be, for example, a dendron, dendrimer, or polymer.

As described herein, pH-sensitive magnetic resonance (MR) agents can be formulated with pH-sensitive macromolecules. For example, a pH-sensitive MR agent can be functionalized with macromolecules or functional groups of with varying pKa values.

A functional group, as described herein, can include a macromolecule or functional group having a pKa value.

A pH-sensitive magnetic resonance (MR) agent can comprise a macromolecule or functional group with a pKa value. For example, a macromolecule or functional group can have a pKa value of about 6 to about 10. As another example, a macromolecule or functional group can have a pKa value of about −2, about, −1, about 0, about 1, about 2, about 3, about 4, about 5, about 6, about 7, about 8, about 9, about 10, about 11, or about 12. It is understood that recitation of the above discrete values includes a range between each recited value.

A macromolecule can be a very large molecule commonly created by polymerization of smaller subunits. In biochemistry, the term is applied to the four conventional biopolymers (nucleic acids, proteins, carbohydrates, and lipids), as well as non-polymeric molecules with large molecular mass such as macrocycles. The individual constituent molecules of macromolecules are called monomers (mono=single, meros=part). The macromolecule itself can be pH-sensitive without further modification or functionalization.

The term macromolecule was coined by Nobel laureate Hermann Staudinger in the 1920s, although his first relevant publication on this field only mentions high molecular compounds (in excess of 1,000 atoms). At that time the phrase polymer, as introduced by Berzelius in 1833, had a different meaning from that of today: it simply was another form of isomerism for example with benzene and acetylene and had little to do with size.

Usage of the term to describe large molecules varies among the disciplines. For example, while biology refers to macromolecules as the four large molecules comprising living things, in chemistry, the term may refer to aggregates of two or more molecules held together by intermolecular forces rather than covalent bonds but which do not readily dissociate.

According to the standard IUPAC definition, the term macromolecule as used in polymer science refers only to a single molecule. For example, a single polymeric molecule is appropriately described as a "macromolecule" or "polymer molecule" rather than a "polymer", which suggests a substance composed of macromolecules.

Because of their size, macromolecules are not conveniently described in terms of stoichiometry alone. The structure of simple macromolecules, such as homopolymers, can be described in terms of the individual monomer subunit and total molecular mass. Complicated biomacromolecules, on the other hand, require multi-faceted structural description such as the hierarchy of structures used to describe proteins.

Macromolecules can have unusual physical properties. For example, individual pieces of DNA in a solution can be broken in two simply by sucking the solution through an ordinary straw. This is not true of smaller molecules. The 1964 edition of Linus Pauling's College Chemistry asserted that DNA in nature is never longer than about 5,000 base pairs. This error arose because biochemists were inadvertently and consistently breaking their samples into pieces. In fact, the DNA of chromosomes can be hundreds of millions of base pairs long.

Another common macromolecular property that does not characterize smaller molecules is their relative insolubility in water and similar solvents. Many require salts or particular ions to dissolve in water. Similarly, many proteins will denature if the solute concentration of their solution is too high or too low.

High concentrations of macromolecules in a solution can alter the rates and equilibrium constants of the reactions of other macromolecules, through an effect known as macromolecular crowding. This comes from macromolecules excluding other molecules from a large part of the volume of the solution, thereby increasing these molecules' effective concentration.

For example, a macromolecules can be bio-polymers (DNA, carbohydrates, proteins, and lipids), synthetic polymers (plastics, synthetic fibers, and synthetic rubber), graphene, and carbon nanotubes.

For example, functional groups that can be incorporated into the macromolecule for use as pH-sensitive functionalized SPIONS include macromolecules functionalized with α-amino-carboxylate, β-amino-sulfonate, beta-sulfonates, Nitrilotriacetic-acid, Poly-imidazole (poly(1-vinylimidazole)), and histidine-lysine.

For example, the macromolecule can be any one or more of the following: a dendron, dendrimer, polymer, bio-polymer, such as DNA, carbohydrates, proteins, and lipidssynthetic polymers, such as plastics, synthetic fibers, and synthetic rubber), graphene, and carbon nanotubes; each of which can be functionalized by one or more of the following: α-amino-carboxylate, β-amino-sulfonate, beta-sulfonates, Nitrilotriacetic-acid, Poly-imidazole (poly(1-vinylimidazole)), and histidine-lysine Dendrons and Dendrimers Dendrons, and their larger brethren, dendrimers, can provide high aqueous stability to molecular imaging contrast agents, in addition to having low toxicity, the ability to modulate biological uptake and to be bio-functionalized to target specific tissues.[43] Dendrons have been utilized in a variety of applications including: Gd-based MRI contrast agents,[43] synthetic matrices for novel SPION-dendrimer conjugates[29,30], and cellular transfection agents for conventional SPIONs.[32] Additionally, unlike many polymers, dendrons have well-defined chemical structures with precisely scalable and tunable physical properties. Dendron-functionalized SPIONs[41,44] are used here as a springboard for better understanding the effect of SPION surface properties on MR behavior, and how such effects can be exploited to improve MR sensitivity to changes in the local chemical environment.

Dendrimers can be repetitively branched molecules. The name comes from the Synonymous terms for dendrimer include arborols and cascade molecules. However, dendrimer is currently the internationally accepted term. A dendrimer is typically symmetric around the core, and often adopts a spherical three-dimensional morphology. The word dendron is also encountered frequently. A dendron can contain a single chemically addressable group called the focal point. The first dendrimers were made by divergent synthesis approaches by Fritz Vögtle in 1978, R. G. Denkewalter at Allied Corporation in 1981, Donald Tomalia at Dow Chemical in 1983 and in 1985, and by George Newkome in 1985. In 1990 a convergent synthetic approach was introduced by Jean Fréchet. Dendrimer popularity then greatly increased, resulting in more than 5,000 scientific papers and patents by the year 2005.

Dendritic molecules are characterized by structural perfection. Dendrimers and dendrons are monodisperse and usually highly symmetric, spherical compounds. The field of dendritic molecules can be roughly divided into low-molecular weight and high-molecular weight species. The first category includes dendrimers and dendrons, and the latter includes dendronized polymers, hyperbranched polymers, and the polymer brush.

The properties of dendrimers are dominated by the functional groups on the molecular surface, however, there are examples of dendrimers with internal functionality. Dendritic encapsulation of functional molecules allows for the isolation of the active site, a structure that mimics that of active sites in biomaterials. Also, it is possible to make dendrimers water soluble, unlike most polymers, by functionalizing their outer shell with charged species or other hydrophilic groups. Other controllable properties of dendrimers include toxicity, crystallinity, tecto-dendrimer formation, and chirality.

Dendrimers are also classified by generation, which refers to the number of repeated branching cycles that are performed during its synthesis. For example if a dendrimer is made by convergent synthesis, and the branching reactions are performed onto the core molecule three times, the resulting dendrimer is considered a third generation dendrimer. Each successive generation results in a dendrimer roughly twice the molecular weight of the previous generation. Higher generation dendrimers also have more exposed functional groups on the surface, which can later be used to customize the dendrimer for a given application.

Specific examples of synthetic procedure for the Simanek-type dendron can be found in Example 1.

One of the very first dendrimers, the Newkome dendrimer, was synthesized in 1985. This macromolecule is also commonly known by the name arborol. The synthesis is started by nucleophilic substitution of 1-bromopentane by triethyl sodiomethanetricarboxylate in dimethylformamide and benzene. The ester groups were then reduced by lithium aluminium hydride to a triol in a deprotection step. Activation of the chain ends was achieved by converting the alcohol groups to tosylate groups with tosyl chloride and pyridine. The tosyl group then served as leaving groups in another reaction with the tricarboxylate, forming generation two. Further repetition of the two steps leads to higher generations of arborol.

Poly(amidoamine), or PAMAM, is perhaps the most well known dendrimer. The core of PAMAM is a diamine (commonly ethylenediamine), which is reacted with methyl acrylate, and then another ethylenediamine to make the generation-0 (G-0) PAMAM. Successive reactions create higher generations, which tend to have different properties. Lower generations can be thought of as flexible molecules with no appreciable inner regions, while medium sized (G-3 or G-4) do have internal space that is essentially separated from the outer shell of the dendrimer. Very large (G-7 and greater) dendrimers can be thought of more like solid particles with very dense surfaces due to the structure of their outer shell. The functional group on the surface of PAMAM dendrimers is ideal for click chemistry, which gives rise to many applications.

Dendrimers can be considered to have three major portions: a core, an inner shell, and an outer shell. Ideally, a dendrimer can be synthesized to have different functionality in each of these portions to control properties such as solubility, thermal stability, and attachment of compounds for particular applications. Synthetic processes can also precisely control the size and number of branches on the dendrimer. There are two defined methods of dendrimer synthesis, divergent synthesis and convergent synthesis. However, because the actual reactions consist of many steps needed to protect the active site, it is difficult to synthesize dendrimers using either method. This makes dendrimers hard to make and very expensive to purchase. At this time, there are only a few companies that sell dendrimers; Polymer Factory Sweden AB commercializes biocompatible bis-MPA dendrimers and Dendritech is the only kilogram-scale producers of PAMAM dendrimers. Dendritic Nanotechnologies Inc., from Mount Pleasant, Mich., USA produces PAMAM dendrimers and other proprietary dendrimers In the divergent synthetic method, the dendrimer is assembled from a multifunctional core, which is extended outward by a series of reactions, commonly a Michael reaction. Each step of the reaction must be driven to full completion to prevent mistakes in the dendrimer, which can cause trailing generations (some branches are shorter than the others). Such impurities can impact the functionality and symmetry of the dendrimer, but are extremely difficult to purify out because the relative size difference between perfect and imperfect dendrimers is very small.

In the convergent synthetic methods, dendrimers are built from small molecules that end up at the surface of the sphere, and reactions proceed inward building inward and are eventually attached to a core. This method makes it much easier to remove impurities and shorter branches along the way, so that the final dendrimer is more monodisperse. However dendrimers made this way are not as large as those made by divergent methods because crowding due to steric effects along the core is limiting.

Dendrimers have also been prepared via click chemistry, employing Diels-Alder reactions, thiol-yne reactions and azide-alkyne reactions. There are ample avenues that can be opened by exploring this chemistry in dendrimer synthesis.

Applications of dendrimers typically involve conjugating other chemical species to the dendrimer surface that can function as detecting agents (such as a dye molecule), affinity ligands, targeting components, radioligands, imaging agents, or pharmaceutically active compounds. Dendrimers have very strong potential for these applications because their structure can lead to multivalent systems. In other words, one dendrimer molecule has hundreds of possible sites to couple to an active species. Researchers aimed to utilize the hydrophobic environments of the dendritic media to conduct photochemical reactions that generate the products that are synthetically challenged. Carboxylic acid and phenol terminated water soluble dendrimers were synthesized to establish their utility in drug delivery as well as conducting chemical reactions in their interiors. This might allow researchers to attach both targeting molecules and drug molecules to the same dendrimer, which could reduce negative side effects of medications on healthy cells.

Dendrimers can also be used as a solubilizing agent. Since their introduction in the mid-1980s, this novel class of dendrimer architecture has been a prime candidate for hosts guest chemistry. Dendrimers with hydrophobic core and hydrophilic periphery have shown to exhibit micelle-like behavior and have container properties in solution. The use of dendrimers as unimolecular micelles was proposed by Newkome in 1985. This analogy highlighted the utility of dendrimers as solubilizing agents. The majority of drugs available in pharmaceutical industry are hydrophobic in nature and this property in particular creates major formulation problems. This drawback of drugs can be ameliorated by dendrimeric scaffolding, which can be used to encapsulate as well as to solubilize the drugs because of the capability of such scaffolds to participate in extensive hydrogen bonding with water. Dendrimer labs throughout the planet are persistently trying to manipulate dendrimer's solubilizing trait, in their way to explore dendrimer as drug delivery and target specific carrier.

Dendrimers can be used as drug delivery agents. Approaches for delivering unaltered natural products using polymeric carriers is of widespread interest, dendrimers have been explored for the encapsulation of hydrophobic compounds and for the delivery of anticancer drugs. The physical characteristics of dendrimers, including their monodispersity, water solubility, encapsulation ability, and large number of functionalizable peripheral groups, make these macromolecules appropriate candidates for evaluation as drug delivery vehicles. There are three methods for using dendrimers in drug delivery: first, the drug is covalently attached to the periphery of the dendrimer to form dendrimer prodrugs, second the drug is coordinated to the outer functional groups via ionic interactions, or third the dendrimer acts as a unimolecular micelle by encapsulating a pharmaceutical through the formation of a dendrimer-drug supramolecular assembly. The use of dendrimers as drug carriers by encapsulating hydrophobic drugs is a potential method for delivering highly active pharmaceutical compounds that may not be in clinical use due to their limited water solubility and resulting suboptimal pharmacokinetics. Dendrimers have been widely explored for controlled delivery of antiretroviral bioactives The inherent antiretroviral activity of dendrimers enhances their efficacy as carriers for antiretroviral drugs The dendrimer enhances both the uptake and retention of compounds within cancer cells, a finding that was not anticipated at the onset of studies. The encapsulation increases with dendrimer generation and this method may be useful to entrap drugs with a relatively high therapeutic dose. Studies based on this dendritic polymer also open up new avenues of research into the further development of drug-dendrimer complexes specific for a cancer and/or targeted organ system. These encouraging results provide further impetus to design, synthesize, and evaluate dendritic polymers for use in basic drug delivery studies and eventually in the clinic.

Dendrimers can be used as gene delivery agents. The ability to deliver pieces of DNA to the required parts of a cell includes many challenges. Current research is being performed to find ways to use dendrimers to traffic genes into cells without damaging or deactivating the DNA. To maintain the activity of DNA during dehydration, the dendrimer/DNA complexes were encapsulated in a water soluble polymer, and then deposited on or sandwiched in functional polymer films with a fast degradation rate to mediate gene transfection. Based on this method, PAMAM dendrimer/DNA complexes were used to encapsulate functional biodegradable polymer films for substratemediated gene delivery. Research has shown that the fast degrading functional polymer has great potential for localized transfection.

Dendritic structures can be used in sensor technologies. Studied systems include proton or pH sensors using poly (propylene imine), cadmium-sulfide/polypropylenimine tetrahexacontaamine dendrimer composites to detect fluorescence signal quenching, and poly(propylenamine) first and second generation dendrimers for metal cation photodetection amongst others.

Dendrimers can be used as blood substitutes. Their steric bulk surrounding a heme-mimetic centre significantly slows degradation compared to free heme, and prevents the cytotoxicity exhibited by free heme.

Dendrimers can be used in the synthesis of monodisperse metallic nanoparticles. Poly(amidoamide), or PAMAM, dendrimers are utilized for their tertiary amine groups at the branching points within the dendrimer. Metal ions are introduced to an aqueous dendrimer solution and the metal ions form a complex with the lone pair of electrons present at the tertiary amines. After complexion, the ions are reduced to their zerovalent states to form a nanoparticle that is encapsulated within the dendrimer. These nanoparticles range in width from 1.5 to 10 nanometers and are aptly called Dendrimer-Encapsulated Nanoparticles.

Dendronized polymers (or dendronised polymers) are linear polymers to every repeat unit of which dendrons are attached. Dendrons are regularly branched, tree-like fragments and for larger ones the polymer backbone is wrapped to give sausage-like, cylindrical molecular objects where the back bone is polymethylmethacrylate (PMMA), of which the methyl group is replaced by a dendron of the third generation (three consecutive branching points).

Dendronized polymers can contain several thousands of dendrons in one macromolecule and have a stretched out, anisotropic structure. In this regard they differ from the more or less spherically shaped dendrimers, where a few dendrons are attached to a small, dot-like core resulting in an isotropic structure. Depending on dendron generation, the polymers differ in thickness. Neutral and charged dendronized polymers are highly soluble in organic solvents and in water, respectively. This is due to their low tendency to entangle. Dendronized polymers have been synthesized with, e.g., polymethylmethacrylate, polystyrene, polyacetylene, polyphenylene, polythiophene, polyfluorene, poly(phenylene vinylene), poly(phenylene acetylene), polysiloxane, polyoxanorbornene, poly(ethylene imine)(PEI) backbones. Molar masses up to 200 Mio g/mol have been obtained. Dendronized polymers have been investigated for/as bulk structure control, responsivity to external stimuli, single molecule chemistry, templates for nanoparticle formation, catalysis, electro-optical devices, and bio-related applications.

The two main approaches into this class of polymers are the macromonomer route and the attach-to route. In the former, a monomer which already carries the dendron of final size is polymerized. In the latter the dendrons are constructed generation by generation directly on an already existing polymer. The macromonomer route results in shorter chains for higher generations and the attach-to route is prone to lead to structure imperfections as an enormous number of chemical reactions have to be performed for each macromolecule.

A dendron or dendrimer can be any one or more of the following: Simanek-type, Newkome, arborol, Poly(amidoamine) (PAMAM), or dendronized polymer.

Polymer

Described herein are novel imaging agents comprising polymers as macromolecules.

A polymer is a chemical compound or mixture of compounds consisting of repeating structural units created through a process of polymerization. A polymer can be a structure composed of multiple repeating units, from which originates a characteristic of high relative molecular mass and attendant properties. The units composing polymers derive, actually or conceptually, from molecules of low relative molecular mass. The term was coined in 1833 by Jöns Jacob Berzelius, though with a definition distinct from the modern IUPAC definition. Polymers are studied in the fields of biophysics and macromolecular science, and polymer science (which includes polymer chemistry and polymer physics). Historically, products arising from the linkage of repeating units by covalent chemical bonds have been the primary focus of polymer science; emerging important areas of the science now focus on non-covalent links. Because of the stipulation as to repeating substructures, polymers are formally a subclass of the category of macromolecules; the polyisoprene of latex rubber and the polystyrene of styrofoam are examples of polymeric natural/biological and synthetic polymers, respectively. In biological contexts, essentially all biological macromolecules (i.e., proteins (polyamides), nucleic acids (polynucleotides), and polysaccharides) are purely polymeric, or are composed in large part of polymeric components (e.g., isoprenylated/lipid-modified glycoproteins, where small lipidic molecule and oligosaccharide modifications occur on the polyamide backbone of the protein.

Hence, the terms polymer and polymeric material encompass very large, broad classes of compounds, both natural and synthetic, with a wide variety of properties. Because of the extraordinary range of properties of polymeric materials, they play an essential and ubiquitous roles in everyday life, from those of familiar synthetic plastics and other materials of day-to-day work and home life, to the natural biopolymers that are fundamental to biological structure and function.

Natural polymeric materials such as shellac, amber, wool, silk and natural rubber have been used for centuries. A variety of other natural polymers exist, such as cellulose, which is the main constituent of wood and paper. The list of synthetic polymers includes synthetic rubber, Bakelite, neoprene, nylon, PVC, polystyrene, polyethylene, polypropylene, polyacrylonitrile, PVB, silicone, and many more.

Most commonly, the continuously linked backbone of a polymer used for the preparation of plastics consists mainly of carbon atoms. A simple example is polyethylene ('polythene' in British English), whose repeating unit is based on ethylene monomer. However, other structures do exist; for example, elements such as silicon form familiar materials such as silicones, examples being Silly Putty and waterproof plumbing sealant. Oxygen is also commonly present in polymer backbones, such as those of polyethylene glycol, polysaccharides (in glycosidic bonds), and DNA (in phosphodiester bonds).

Polymerization is the process of combining many small molecules known as monomers into a covalently bonded chain or network. During the polymerization process, some chemical groups may be lost from each monomer. This is the case, for example, in the polymerization of PET polyester. The monomers are terephthalic acid (HOOC—$C_6H_4$—COOH) and ethylene glycol (HO—$CH_2$—$CH_2$—OH) but the repeating unit is —OC—$C_6H_4$—COO—$CH_2$—$CH_2$—O—, which corresponds to the combination of the two monomers with the loss of two water molecules. The distinct piece of each monomer that is incorporated into the polymer is known as a repeat unit or monomer residue.

Laboratory synthetic methods are generally divided into two categories, step-growth polymerization and chain-growth polymerization. The essential difference between the two is that in chain growth polymerization, monomers are added to the chain one at a time only, whereas in step-growth polymerization chains of monomers may combine with one another directly. However, some newer methods such as plasma polymerization do not fit neatly into either category. Synthetic polymerization reactions may be carried out with or without a catalyst. Laboratory synthesis of biopolymers, especially of proteins, is an area of intensive research.

There are three main classes of biopolymers: polysaccharides, polypeptides, and polynucleotides. In living cells, they may be synthesized by enzyme-mediated processes, such as the formation of DNA catalyzed by DNA polymerase. The synthesis of proteins involves multiple enzyme-mediated processes to transcribe genetic information from the DNA to RNA and subsequently translate that information to synthesize the specified protein from amino acids. The protein may be modified further following translation in order to provide appropriate structure and functioning.

Many commercially important polymers are synthesized by chemical modification of naturally occurring polymers. Prominent examples include the reaction of nitric acid and cellulose to form nitrocellulose and the formation of vulcanized rubber by heating natural rubber in the presence of sulfur. Ways in which polymers can be modified include oxidation, cross-linking and end-capping.

Especially in the production of polymers, the gas separation by membranes has acquired increasing importance in the petrochemical industry and is now a relatively well-established unit operation. The process of polymer degassing is necessary to suit polymer for extrusion and pelletizing, increasing safety, environmental, and product quality aspects. Nitrogen is generally used for this purpose, resulting in a vent gas primarily composed of monomers and nitrogen.

Polymer properties are broadly divided into several classes based on the scale at which the property is defined as well as upon its physical basis. The most basic property of a polymer is the identity of its constituent monomers. A second set of properties, known as microstructure, essentially describe the arrangement of these monomers within the polymer at the scale of a single chain. These basic structural properties play a major role in determining bulk physical properties of the polymer, which describe how the polymer behaves as a continuous macroscopic material. Chemical properties, at the nano-scale, describe how the chains interact through various physical forces. At the macro-scale, they describe how the bulk polymer interacts with other chemicals and solvents.

The identity of the monomer residues (repeat units) comprising a polymer is its first and most important attribute. Polymer nomenclature is generally based upon the type of monomer residues comprising the polymer. Polymers that contain only a single type of repeat unit are known as homopolymers, while polymers containing a mixture of repeat units are known as copolymers. Poly(styrene), for example, is composed only of styrene monomer residues, and is therefore classified as a homopolymer. Ethylene-vinyl acetate, on the other hand, contains more than one variety of repeat unit and is thus a copolymer. Some biological polymers are composed of a variety of different but structurally related monomer residues; for example, polynucleotides such as DNA are composed of a variety of nucleotide subunits.

A polymer molecule containing ionizable subunits is known as a polyelectrolyte or ionomer.

The microstructure of a polymer (sometimes called configuration) relates to the physical arrangement of monomer residues along the backbone of the chain. These are the elements of polymer structure that require the breaking of a covalent bond in order to change. Structure has a strong influence on the other properties of a polymer. For example, two samples of natural rubber may exhibit different durability, even though their molecules comprise the same monomers.

An important microstructural feature of a polymer is its architecture, which relates to the way branch points lead to a deviation from a simple linear chain. A branched polymer molecule is composed of a main chain with one or more substituent side chains or branches. Types of branched polymers include star polymers, comb polymers, brush polymers, dendronized polymers, ladders, and dendrimers.

A polymer's architecture affects many of its physical properties including, but not limited to, solution viscosity, melt viscosity, solubility in various solvents, glass transition temperature and the size of individual polymer coils in solution.

A variety of techniques may be employed for the synthesis of a polymeric material with a range of architectures, for example Living polymerization.

The physical properties of a polymer are strongly dependent on the size or length of the polymer chain. For example, as chain length is increased, melting and boiling temperatures increase quickly. Impact resistance also tends to increase with chain length, as does the viscosity, or resistance to flow, of the polymer in its melt state. Chain length is related to melt viscosity roughly as $1:10^{3.2}$, so that a tenfold increase in polymer chain length results in a viscosity increase of over 1000 times. Increasing chain length furthermore tends to decrease chain mobility, increase strength and toughness, and increase the glass transition temperature ($T_g$). This is a result of the increase in chain interactions such as Van der Waals attractions and entanglements that come with increased chain length. These interactions tend to fix the individual chains more strongly in position and resist deformations and matrix breakup, both at higher stresses and higher temperatures.

A common means of expressing the length of a chain is the degree of polymerization, which quantifies the number of monomers incorporated into the chain. As with other molecules, a polymer's size may also be expressed in terms of molecular weight. Since synthetic polymerization techniques typically yield a polymer product including a range of molecular weights, the weight is often expressed statistically to describe the distribution of chain lengths present in the same. Common examples are the number average molecular weight and weight average molecular weight. The ratio of these two values is the polydispersity index, commonly used to express the "width" of the molecular weight distribution. A final measurement is contour length, which can be understood as the length of the chain backbone in its fully extended state.

The characterization of a polymer requires several parameters which need to be specified. This is because a polymer actually consists of a statistical distribution of chains of varying lengths, and each chain consists of monomer residues which affect its properties.

A variety of lab techniques are used to determine the properties of polymers. Techniques such as wide angle X-ray scattering, small angle X-ray scattering, and small angle neutron scattering are used to determine the crystalline structure of polymers. Gel permeation chromatography is used to determine the number average molecular weight, weight average molecular weight, and polydispersity. FTIR, Raman and NMR can be used to determine composition. Thermal properties such as the glass transition temperature and melting point can be determined by differential scanning calorimetry and dynamic mechanical analysis. Pyrolysis followed by analysis of the fragments is one more technique for determining the possible structure of the polymer. Thermogravimetry is a useful technique to evaluate the thermal stability of the polymer. Detailed analysis of TG curves also allow us to know a bit of the phase segregation in polymers. Rheological properties are also commonly used to help determine molecular architecture (molecular weight, molecular weight distribution and branching) as well as to understand how the polymer will process, through measurements of the polymer in the melt phase. Another polymer characterization technique is Automatic Continuous Online Monitoring of Polymerization Reactions (ACOMP) which provides real-time characterization of polymerization reactions. It can be used as an analytical method in R&D, as a tool for reaction optimization at the bench and pilot plant level and, eventually, for feedback control of full-scale reactors. ACOMP measures in a model-independent fashion the evolution of average molar mass and intrinsic viscosity, monomer conversion kinetics and, in the case of copolymers, also the average composition drift and distribution. It is applicable in the areas of free radical and controlled radical homo- and copolymerization, polyelectrolyte synthesis, heterogeneous phase reactions, including emulsion polymerization, adaptation to batch and continuous reactors, and modifications of polymers.

A polymer can be any one or more of the following: comb polymers, brush polymers, dendronized polymers, ladders, dendrons, dendrimers, proteins (polyamides), nucleic acids (polynucleotides), polysaccharides, isoprenylated/lipid-modified glycoproteins, polyethylene, polyethylene glycol, polysaccharides (in glycosidic bonds), DNA (in phosphodiester bonds), polysaccharides, polypeptides, polynucleotides, homopolymers, copolymers, Poly(styrene), Ethylene-vinyl acetate, polyelectrolyte or ionomer.

Magnetic Resonance (MR) Imaging

Agents described herein can be used in various imaging protocols, such as magnetic resonance imaging (MRI). An MRI contrast agent of the present disclosure can be pH-sensitive, as described and tested. A pH-sensitive MRI contrast agent can be weighted to produce contrast or generate maps according to pH variation.

Described herein are novel pH-sensitive imaging agents that can exhibit transient, reversible SPION clustering modulated by pH. Thus, as demonstrated herein, the modulation of imaging agent clustering can be used to detect pH variations in a given sample. Various approaches described herein can increase or decrease the surface $pK_a$ to modulate the range of pH sensitivity. One of ordinary skill will understand that discussion surrounding pH-sensitive SPIONs can be adapted to other core molecules (e.g., other than SPIONs) of the MR imaging agent family.

Magnetic resonance imaging techniques using imaging agents are well known (see e.g. ref.[62]). Except as otherwise noted herein, compositions and methods of the present disclosure can be carried out in accordance with such state of the art techniques and agents.

Transmission Electron Microscopy (TEM) Imaging.

In some embodiments, imaging comprises Transmission Electron Microscopy (TEM) imaging. Transmission electron microscopy techniques are well known (see e.g., ref.[63]). Except as otherwise noted herein, compositions and methods of the present disclosure can be carried out in accordance with such protocols.

An imaging agent used in TEM can include one or more of the following: pH-sensitive, pH-mapping, contrast enhancing, relaxation-weighted, $T_1$, $T_2$, and $T_2^*$ weighted, iron oxide, superparamagnetic iron oxide, ultrasmall superparamagnetic iron oxide, gadolinium, iron platinum, manganese, manganese chelate, manganese ion, magnetic, paramagnetic, or superparamagnetic, or any other core molecule described herein.

Formulation of pH-Sensitive Magnetic Resonance (MR) Agent

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a diagnostically effective amount of an agent described herein, which can be in purified form, together with a suitable amount of carrier so as to provide the form for proper administration to the subject.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Detection Methods

Also provided is a process of detecting pH variations in a biological tissue or sample of biological tissue from a subject in need thereof by administering an effective amount of imaging agent to the biological tissue. An imaging agent can be a contrast agent. For example, a biological tissue can be any water containing sample, tissue, or tissue sample of a subject.

Methods described herein are generally performed on a subject in need thereof. A subject in need of the detection methods described herein can be a subject having, diagnosed with, suspected of having, or at risk for developing diseases that are characterized by tissue pH variations, such as cancer, acidosis, or alkalosis. A determination of the need for treatment will typically be assessed by a history and physical exam consistent with the disease or condition at issue. Treatment of the various conditions detected by the methods described herein is within the skill of the art. The subject can be an animal subject, including a mammal, such as horses, cows, dogs, cats, sheep, pigs, mice, rats, monkeys, guinea pigs, and chickens, and humans. For example, the subject can be a human subject.

Generally, a safe and effective amount of imaging agent is, for example, that amount that would cause the desired detection in a subject while minimizing undesired side effects. In various embodiments, an effective amount of imaging agent described herein can detect pathological tissue that is characterized by abnormal pH variations.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in detection as described herein, an effective amount of imaging agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical procedure, in a sufficient amount to detect tissue characterized by pH variation.

The amount of a composition described herein that can be combined with a pharmaceutically acceptable carrier to produce a single dosage form will vary depending upon the host and the particular mode of administration. It will be appreciated by those skilled in the art that the unit content of agent contained in an individual dose of each dosage form need not in itself constitute an effective amount for detection, as the necessary therapeutically effective amount could be reached by administration of a number of individual doses.

Toxicity and detection effectiveness of compositions described herein can be determined by standard pharmaceutical procedures in cell cultures or experimental animals for determining the $LD_{50}$ (the dose lethal to 50% of the population).

The specific effective dose level for any particular subject will depend upon a variety of factors including the tissue and specific pathology being detected; the age, body weight, general health, sex and diet of the subject; the time of administration; the route of administration; the rate of excretion of the composition employed; the duration of the administration and detection; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4$^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired effect and to gradually increase the dosage until the desired effect is achieved. If desired, the composition may be used for single time-point detection or longitudinal detection of pathology. The composition may be used, for example, to detect pathological tissues such as tumors, tumor margins, during or after surgery to image tumor margins. It will be understood, however, the effective detection dose of the compounds and compositions of the present disclosure will be decided by an attending physician or clinician within the scope of sound medical judgment.

Again, each of the states, diseases, disorders, and conditions, described herein, as well as others, can be detected from compositions and methods described herein. Generally, detecting a state, disease, disorder, or condition includes detection in a mammal that may be afflicted with or predisposed to the state, disease, disorder, or condition but does not yet experience or display clinical or subclinical symptoms thereof.

Administration of the pH-sensitive imaging agent can occur as a single event or over a time course of imaging modalities. For example, the imaging agent can be administered daily, weekly, bi-weekly, or monthly and monitored. For time-course imaging protocols (e.g., monitoring disease progression or regression, post-surgical imaging) the time course of treatment can be at least several days, to months, to years.

Detection in accord with the methods described herein can be performed prior to, concurrent with, or after conventional treatment modalities for diseases or conditions characterized by variations in tissue pH.

An imaging agent can be administered simultaneously or sequentially with another imaging agent, such as iron oxide, gadolinium, iron platinum, manganese, or another agent. For example, an imaging agent can be administered simultaneously with another agent, such as iron oxide, gadolinium, iron platinum, manganese, or another agent. Simultaneous administration can occur through administration of separate compositions, each containing one or more of an imaging agent, such as iron oxide, gadolinium, iron platinum, manganese, or another agent. Simultaneous administration can occur through administration of one composition containing two or more of an imaging agent such as iron oxide, gadolinium, iron platinum, manganese, or another agent. An imaging agent can be administered sequentially with iron oxide, gadolinium, iron platinum, manganese, or another agent. For example, an imaging agent can be administered before or after administration of iron oxide, gadolinium, iron platinum, manganese, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to an imaging agent comprising a paramagnetic core, a linker group, and a pH-sensitive macromolecule. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference at least with respect to the cited portions thereof and in their entirety to the extent permitted by law for all purposes to the same extent as if each individual publication, patent, patent application or other reference or cited portion thereof was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

SPION Preparation/Synthesis

The following example describes the preparation and synthesis of functionalized SPIONs.

Simanek-Type Melamine Dendron-Functionalized SPIONs (GX-SPIONS).

Figure 2:
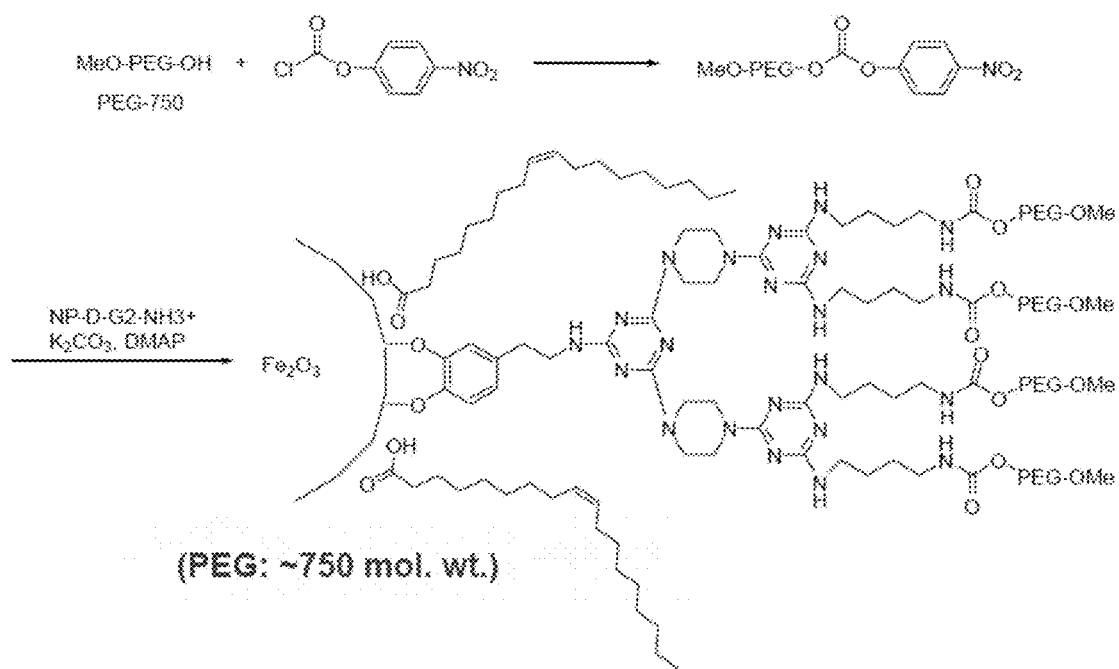
FIG. 2 is a schematic representation depicting the synthetic protocol for the synthesis of PEG-ylated G2-SPIONs.

Simanek-type[39,40] melamine dendron-functionalized SPIONs (see e.g., FIG. 2) were prepared by modifying a previously described procedure.[41] Briefly, oleate-coated maghemite ($\gamma$-$Fe_2O_3$) nanoparticles[42] (~12 nm) and dopamine-linked melamine dendron molecules of three different generations ("G1", "G2", and "G3") were each synthesized as previously described. For each dendron-SPION conjugate, the dendron molecules were dissolved in 2.5 mL MeOH and added to oleate-SPIONs in 2.5 mL $CHCl_3$ (2 mg/0.05 mL) and sonicated under Ar. The dendron-to-SPION-core ratio and sonication time were optimized; it was found that using a higher dendron-to-SPION-core ratio (~0.06 mmol melamine dendrons to 25 mg of SPION cores) and an 8 hr sonication time yielded dendron-SPIONs with the best properties (dendron surface loadings, stabilities, and MR properties). Dendron-SPIONs were collected by permanent magnet (LifeSep™ 50sx) and washed with MeOH and $CHCl_3$ three times each, and stored in MeOH. The synthesic protocol for PEGylated G2-SPIONs ('PEG'=poly (ethylene glycol), PEG-750) is illustrated in FIG. 2.

Dopamine-linked Poly-imidazole Functionalized SPIONs (I-SPIONs). Dopamine-linked poly-imidazole (I-SPIONs; see e.g., FIG. 1 inset) were prepared as follows. The same oleate-coated SPION cores used above (5 mL of a 0.00579 g/0.1 mL solution) were added to acetonitrile (1 mL), collected using a magnet, then washed with EtOH. TMAOH solution (10 mL of a 0.1 M solution) was added; the solution was sonicated for 10 minutes and stirred at room temperature for 1 hour. NaCl solution (2 mL) was added to precipitate the nanoparticles, which were then collected using the permanent magnet then washed 2× with distilled water. This process was then repeated (except with 1 day of stirring before NaCl precipitation) to yield 5 mL of aqueous SPION dispersion with a concentration 0.7 mg/0.1 mL.

0.2 mmole dopamine was added to 0.4 mmole sodium bicarbonate, dissolved in MeOH (2 mL), and purged with Ar for 5 min. TMAOH-treated nanoparticles (50 mg suspended in $CHCl_3$) were added, and the resulting mixture was purged with $N_2$ gas for 2 minutes, sonicated for 7 hours, then kept at room temperature for three days and washed with DMF and $CHCl_3$ three times to make an iron-oxide-OH-dopamine nanoparticle solution. Iron-oxide-OH-dopamine nanoparticles (30 mL of 10 mg/mL stock solution in $CHCl_3$) was added to a mixture of: AIBN carboxylic acid (0.36 mmoles), EDCI (0.72 mmoles), and of di-isopropyl ethylamine (55.8 mg) and stirred for 24 hr at room temperature. Nanoparticles were collected using a permanent magnet and washed with $CHCl_3$ and DMF. The resulting iron-oxide-OH-dopamine-AIBN carboxylic acid nanoparticles were dispersed in 5 mL DMF as a stock solution. Iron-oxide-OH-dopamine-AIBN carboxylic acid nanoparticles (5 ml of 15.6 mg/mL stock solution) were degassed for 5 minutes while stirring. Vinyl-imidazole monomer (18 mmoles) was added and stirred at 900 rpm while heating to 60° C. for 6.5 hr. The resulting DI-SPION nanoparticles were collected using a permanent magnet, washed with DMF and distilled water (twice), and stored in 5 mL of water as stock solution.

Nitrilotriacetic-Acid Functionalized SPIONs (C-SPIONs).

Nitrilotriacetic-acid functionalized SPIONs (C-SPIONs; see e.g., FIG. 1 inset) were prepared as follows. Iron-oxide-OH-dopamine nanoparticles (250 mg in $CHCl_3$) were added to a mixture of: nitrilotriacetic acid (69 mg), EDCI (138 mg), and of di-isopropyl ethylamine (55.8 mg) at room temperature in $CHCl_3$ (30 mL). After 12 hours, nanoparticles were collected using a permanent magnet and washed with $CHCl_3$, DMF and Milli-Q water sequentially. The resulting C-SPIONs were dispersed in 5 mL of Milli-Q water as stock solution before use.

Carboxylic Acid-Linked Poly-Imidazole SPIONs (I-SPIONS).

A similar preparation was used to successfully synthesize poly-imidazole SPIONs linked with carboxylic acid moieties instead of dopamine groups, but these SPIONs were found to have lower aqueous stabilities and inferior MR properties.

The study shows the functionalization of ~12 nm highly monocrystalline SPION cores with three different generations of melamine-dendrons; Nitrilotriacetic-acid functionalized SPIONs (C-SPIONs); and Poly-imidazole SPIONs (I-SPIONs).

Example 2

SPION Characterization

The following example describes the characterization of the SPIONs using elemental analysis and transmission electron microscopy (TEM).

Elemental Analysis.

Elemental analyses of the dendron-functionalized SPIONs were performed by Galbraith Laboratories, Inc. (Knoxville, Tenn.). The Fe wt % for each type of SPION was pre-determined by elemental analysis of dry SPIONs (prepared under high vacuum at 80° C. overnight) taken from each stock solution, allowing the Fe concentration (in mM Fe) of a given sample to be determined based on the SPION loading (in μg/mL). Corresponding C—H—N elemental analysis data provided the percentage of nitrogen atoms on the SPIONs' surfaces, allowing determination of the molar surface loading of dendron molecules for each GX-SPION type. The elemental analysis allowed determination of the organic and inorganic (iron oxide) fractions for the GX-SPIONs; note that while some un-exchanged oleic acid moieties may remain on these SPIONs, nitrogen atoms are found only in the dendron surface moieties. Correspondingly, the C—H—N analysis data permitted the weight percentage of nitrogen atoms on the SPIONs' surfaces to be obtained, giving 0.73%, 1.98%, and 1.99% for G1-, G2-, and G3-SPIONs, respectively. According to the molecular structures, each G1, G2, and G3 melamine dendron molecule possesses 8, 22, and 50 nitrogen atoms, respectively. Surface loading of dendrons for each generation of SPIONs were obtained according to the following example calculation (here, for G1-SPIONs): First, moles of nitrogen in 1 g of the SPION-dendron conjugates determined by: $0.73 \times 10^{-2}/14 = 5.214 \times 10^{-4}$ mole/g. Then, since each G1-melamine dendron molecule contains 8 nitrogen atoms, the mole amount of G1-dendron in each gram of G1-SPIONs is: $5.214 \times 10^{-4}/8 = 6.52 \times 10^{-5}$ mole/g. Corresponding results for all GX-SPIONs created for this work, compared to those created previously[41] summarized below in Table 1.

properties. As with the 'old' SPIONs, decreased molar dendron surface-loading with increasing 'G'-number was obtained (reflecting the increasing dendron bulk); however, this reduction is more than compensated by the exponential rise in terminal groups going from G1 to G3 (as manifested by the nitrogen surface concentration). Note that the number of protonatable sites (i.e., those that can bear charge) scales with the N atom concentration.

Transmission Electron Microscopy (TEM) Imaging.

SPION size distribution and structural viability were checked via TEM (see e.g., FIG. 4A)[41] before and after surface functionalization; SPION average core dimension: 12 nm, with size distributions typically <10%. TEM images were also taken of G3-SPIONs following preparation in 150 mM buffer solutions at pH~3 and ~8 (using acetic acid/acetate and phosphoric acid/phosphate buffers, respectively); for each pH, a 20 μg/mL G3-SPION solution was prepared and then sonicated for 30 s before loading onto a hydrophilic plasma-treated TEM plate prior to imaging. All TEM images were obtained with a Hitachi 7100 TEM (SIUC Microimaging Facility) operating at an accelerating voltage of 75, 100 or 300 KV. Images were captured using a Gatan 789 digital camera. Magnification was calibrated using a MAG*I*CAL high-resolution magnification standard accurate to $1 \times 10^6$ X.

Example 3

In Vitro Cellular Studies

The following example describes the in vitro studies of cellular uptake, compatibility, and MR response of the dendron-functionalized SPIONs in HeLa cell cultures.

HeLa cells were cultured in MEM (minimum essential media) at 37° C. in a humidified atmosphere containing 5% $CO_2$ for 24 hours. When cell growth was ~60% confluent (i.e., ~60% plate coverage), G1-, G2-, or G3-SPIONs suspended in MEM (25 μg/mL) were added to the cells and incubated for an additional 24 hours. Following incubation, cells were washed 3 times with phosphate buffer (PBS, pH=7.4) to remove SPIONs that were not uptaken by the cells.

Studies of cellular uptake, compatibility, and MR response were then performed on different subsets of identically-prepared plates of HeLa cells for each type of dendron-functionalized SPION studied. The cells from one

TABLE 1

Comparison of properties (dendron surface loadings and relaxivities) of GX-SPIONs created for this work ('new' SPIONs) using the optimized procedure described in the primary manuscript, versus those created in previous work ('old' SPIONs)[41].

| SPION type | Dendron loading (μmol/g) | N atom @ surface (mmol/g) | 7 T, 18° C. | | | | 0.5 T, 40° C. | |
|---|---|---|---|---|---|---|---|---|
| | | | $R_1^m$ ($s^{-1} \times mM^{-1}$) | $R_2^m$ ($s^{-1} \times mM^{-1}$) | $R_2^{*m}$ ($s^{-1} \times mM^{-1}$) | $R_2^{*m}/R_2^m$ | $R_1^m$ ($s^{-1} \times mM^{-1}$) | $R_2^m$ ($s^{-1} \times mM^{-1}$) |
| 'old' G1 | 46.4 | 0.371 | 0.29 ± 0.05 | 114 ± 10 | 770 ± 120 | 6.75 | — | — |
| 'new' G1 | 65.2 | 0.521 | 0.93 ± 0.03 | 333 ± 10 | 412 ± 7 | 1.23 | 33 ± 0.7 | 197 ± 7 |
| 'old' G2 | 23.0 | 0.507 | 0.09 ± 0.03 | 264 ± 23 | 530 ± 60 | 2.01 | — | — |
| 'new' G2 | 64.3 | 1.414 | 0.76 ± 0.05 | 312 ± 9 | 338 ± 9 | 1.08 | — | — |
| 'old' G3 | 21.3 | 1.060 | 0.03 ± 0.03 | 204 ± 14 | 460 ± 40 | 2.35 | — | — |
| 'new' G3 | 28.4 | 1.421 | 0.54 ± 0.02 | 304 ± 5 | 342 ± 14 | 1.13 | 21 ± 7 | 175 ± 5 |

Figure 3:
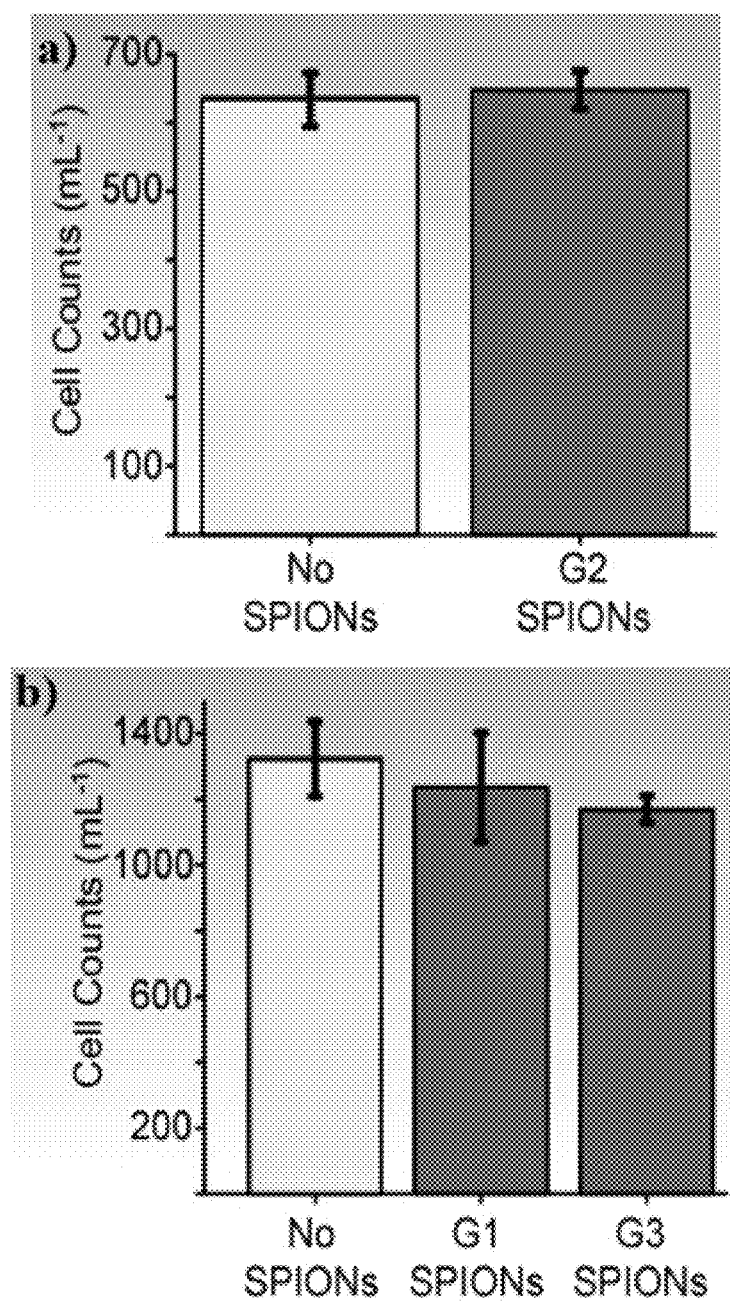
FIG. 3 is a series of bar graphs depicting cell counting/viability results for SPION-loaded HeLa cells. In all cases, at least 3 plates of cells were measured; bars represent average values (and error bars represent uncertainties including standard deviations).

As shown by the data in the Table 1, performing the ligand-exchange reactions with varied dendron concentrations and sonication times produced dendron-SPIONs with significantly improved surface functionalization and MR subset of plates were fixed with 4% formaldehyde for 30 minutes and then Prussian-blue stained with 2% potassium ferrocyanide and 6% HCl solution for an additional 30 minutes. These cells were then examined under a light microscope and optical micrographs were obtained to qualitatively characterize SPION uptake. Corresponding tests of cellular compatibility were performed by measuring cell growth following incubation with SPIONs and compared with controls (incubated in the absence of SPIONs); following the cell-washing cycles the cells were trypsinized and counted using a standard Beckman cell counter (see e.g., FIG. 3). Finally, for a subset of HeLa cell plates cultured with G1- or G3-SPIONs, following incubation, cells were trypsinized, removed from plates, spun down to form cell 'plugs', and loaded into NMR tubes for relaxivity studies. Following MR measurement, the cell plugs were acid-digested and sent for Fe-quantification via elemental analysis as described above.

Figure 4:
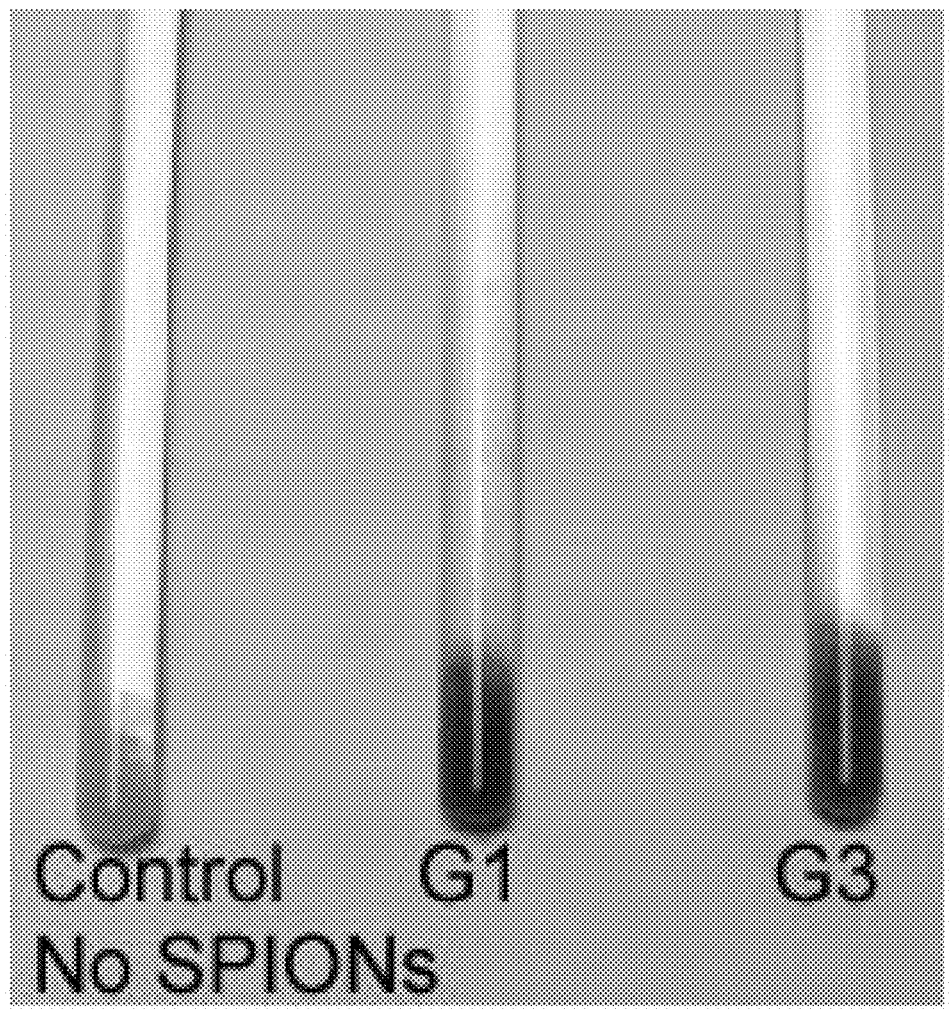
FIG. 4 is a photograph of spun-down cell 'plugs' loaded in 5 mm NMR tubes for MR experiments.
Figure 5:
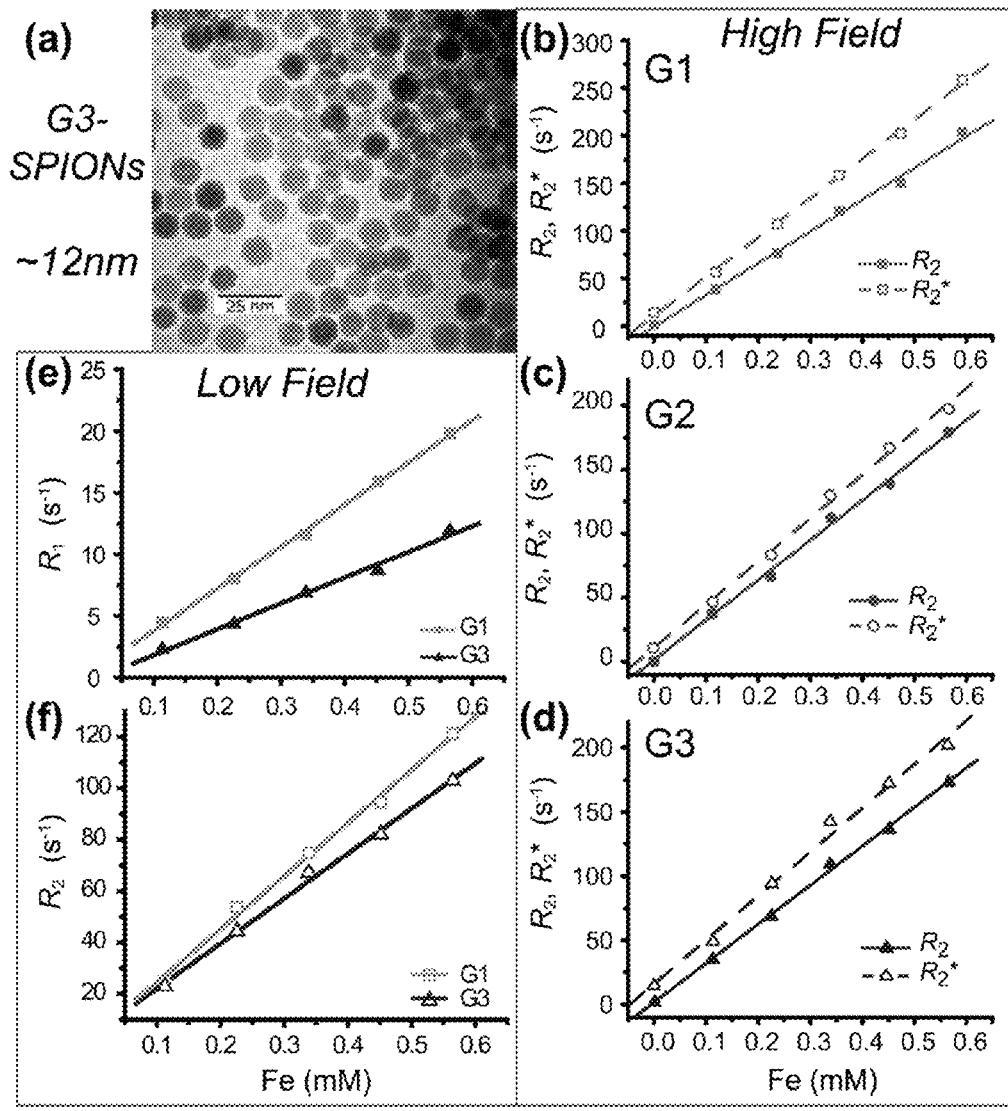
FIG. 5 is a series of images and graphs depicting melamine dendron-SPIONs and corresponding relaxivity plots.

Preliminary biocompatibility studies were performed by introducing SPIONs to the HeLa cells after 60% confluency and incubated for 24 hours. The cells were then washed with PBS buffer to remove the excess SPIONs in media, trypsinized, and counted using a standard Beckman cell counter. Results are summarized in FIG. 3. Initial results were obtained with G2-SPIONs (see e.g., FIG. 3A); once the protocol was optimized, corresponding experiments were performed on a different cell culture using G1- and G3-SPIONs (see e.g., FIG. 3B). Little or no deleterious effects from incubation of SPIONs were observed. Finally, a photo showing the cell 'plugs' used in the MR measurements is shown in FIG. 4 (corresponding portions of these cells were acid-digested and sent for elemental analysis).

Example 4

MR Relaxivity Studies

The following example describes the sample preparation and experimental protocol for the measurement of the MR relaxivities.

Sample Preparation.

For a given type of SPION and experiment, an array of gelatin 'phantoms' (4% w/v) with varied SPION concentrations (0-50 μg/mL) were prepared in standard 5 mm NMR tubes from pre-measured SPION stock solutions diluted with DI water, a selected pH buffer, or NaCl stock solution to give 500 μL total volume with the desired final concentrations. For pH-dependent experiments, buffer solutions containing either acetic acid/acetate (for phantoms with $3 \leq pH \leq 6.5$) or phosphoric acid/phosphate (for samples with $pH \geq 6$) were used; unless stated otherwise, all pH experiments involving GX-SPIONs used 150 mM final buffer concentrations, whereas 20 mM final buffer concentrations were utilized for C-SPION and I-SPION experiments. pH measurements were performed before and immediately after sample preparation using an Oakton ION 510 pH meter and single-junction pH probe prior to placing the samples in cold storage (4° C.) overnight to set the gelatin suspensions. SPION-loaded HeLa cell samples were prepared and characterized as described above.

MR Measurements.

Aqueous $^1H$ longitudinal ($R_1=1/T_1$), transverse ($R_2=1/T_2$), and inhomogeneous dephasing ($R_2*=1/T_2*$) relaxation rates were measured at either 7.05 T (at 18° C., using a 300 MHz Varian Inova NMR spectrometer) or 0.5 T (at 40° C., using a 23 MHz Oxford Maran Ultra spectrometer located at Washington University Medical School, St. Louis, Mo.). Relativities exhibited little or no sensitivity to temperature over the investigated range (15-40° C.; data not shown). $T_1$ and $T_2$ relaxation times were measured via inversion-recovery and Carr-Purcell-Meiboom-Gill (CPMG) pulse sequences (nominal spin echo time τ=1 ms) respectively; high-field (7 T) $R_2*$ values were estimated from line widths following a standard 90°-acquire sequence using the relationship $\Delta\nu_{FWHM}=(\pi T_2*)^{-1}$ ($R_2*$ values were not obtained at 0.5 T owing to the high magnetic field inhomogeneity of that type of relaxometer). Samples were stored at 4° C. when not in use; for all SPIONs studied, spin relaxation rates were not observed to change significantly over several months. For a given SPION type and set of experimental conditions, corresponding molar relaxivity values (respectively denoted $R_1^m$, $R_2^m$, and $R_2*^m$ for clarity) are given by the slope obtained by linearly fitting the experimentally determined spin relaxation rates when plotted versus the molar Fe concentration.

Example 5

Relaxivity Measurement of Melamine Dendron-Functionalized SPIONs

This example describes the measurement of the relaxivities of melamine dendron-functionalized SPIONs.

FIG. 5B-F show measurements of aqueous $^1H$ spin relaxation rates at 7 and 0.5 T from buffer-free gelatin-phantoms prepared with variable concentrations of G1-, G2-, or G3-dendron-SPIONs; corresponding nominal relaxivities are provided in Table 2. As expected, for buffer-free phantoms, $R_1^m$ is poorly sensitive to SPIONs at 7 T due to reduced susceptibility to dipolar contributions at high field, as well as the presence of bulky surface groups hindering the surface accessibility of water to the SPION cores. However, due to the superparamagnetic nature of the γ-$Fe_2O_3$ cores, $R_2^m$ and $R_2*^m$ values are highly sensitive to the presence of the functionalized SPIONs (see e.g., FIG. 5). These relaxivities are also mildly dependent on dendron generation, and the effects on $R_1^m$ and $R_2^m$ are consistent with the steric crowding of dendron branches thus resulting in the reduced accessibility of water molecules to the magnetic SPION core. Larger $R_2*^m$ values for G1-SPIONs would be consistent with a slightly greater degree of clustering—consistent with greater values of the $R_2*^m/R_2^m$ ratio. At lower field, $R_2^m$ values are relatively high but reduced by ~40% compared to high-field values which is qualitatively consistent with the reduced (but still nearly saturated) field-induced magnetic response expected at 0.5 T. $R_1^m$ values, however, are ~35-fold higher at 0.5 T which is consistent with reduced suppression of dipolar contributions to $T_1$ at lower fields and comparable to the relaxivities of available Gd-based $T_1$ contrast agents used in clinically relevant magnetic fields.[21-24] High relaxivities (e.g., $R_2^m$~300 $mM^{-1} \cdot s^{-1}$ Fe), $R_2^m*/R_2^m$ ratios approaching unity (implying magnetically homogeneous samples), highly linear responses, excellent aqueous stabilities, and terminal group variability of these dendron-functionalized SPIONs indicate an excellent platform for the development of a new group of MR contrast agents.

TABLE 2

Relaxivity measurements for G1-, G2-, and G3-SPIONs.

| Relaxivities | G1 | G2 | G3 |
|---|---|---|---|
| $R_1^{m\ddagger}$ | 0.93 ± 0.4 | 0.76 ± 0.3 | 0.54 ± 0.4 |
| $R_1^{m\dagger}$ | 33 ± 0.7 | — | 21 ± 1.0 |
| $R_2^{m\ddagger}$ | 333 ± 10 | 312 ± 9 | 304 ± 5 |
| $R_2^{m\dagger}$ | 197 ± 7 | — | 175 ± 6 |
| $R_2*^{m\ddagger}$ | 412 ± 7 | 338 ± 9 | 342 ± 14 |

All relaxivities listed in units of ($s^{-1} \times mM^{-1}$)
‡7 T at 18° C.
†0.5 T at 40° C.

The study shows optimization of the of SPIONs functionalized with three different generations of melamine-dendrons led to agents possessing high molar relaxivities (including $R_2^m$ values exceeding 300 $s^{-1} \cdot mM^{-1}$) and excellent aqueous stabilities-allowing the sensitivity of their MR responses to the local chemical environment and the effects of dendron-generation number to be studied.

Example 6

Comparison of MR Relaxivities for PEG-G2-SPIONs Vs. Standard G2-SPIONs

The following example describes the MR relaxivity properties for EGylated SPIONs compared to standard G2-SPIONs.

Figure 6:
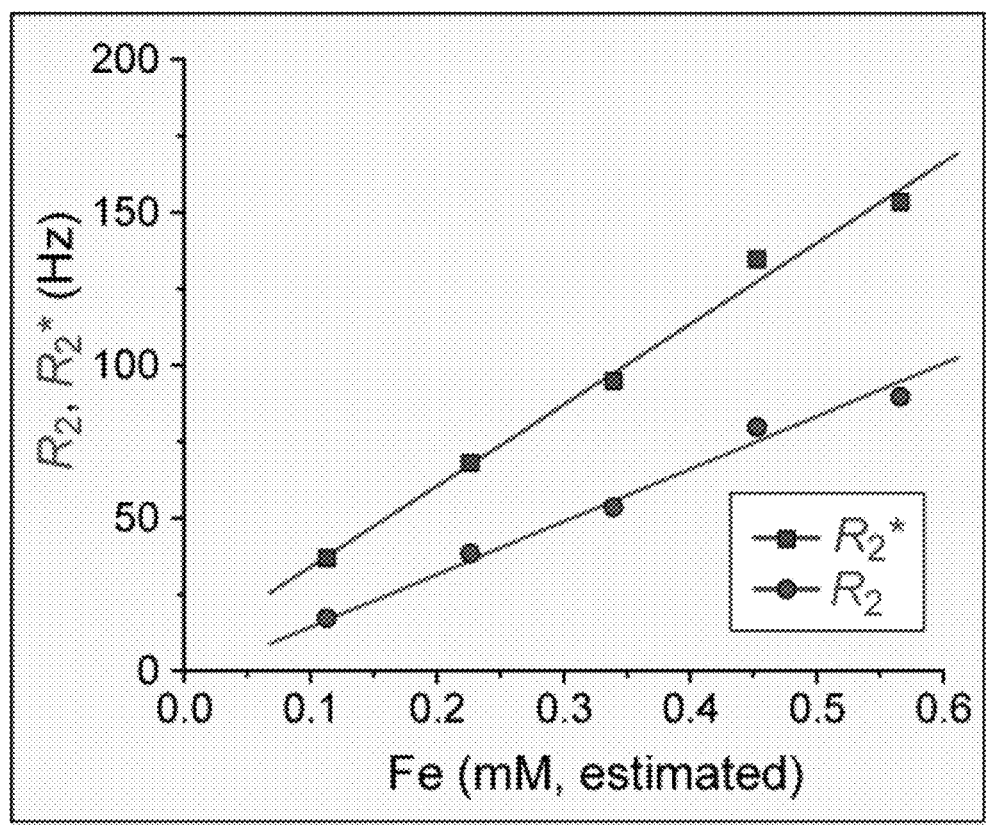
FIG. 6 is a plot depicting transverse relaxation rates for PEG-G2 SPIONs.

The successful preparation of PEG-G2-SPIONs yielded agents with good aqueous stability and only small reductions in the transverse $^1H$ relaxivities compared to standard melamine G2-SPIONs (see e.g., FIG. 6). PEGylation has previously been exploited to suppress unwanted uptake of agents (including nanoparticles (see, e.g. Refs.[45-47]) by the reticuloendothelial system following introduction to the body (otherwise resulting in poor in vivo agent delivery efficiency). Thus, evaluation of the effects of PEGylation on the pH-sensing capabilities of a given dendron-SPION could be important in the evaluation of other pH-sensitive agents.

MR measurements at 7 T were obtained from gelatin samples containing various loadings of PEG-G2-SPIONs to permit comparison of relaxivities with those values measured from "old" and "new" G2-SPIONs. Measurements of transverse relaxivities for PEG-G2-SPIONs are shown in FIG. 6. Results are summarized below in Table 3. Although absolute relaxivities are reduced somewhat in the PEG-G2-SPIONs compared to the G2-SPIONs, the values are still high relative to other SPION constructs, and good linear behavior is observed over the range of concentrations studied.

TABLE 3

Relaxivities of PEG-G2-SPIONs, compared with corresponding values from ('old' and 'new') G2-SPIONs.

| Quantity | Old-G2 | New-G2 | PEG-G2 |
|---|---|---|---|
| Aq. 'Solubility'/Stability | ~1 dy | >many wks | n.d. |
| $R_1^m$ | 0.09 | 0.76 | 0.22 |
| $R_2^m$ | 264 | 312 | 172 |
| $R_2^{*m}$ | 530 | 337 | 265 |

Example 7

Sensitivity of GX-SPION MR Responses to pH

The following example describes the pH sensitivity of dendron-functionalized SPIONs.

Figure 7:
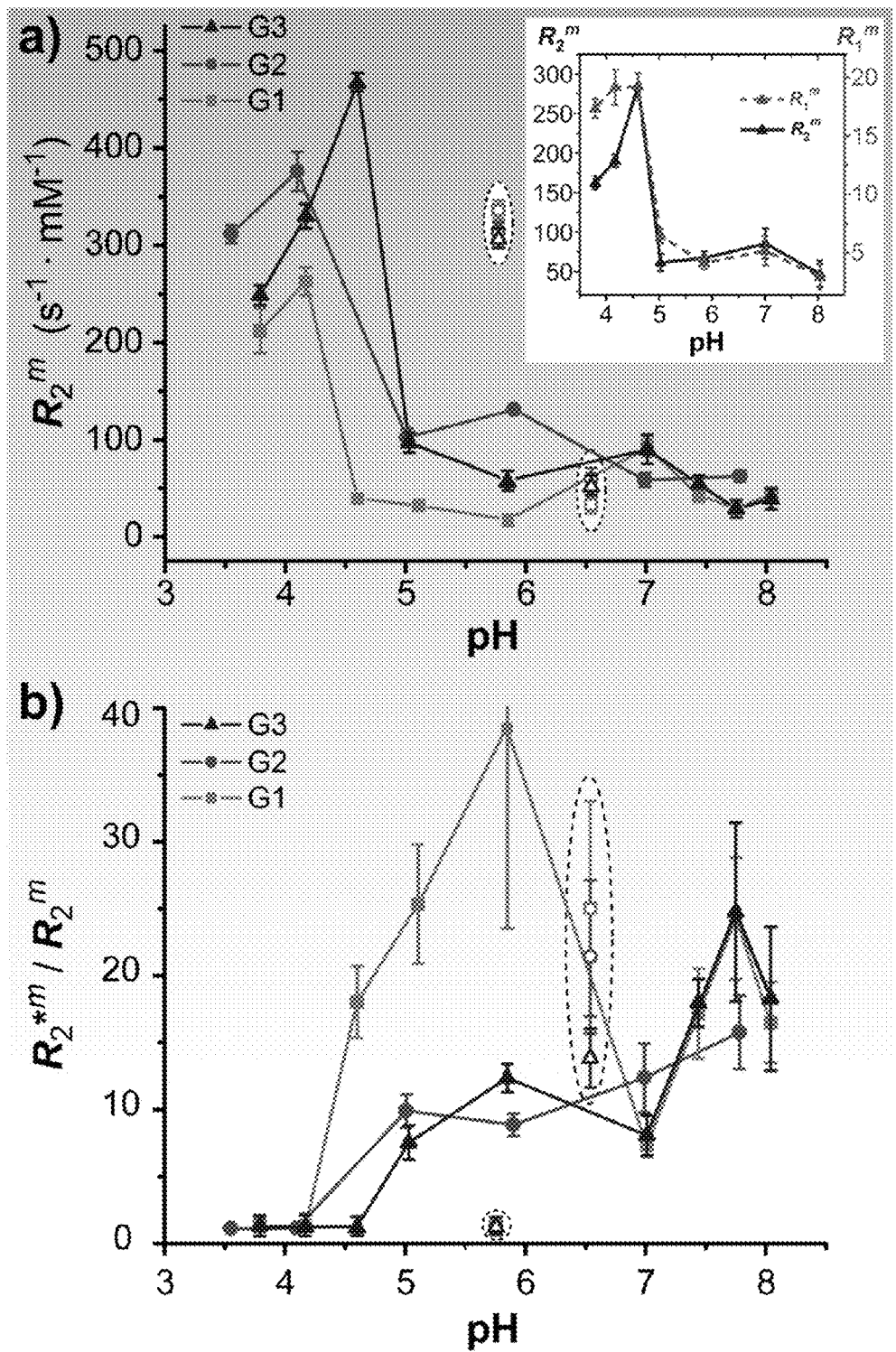
FIG. 7 is a series of plots depicting relaxivities values as a function of pH at high-field.

The melamine dendron-functionalized SPIONs were observed to have MR responses that are highly sensitive to the solution environment. For example, both $R_2^m$ and $R_2^{*m}$ exhibit enhanced sensitivity to solution pH at 7 T at physiologically-relevant ionic strengths, with responses varying by over an order of magnitude (see e.g., FIG. 7). As shown in FIG. 7A, the large $R_2^m$ values observed in the absence of buffer—and at low pH in 150 mM buffers—decrease significantly at higher pH values; sharp inflections are observed just below pH values near the $pK_a$ of melamine monomer (~$5.0^{38}$). Moreover, the magnitude of the effect grows—and the position of the main pH inflection shifts—with increasing dendron generation. It is worth noting that such pH-sensitive responses are not typical for SPIONs (see e.g., Ref.[48]).

Next, for all three generations of SPIONs, $R_2^{*m}$ values were observed to follow $R_2^m$ values at low pH; however, at higher pH $R_2^{*m}$ values were observed to grow significantly—exhibiting the opposite trend of the $R_2^m$ behavior. Correspondingly, the $R_2^{m*}/R_2^m$ ratio (see e.g., FIG. 7B) demonstrates significant, dendron-generation-dependent sensitivity to pH. The position of the inflection points of $R_2^{*m}/R_2^m$ for these experiments increases with generation (see e.g., FIG. 7B), and the magnitude of the observed change is larger for G1 compared to G2 and G3. Thus, the $R_2^{*m}/R_2^m$ ratio is one example of an MR response that could be determined independently from SPION loading to provide a concentration-independent pH sensor of the local environment.

Corresponding spin-relaxation studies at 0.5 T showed that the pH effect was also clearly manifested at low field—including a strong $R_1^m$ dependence (varying by ~5-fold (see e.g., FIG. 7A inset)—pointing to another approach for generating contrast. Of course, while the low-field $R_2^m$ values roughly track those of $R_1^m$ effects, they are much larger in magnitude. Indeed, at 0.5 T, $R_2^m$ values are nearly identical to those at 7 T, but merely scaled down by ~35% (as would be expected from the smaller field-dependent magnetic response of the SPION cores).

One effect that is not yet fully understood is the apparent deviation from sigmoidal behavior observed at low pH (i.e., the initial rise in molar relaxivity ($R_2^m$) to very high values—even higher than the nominal (buffer-free) measurements for G2, G3-SPIONs—just before the main inflection (see e.g., FIG. 7A); this effect is reproducible and also appears to scale with dendron generation. And while the low-field $R_1^m$ curve closely follows that of $R_2^m$ over most of the pH range studied, it is noted that $R_1^m$ did not exhibit the same initial rise at low pH and instead more closely follows traditional sigmoidal behavior (see further discussion below in Example 8).

The study shows highly pH-sensitive MR responses induced by a series of surface-functionalized SPIONs in aqueous media. Further, relaxivities were found to vary by an order of magnitude by varying the solution pH at physiologically-relevant ionic strengths, with sharp inflections near the $pK_a$ of the monomer of the surface functionalization (and with magnitude of the effect and inflection position depending on the dendron generation). Opposing $R_2^m$ and $R_2^{m*}$ behavior may allow such SPIONs to act as concentration-independent pH-sensing contrast agents (e.g., trends may be exploited to provide a ratiometric MR response to pH). Moreover, it was observed that the strength of the effect grows—and the position of the main pH inflection shifts—with increasing dendron generation, and the pH sensitivity was also manifested at lower field (0.5 T), including a strong $R_1^m$ dependence. On the other hand, relatively high (~30 $s^{-1} \cdot mM^{-1}$) and pH-variable $R_1$ relaxivities at lower, more clinically-relevant fields suggest the possibility of using such SPIONs as $T_1$ agents (offering the advantage of positive MRI contrast).

Example 8

Sensitivity of GX-SPION MR Response to Solution Ionic Strength

The following example describes the ionic strength sensitivity of dendron-functionalized SPIONs.

The above observations are consistent with SPION pH sensitivity primarily resulting from transient clustering governed by the interplay of aggregation tendencies vs. charge repulsion forces: i.e., at lower pH values, the dendron surface functionalities should be more positively charged, repelling the SPIONs from each other, thereby allowing greater surface access of water molecules to the superparamagnetic cores—in turn giving rise to high $R_2$ values (and relatively high $R_1$ values at low field). On the other hand, if the surfaces were poorly charged, and/or if the surface charges of different SPIONs were effectively screened from each other (as would be expected at higher ionic strengths), the SPIONs would tend to cluster, reducing the access of water molecules to the SPION surfaces but greatly increasing the microscale magnetic inhomogeneity of the sample—giving rise to very high $R_2^*$ values.

Figures 8A, 8B:
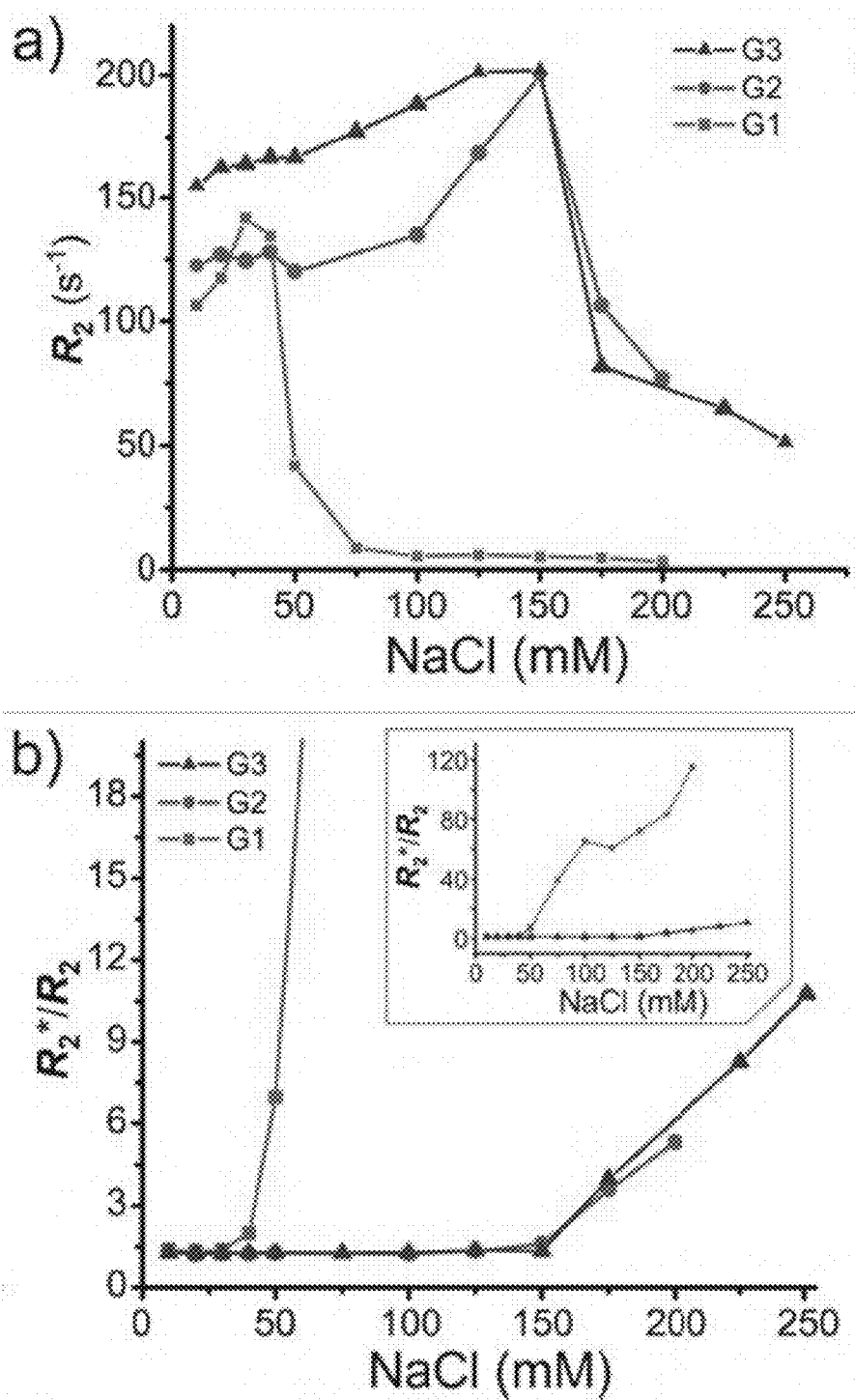
FIG. 8A shows $R_2$ values (measured at 7 T) vs. NaCl concentration in gelatin phantoms (4% w/v) each loaded with a fixed amount (40 µg/mL) of G1- (green squares), G2- (red circles), or G3-SPIONs (blue triangles).
FIG. 8B shows $R_2^*/R_2$ ratios (measured at 7 T) vs. NaCl concentration in gelatin phantoms (4% w/v) each loaded with a fixed amount (40 µg/mL) of G1- (green squares), G2- (red circles), or G3-SPIONs (blue triangles).
Figure 8C:
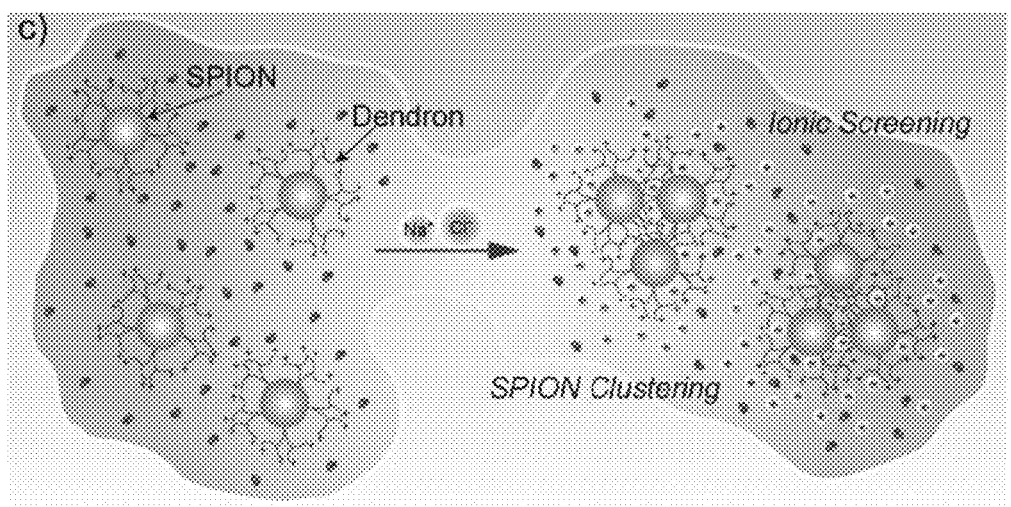
FIG. 8C shows an illustration depicting transient, reversible microscale clustering of the dendron-SPIONs governed by the interplay of aggregation tendencies vs. charge repulsion forces (modulated by ionic screening).

To gain further insight into this clustering hypothesis, $T_2$ values of G1-, G2-, and G3-functionalized SPIONs were measured with fixed SPION loading (40 μg/mL) but varying ionic strength (i.e., NaCl concentration) at the natural pH of the gelatin-phantoms prepared with DI water (no buffer, pH ~5.8). As predicted, for all three generations of SPIONs, dependences of $R_2$ and $R_2^*$ on ionic strengths (see e.g., FIG. 8) qualitatively followed the behavior observed with varying pH (see e.g., FIG. 7). More specifically, $R_2$ values initially increased as a result of increasing salt concentration then sharply fell at higher salt concentration (see e.g., FIG. 8A), mimicking the high pH results). In contrast, $R_2^*$ values increased with rising solution ionic strength, giving rise to $R_2^*/R_2$ ratios that were flat at low ionic strengths but grew significantly at as the ionic strength was increased (see e.g., FIG. 8B). Moreover, a dendron-generation-dependent effect was once again observed. $R_2$ values peaked at higher ionic strengths for the G2- and G3-SPIONs compared to G1-SPIONs, and correspondingly, the $R_2^*/R_2$ ratio for the G1-SPIONs exhibited much greater sensitivity to ionic strength than the G2- and G3-SPIONs (see e.g., FIG. 8B inset). These observations also support the clustering hypothesis (see e.g., FIG. 8C), as higher-generation dendrons should give rise to larger SPION surface-charge densities at a given pH value—charges that would require increasingly high ionic strengths to be effectively screened (see e.g., the dendron surface loadings of these SPIONs as determined by elemental analysis in Table 1).

As mentioned above, an initial rise in $R_2$ values with increasing ionic strength (see e.g., FIG. 8A) was observed that mimicked the initial rise in $R_2^m$ relaxivities recorded below the inflection (see e.g., FIG. 7A)). Thus, whatever the origin of this 'secondary' effect, it is likely to be the result of changes in the collective SPION response to the environment, rather than an irreversible chemical alteration of the SPION surfaces somehow caused by a pH change. However, the near absence of this effect in the low-field (0.5 T) $R_1^m$ results (see e.g., FIG. 7A inset) suggests that the dipolar contribution to spin-relaxation—and hence, the water accessibility to the surfaces of the SPION cores—is largely unaffected as the pH is increased over the pre-inflection regime.

This study shows that the observed SPION pH-sensitivities are consistent with transient, reversible SPION clustering modulated by an interplay between surface charge density and solution ionic strength.

Example 9

Demonstration of Reversibility of MR Response and Imaging of pH-Modulated SPION Clustering The following example describes studies that determined that the pH-modulated clustering was reversible.

Figure 9:
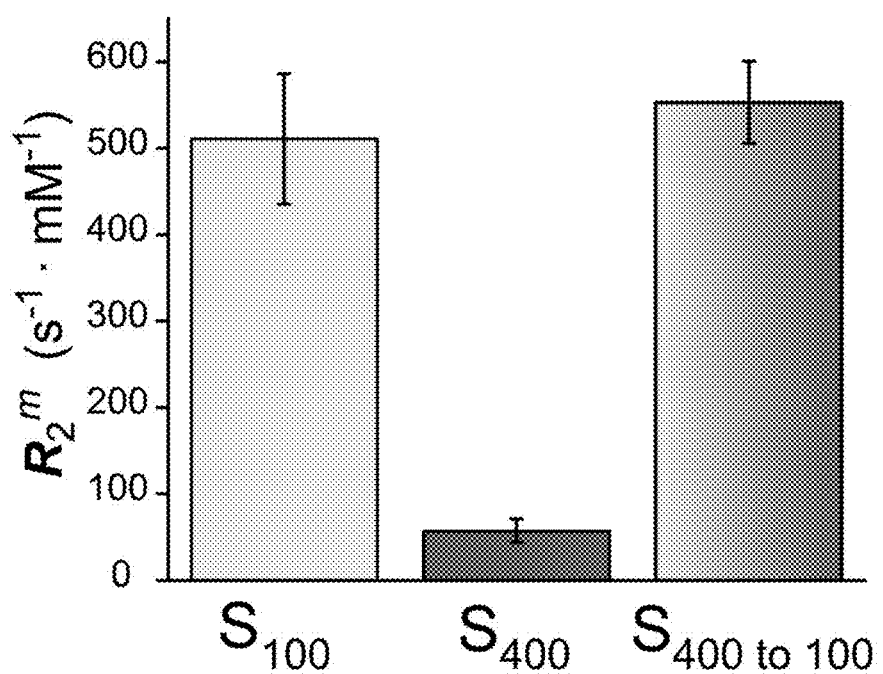
FIG. 9 is a series of bar graphs depicting the reversibility of the MR response to changes in solution ionic strength. $R_2^m$ relaxivities were obtained by fitting $R_2$ values measured from G3-SPION/gelatin suspensions with 100 mM ('$S_{100}$') and 400 mM ('$S_{400}$') [NaCl], compared to the corresponding $R_2^m$ value obtained from samples where the NaCl concentration was changed from 400 to 100 mM ('$S_{400\ to\ 100}$').

A series of experiments were performed to probe the reversibility of the "environment-sensing" MR responses. For experimental simplicity, these experiments were performed using changes in ionic strength. FIG. 9 shows $R_2^m$ measurements obtained (at 7 T, 15° C.) from a series of 400 mM and 100 mM NaCl aqueous gelatin phantoms containing varying amounts of G3-SPIONs-along with a corresponding measurement from a series of samples that were first placed in a 400 mM salt environment for 10 minutes, diluted with DI water until the salt concentration of the samples was 100 mM, allowed to equilibrate in the low-salt environment, and sonicated for 30 seconds before being loaded into gelatin phantoms. SPIONs exposed to high ionic strength conditions—where MR (e.g., $R_2^m$) results consistent with greater clustering are observed—followed by dilution to lower ionic strengths (where reduced clustering would otherwise be expected)—give MR responses similar to those observed under low-clustering/low ionic-strength conditions. These results are consistent with transient, reversible dendron-SPION clustering under the above conditions and further support the conclusion that the high, generation-dependent sensitivity of the SPIONs to their environment is not likely the result of irreversible chemical modification of the surfaces or irreversible clustering.

Figure 10:
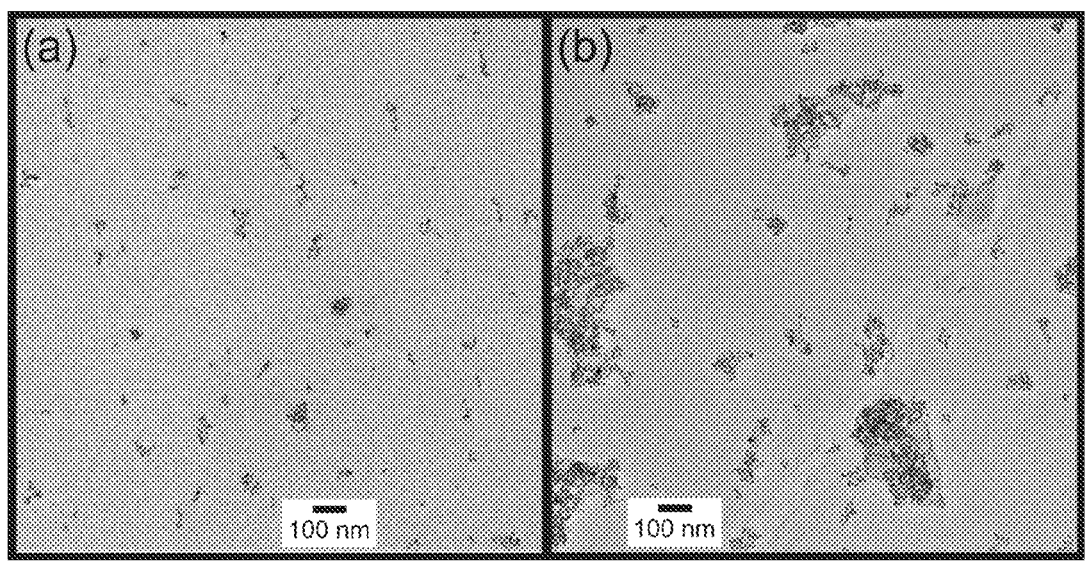
FIG. 10 is a series of TEM images at different pH strengths depicting clustering at high pH.

For further support of the clustering model, TEM images were recently obtained that confirm differential clustering behavior in different pH regimes. FIG. 10A and FIG. 10B respectively show TEM images obtained with G3-SPIONs prepared in solutions with low pH (~3) and high pH (~8). While the sample preparation required (here, solution deposition onto plasma-treated TEM plates followed by evaporation) is inherently a step removed from the ambient aqueous conditions relevant to the MR results, the images are consistent with qualitative expectations: small SPION clusters at observed at low pH, but considerable clustering is observed at higher pH—with a wide distribution of cluster sizes appearing in the high-pH micrograph.

Further support of the clustering model was evidenced by the CPMG echo-time dependence of apparent $T_2$ relaxation induced by various SPIONs, that is consistent with a model[49,50] that assumes that the scale of local magnetic inhomogeneities[51-55]—i.e., originating from transient SPION clustering—is governed by variations in solution conditions. Once refined (e.g., with quantitative comparison with dynamic light scattering, DLS), this model may allow determination of cluster size distributions in situ, as well as give rise to another technique for generating contrast or mapping local pH variations.

This study shows that the observed SPION pH-sensitivities are consistent with transient, reversible SPION clustering modulated by an interplay between surface charge density and solution ionic strength.

Example 10

In Vitro Cellular Uptake Studies

The following example describes investigations of cellular uptake, tolerability, and MR response of dendron-SPIONs using HeLa cell cultures.

Figure 11:
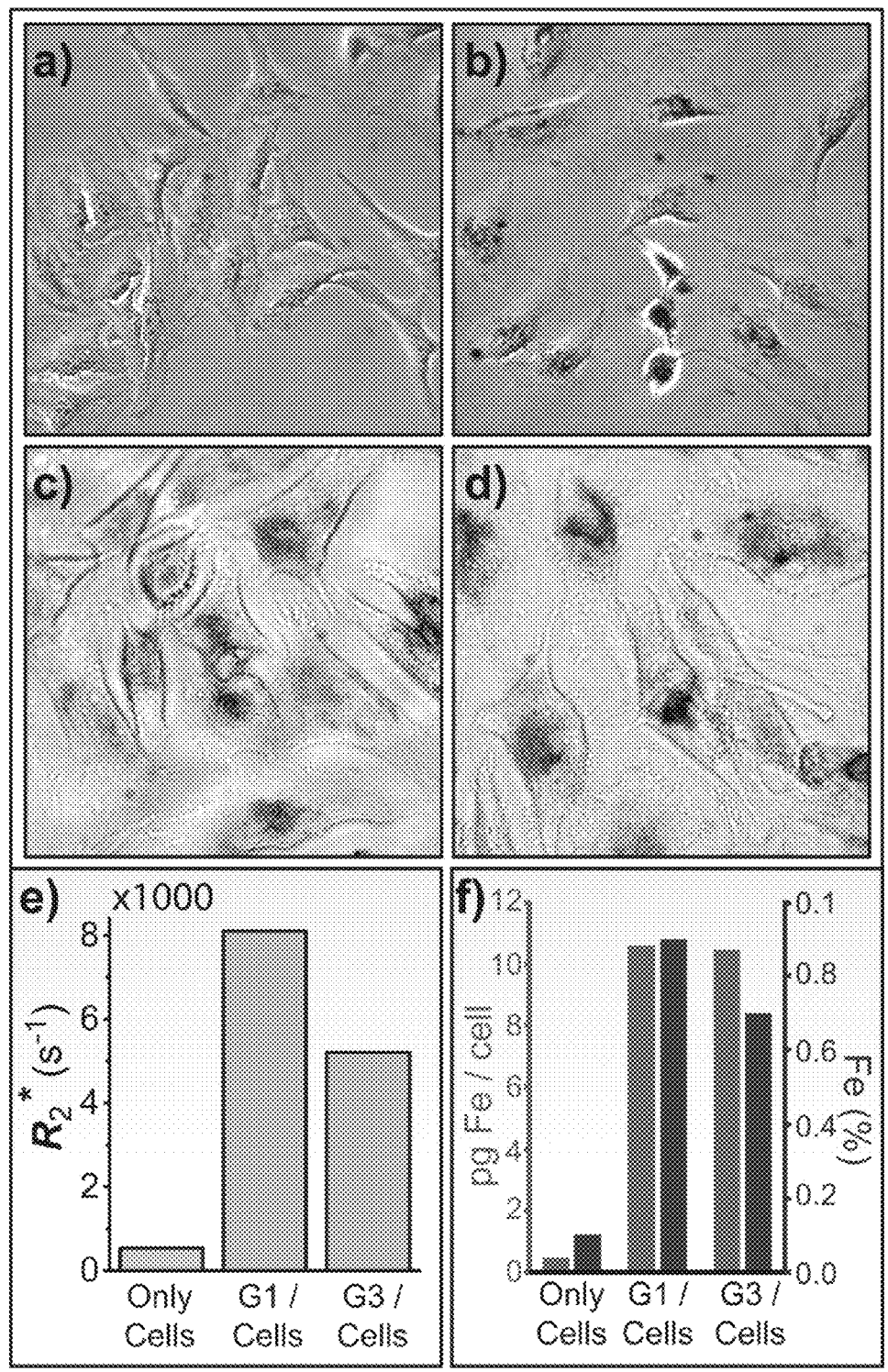
FIG. 11 is a series of optical micrograph images (40×) depicting Prussian Blue-stained HeLa cells indicating the presence of iron and a series of bar graphs depicting relaxivity and iron content in HeLa cells with and without SPIONs.

Because the range of greatest pH sensitivity for these particular SPIONs lies well below that of the cell culture—and these cell cultures were not in living tissues where altered metabolism can lead to variant local pH values—these experiments were not intended to evoke a particular pH-dependent MR response. First, SPION presence had negligible effect on cell growth when compared to control cultures (see e.g., FIG. 3), consistent with high tolerability of the SPIONs for these cells. Furthermore, significant cellular uptake was observed for all three dendron-SPIONs tested, as indicated by Prussian-blue staining/optical microscopy (see e.g., FIG. 11A-D). MR studies at 7 T of G1-/G3-SPION-loaded cell cultures exhibited weak $R_2$ effects (not shown) but very high $R_2^*$ values (see e.g., FIG. 11E), consistent with high cellular uptake but also significant SPION clustering within the cells. Subsequent elemental analysis of the cell plugs indicated significant Fe loading from both the G1- and G3-SPIONs (corresponding to ~11 pg Fe/cell, as shown in FIG. 11F). Higher $R_2^*$ values for HeLa cell plugs incubated with G1-SPIONs vs. G3-SPIONs (~8000 vs. ~5000 s$^{-1}$), while partially explained by the greater cellular density (and hence slightly higher total Fe % in the sample (see e.g., FIG. 11F), also likely indicate greater intracellular clustering of G1-SPION particles vs. G3-SPIONs. Additionally, while these SPIONs exhibited efficient cellular uptake, additional SPIONs can be designed to either suppress or encourage cellular uptake depending on the application (i.e., involving either extracellular or intracellular compartments).

The study shows SPION cellular uptake and MR response in HeLa cell cultures.

Example 11

Effects of pH on MR Behavior of SPIONs with Alternative Surface Functionalities

The following example describes the effects of pH on MR behavior with alternative surface functionalities.

Figure 12:
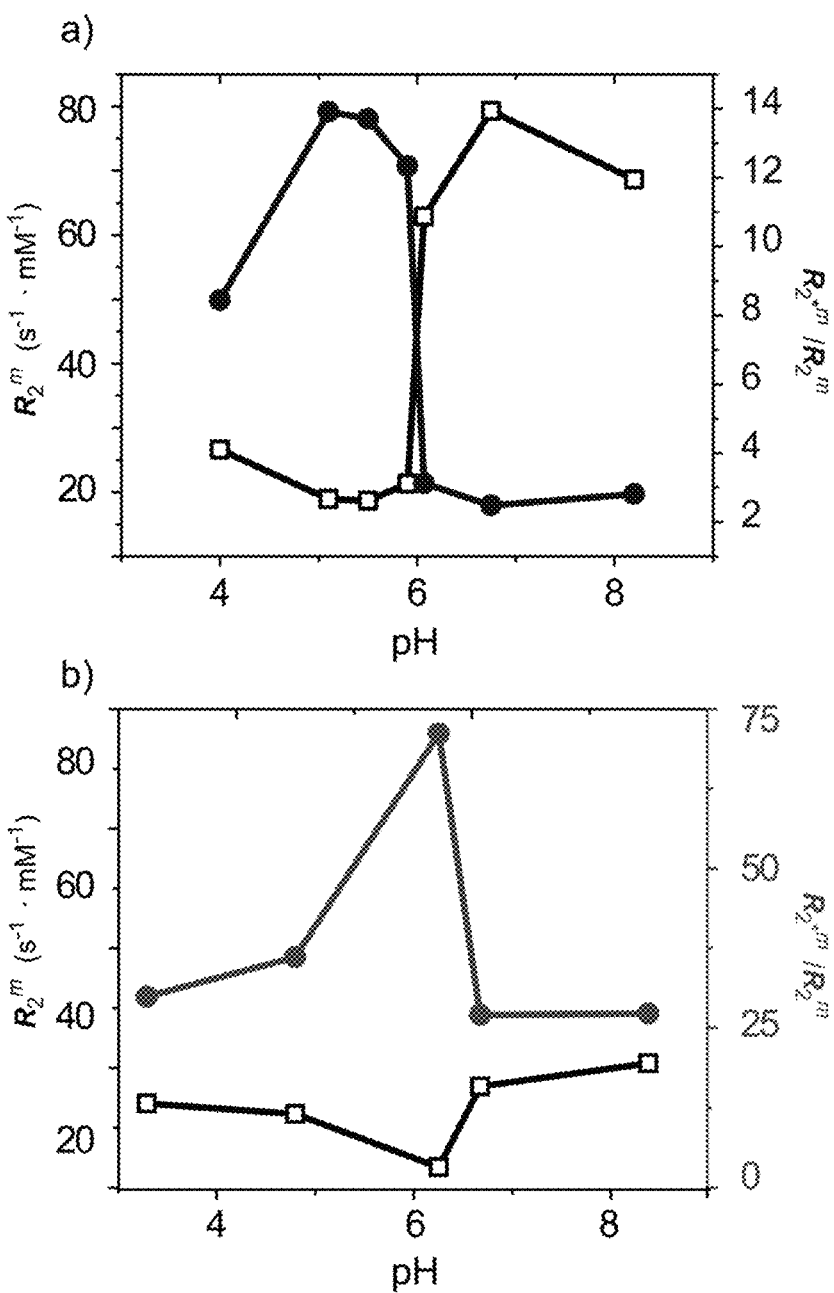
FIG. 12 is a series of graphs depicting relaxivity values of SPIONs as a function of pH concentration.

The melamine-dendron SPIONs exhibit sharply pH-sensitive responses, but not in a range most relevant for most biomedical applications. As a step towards developing SPIONs with pH-sensitive responses in physiologically relevant regimes, SPIONs with different polymer-based surface functionalizations were synthesized—including dopamine-linked nitrilotriacetic-acid-coated SPIONs (C-SPIONs) and polyimidazole (I-SPIONs; see e.g., FIG. 1). Initial examination of these polymer-SPIONs using buffers at physiologically relevant ionic strengths, rather poor relaxivities were obtained. The SPIONs exhibited low sensitivity to pH (data not shown). The experiments were repeated with the buffer ionic strength reduced to 20 mM, the DI-SPIONs showed strong relaxivities and pH sensitivity (see e.g., FIG. 12A): a steep rise in $R_2^m$ relaxivity is observed at pH≥6, with a corresponding reduction in $R_2^{m*}/R_2^m$ ratio (note that imidazole groups usually exhibit a p$K_a$ value of ~6.5)[9]. A similar $R_2^m$ result was obtained at 0.5 T, whereas $R_1^m$ exhibited only a weak pH dependence (data not shown). On the other hand, the C-SPIONs exhibited little useful pH dependence regardless of ionic environment (see e.g., FIG. 12B).

When comparing the I-SPION results with those obtained with the melamine-dendron SPIONs described above, one notices that not only has the point of inflection been moved closer to the desired regime for most physiological applications, qualitatively the trends of $R_2^m$ and the $R_2^{m*}/R_2^m$ ratio are inverted (c.f. FIG. 7). The greater sensitivity to ionic strength for the I-SPIONs (manifested by the greatly reduced range in pH-sensing functionality) may reflect a smaller effective surface loading of the imidazole units compared to the melamine dendron-SPIONs (or, reduced charge-bearing capacity, currently under study). In any case, these results support the possibility of tuning the environmental-dependant MR response—particularly the pH sensitivity—by rational variation of the surface properties.

This study shows that using SPIONs with alternative functionalities demonstrated that the nature of the SPION response to the environment can be highly sensitive to the surface chemical composition; thus, overall our results support the possibility of tuning the SPION pH sensitivity by rational variation of surface properties. Correspondingly, current efforts concern the development and characterization of novel SPIONs that exhibit pH-sensitive MR responses in physiologically relevant regimes while operating in biological (extracellular or intracellular) environments.

Example 12

Synthesis of Imidazole Containing Dendron-Functionalized SPIONs

The following example describes the synthesis of imidazole containing dendron-functionalized SPIONs.

Figure 13:
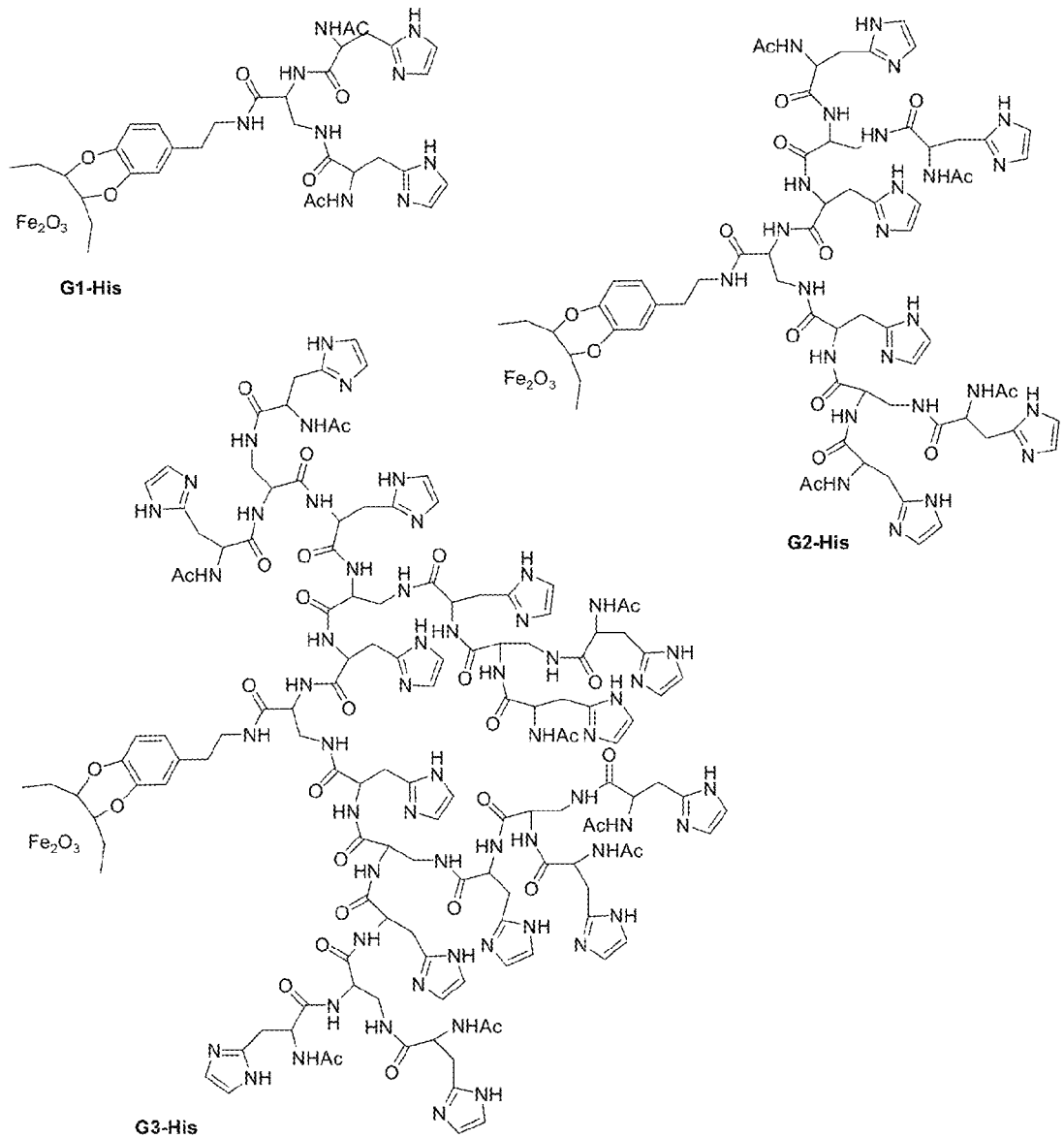
FIG. 13 is a series of chemical structures depicting dendron-SPIONs with different histidine-based structures.

Synthesis is based on the success of the synthesis of the above mentioned DI-SPIONs (see e.g., FIG. 13). Imidazole groups usually exhibit a p$K_a$ value of ~6.5[56]. Correspondingly, dendron-SPIONs with imidazole surface groups should display pH sensitivity near the lower region of the physiologically-relevant pH regime. Variation of the dendron generation number (as well as molar surface loading) should also alter the SPION surface charge density—leading to different degrees of responsiveness to environmental pH, allowing finer control.

Figure 14:
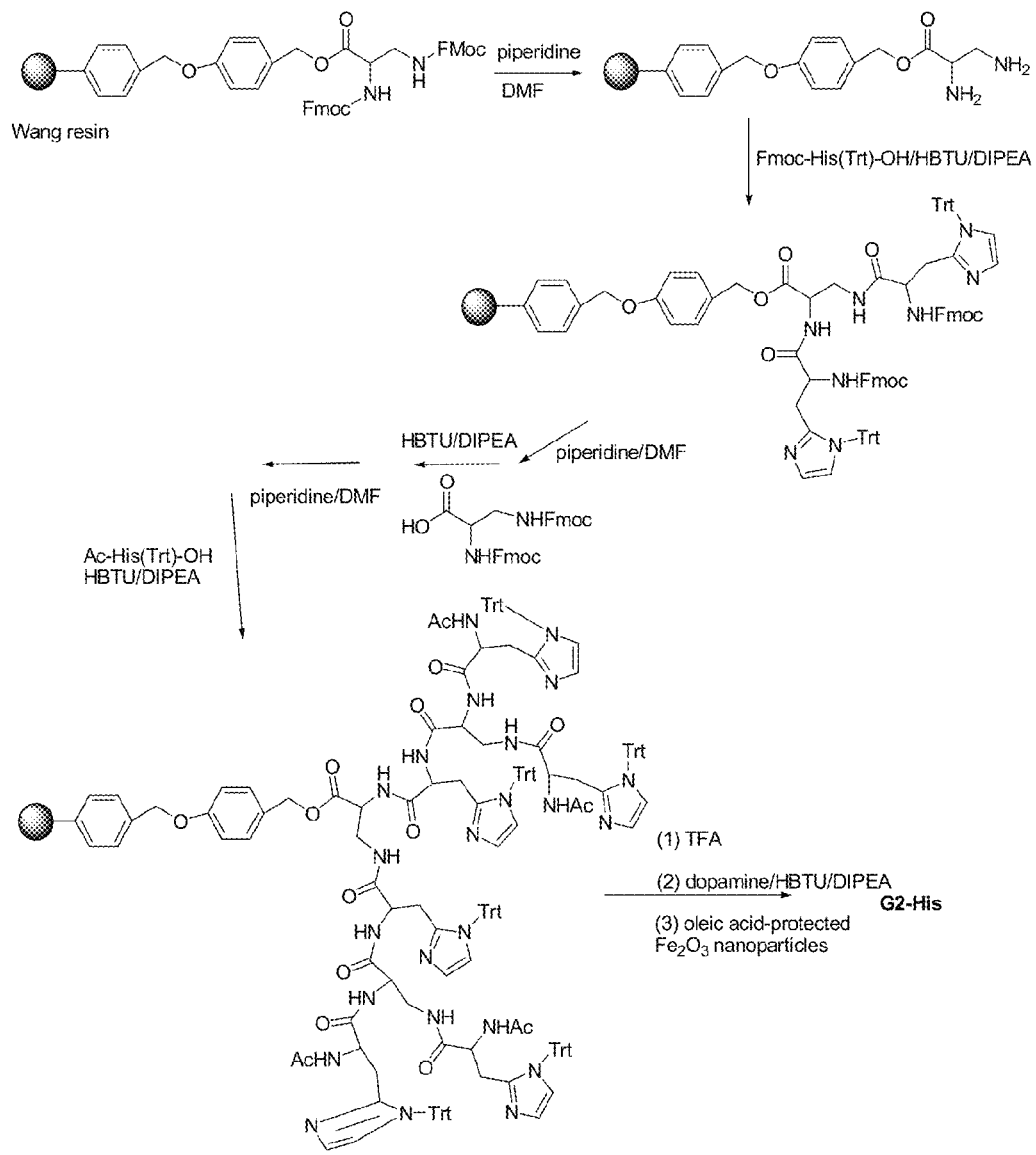
FIG. 14 is a schematic representation depicting a synthetic protocol of G2-His (see e.g., FIG. 13). G1-His and G3-His can be constructed similarly using a solid-phase peptide synthesis strategy.

The synthesis of novel dendron-SPIONs, such as those shown in FIG. 13 are achieved via two major steps (see e.g., FIG. 14): (1) solid phase-supported synthesis of (e.g., imidazole) dendrons; and (2) surface-exchange of the coating materials with the pre-synthesized dendrons to create the dendron-SPIONs. For instance, Fmoc-protected-2,3-diamino-pro-panoic acid is attached to Wang resins. Piperidine is utilized to selectively remove the Fmoc protecting groups that is employed for anchoring two molecules of Fmoc-His (Trt)-OH ligands using HBTU and DIPEA as coupling agents. A similar strategy is applied for introducing more branched imidazole ligands onto the dendron. Piperidine is utilized for de-protecting Fmoc groups and the exposed —NH$_2$ functionalities are employed for introducing a linker, Fmoc-protected-2,3-diamino-propanoic acid. Then, the Fmoc protecting groups on the linker are removed using piperidine. Protected His is introduced again via amide bond formation to give rise to the $2^{nd}$-generation of Histidine dendron. TFA is employed to de-protect Trt groups as well as to remove the dendrons from the polymer resins.

Dopamine is attached to the carboxylate group of the dendron via an amide bond: the dopamine group is a good choice for the linker for attaching the dendrons to the surfaces of the SPIONs because diol ligands have a strong affinity for under-coordinated surface sites of iron oxide nanoparticles[57-60] The resulting dopamine-linked dendrons are then employed in a place-exchange reaction to replace the oleate ligands on the surface of (previously synthesized) SPION cores[61] (~11 nm, <±10%) for the preparation of dendron-SPIONs of a given generation.

While the SPION core synthetic procedure utilized here results in SPIONs passivated with oleic acid ligands (prior to dendron place-exchange), in some recent SPION synthetic protocols the oleic acid was stripped from the SPION surfaces using TMAOH or NaOH (and the dopamine-linked dendrons are added later). Thus, for some experiments this alternative approach was used to test how the dendron loading depends upon SPION surface preparation, as well as to evaluate if surface species (like residual oleic acid molecules) might play a role in modulating the pH-response.

Figure 15:
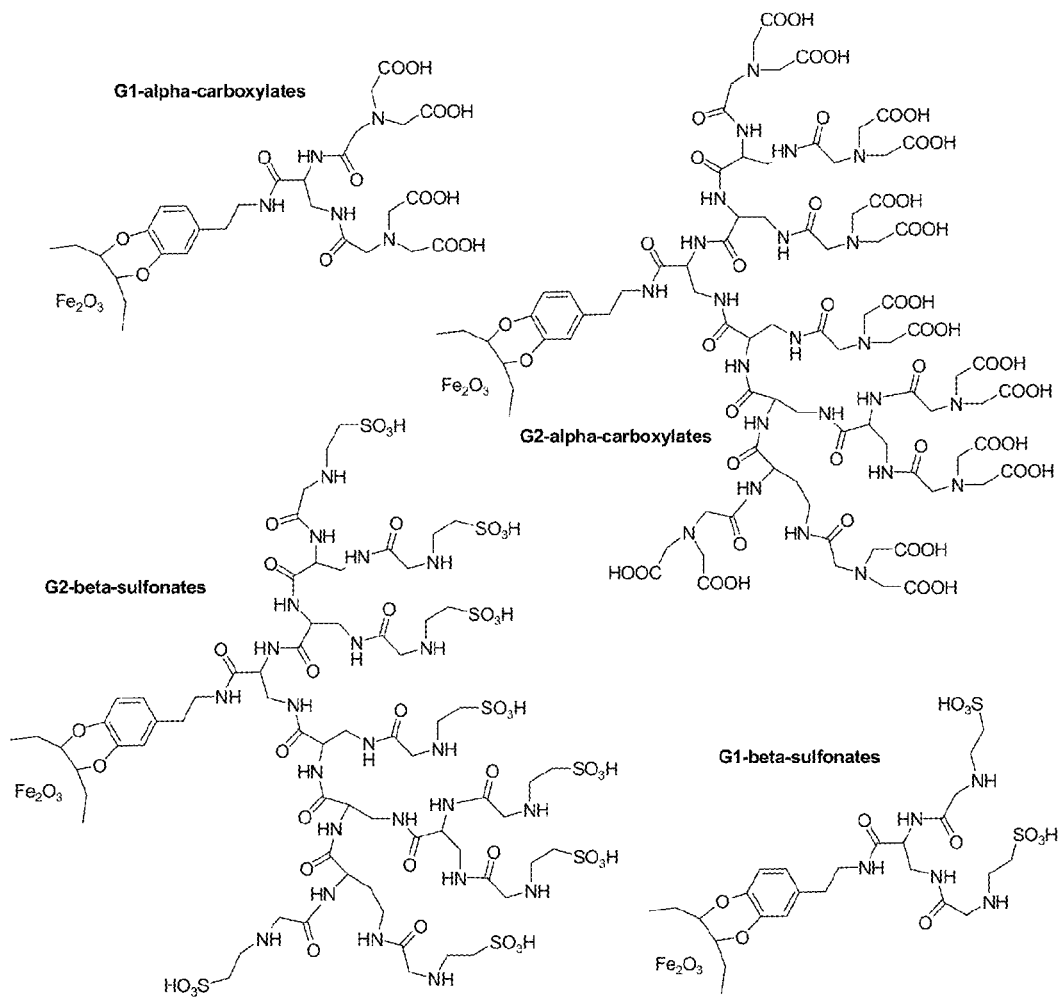
FIG. 15 is a series of chemical structures depicting G1, G2-structures for alternative dendron-functionalized SPIONs. The α-amino-carboxylate and β-amino-sulfonate groups are expected to demonstrate $pK_a$ values of 6.6 and 6.9, respectively.

FIG. 15 shows two other examples of dendritic SPIONs (with α-carboxylate and β-sulfonic acid groups, respectively) that should provide pH sensitivity. It is known that due to the formation of intramolecular hydrogen bonds, the α-carboxylic acid and β-sulfonic acid groups exhibit much higher $pK_a$ values than their conventional counterparts (6.6 and 6.9, respectively). Such SPIONs might not only possess regions of high sensitivity to pH variance within the physiologically-relevant regime (say, >6.5), but—because of the surface anion charges at higher pHs—may also exhibit qualitatively different pH response patterns in the MR data (i.e., compared to those surface-functionalized with positively charged groups).

Figure 16:
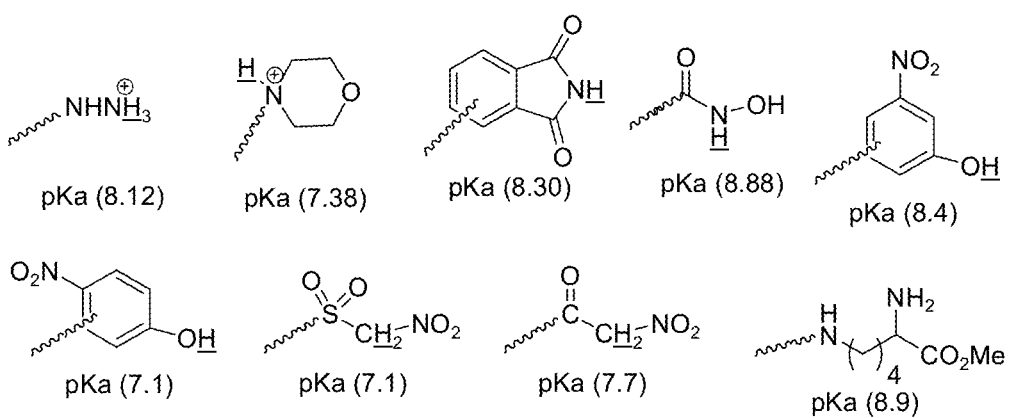
FIG. 16 is a series of selected structures targeted for dendron functionalization with $pK_a$ values between 7.1-8.9.

FIG. 16 shows different fictionalization groups for dendritic SPIONs that are expected to exhibit variances in their MR responses at higher pH values (see e.g., FIG. 16). For example, the α-$NH_2$ group of lysine has a $pK_a$ value of ~8.9.[56] As with others, the synthesis of lysine-based SPIONs can be accomplished via a similar overall strategy to that in FIG. 14. All necessary reagents—including (for example) the side-chain Fmoc-protected lysine methyl ester needed for the alpha-Lys SPIONs—are either commercially available or can be synthesized in a straight-forward manner by following established literature protocols. Characterization of the aforementioned SPIONs can be performed as in the previous Examples.

Example 13

Synthesis of Histidine-Lysine-Dendron-Functionalized SPIONs

The following describes the synthetic procedure for the synthesis of histidine-lysine-dendron-functionalized SPIONs.

Figure 17:
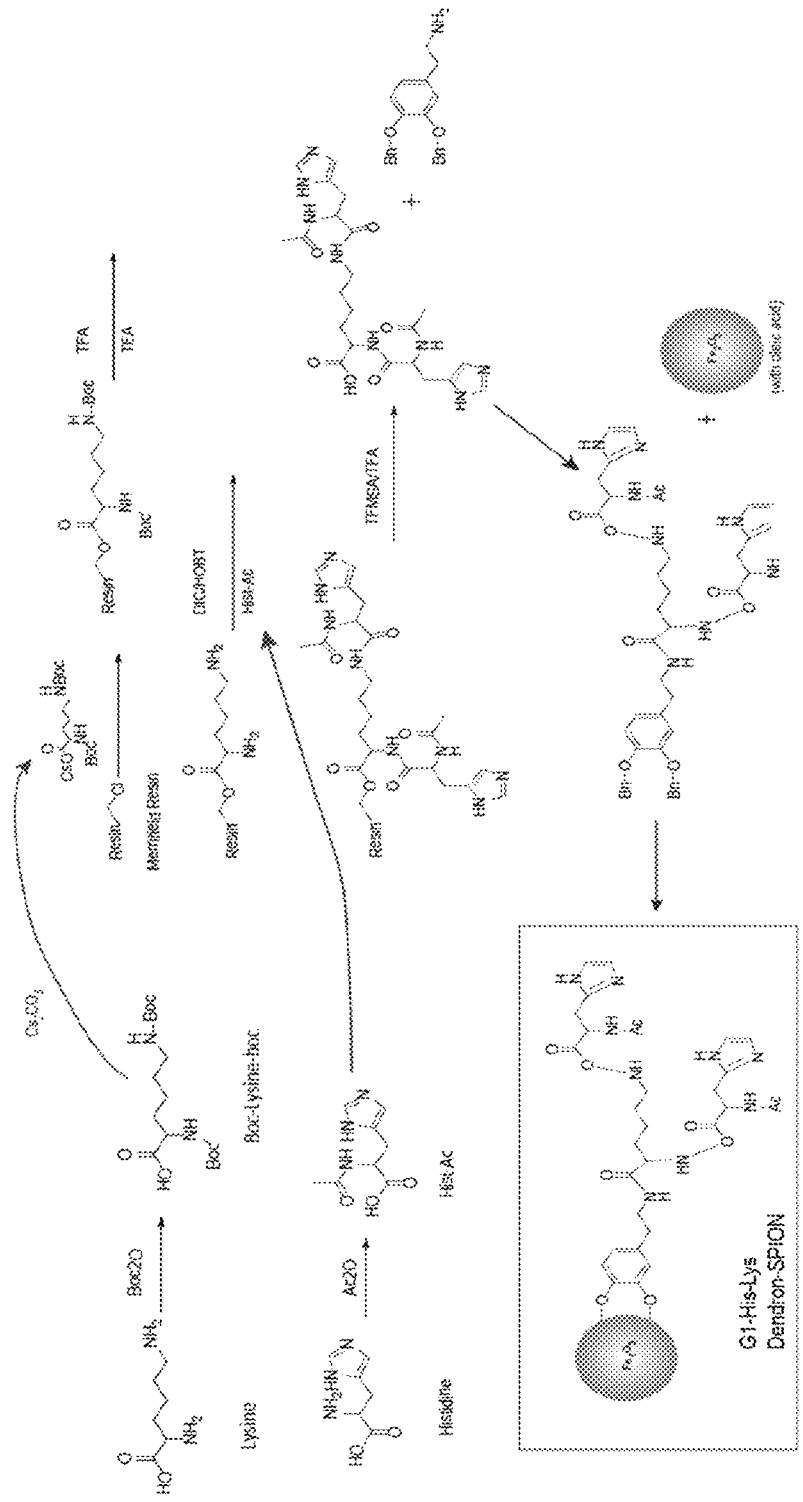
FIG. 17 is a schematic representation depicting a synthetic protocol of Histidine-Lysine-dendron functionalized SPIONs (first-generation dendron, G1).
Figure 18:
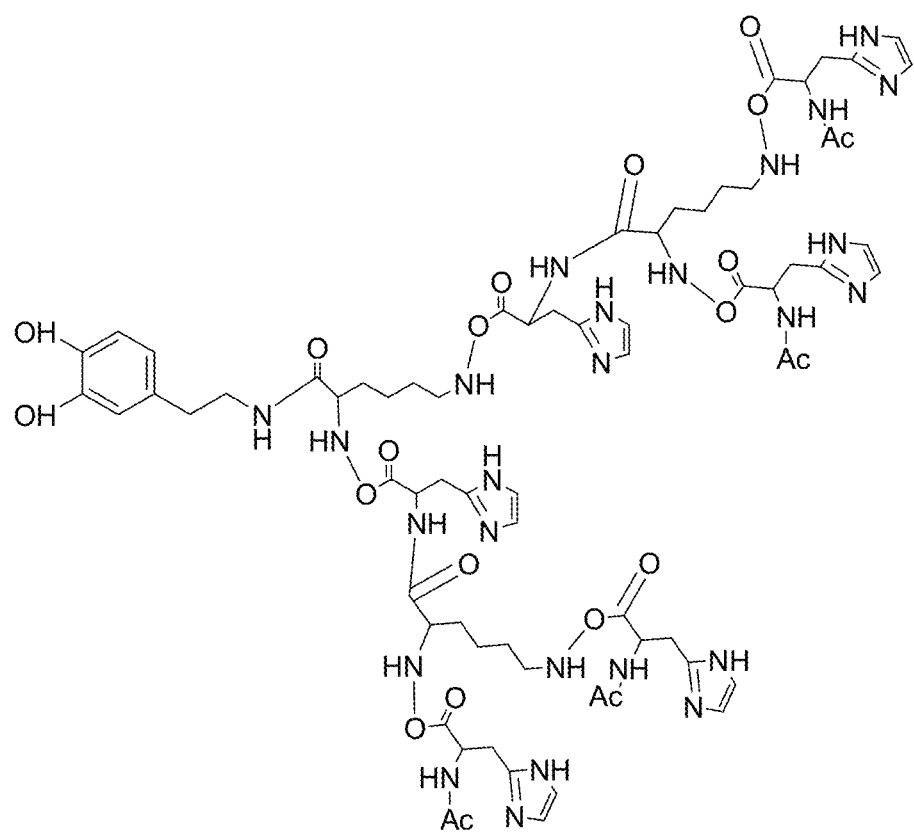
FIG. 18 is a chemical structure of $2^{nd}$-generation histidine-lysine dopamine-linked dendron molecule (G2-His-lys).
Figure 19:
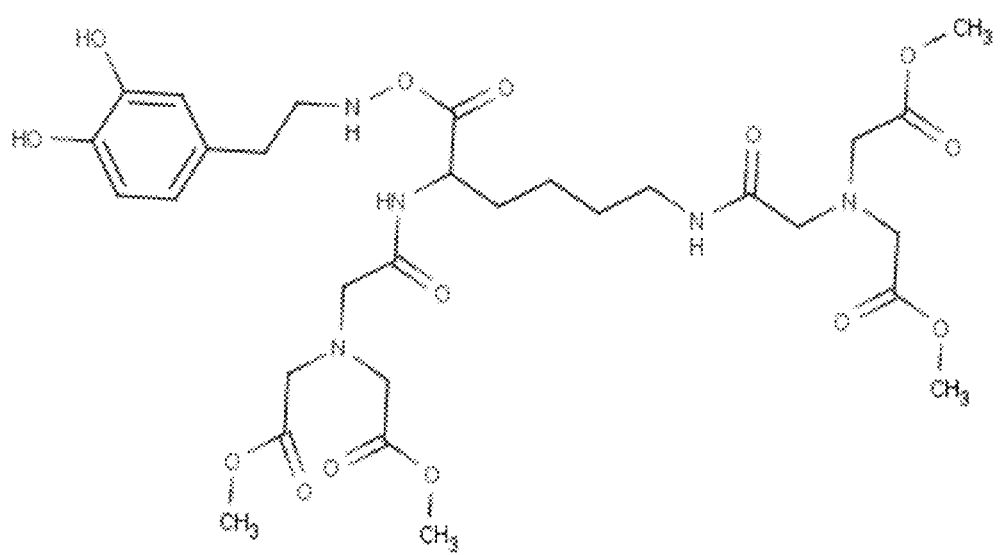
FIG. 19 is first-generation dopamine-linked nitrilotriacetic-acid dendrons (G1-C).
Figure 20:
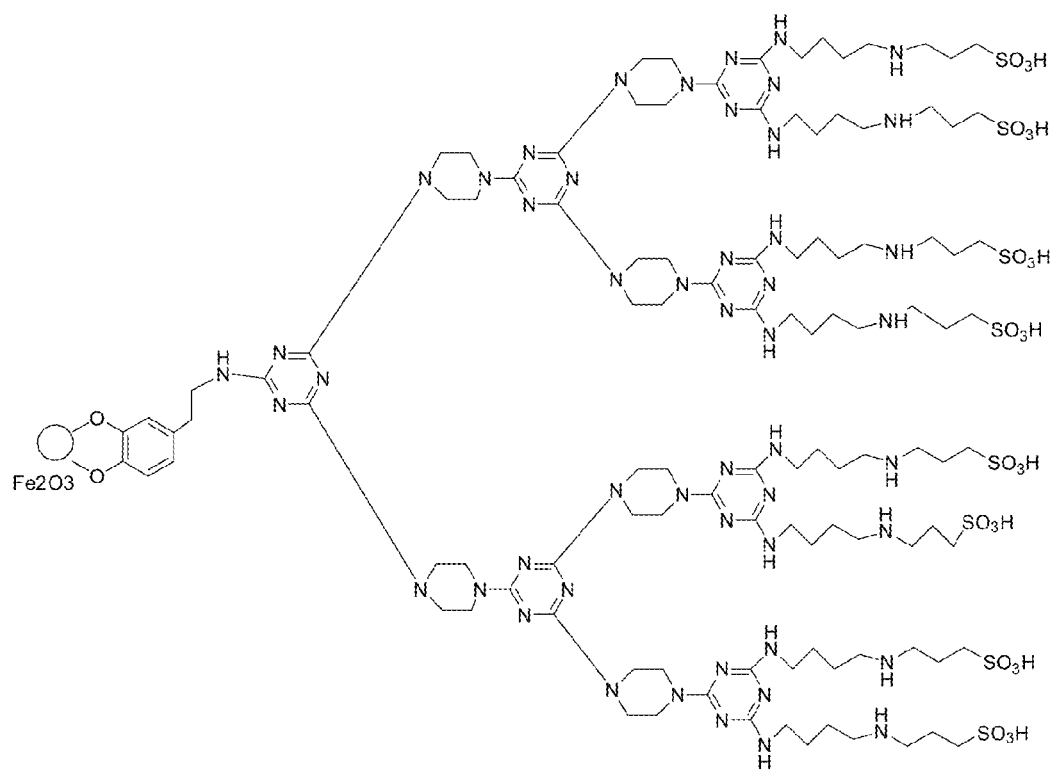
FIG. 20 is a chemical structure of a third generation sulfonate ($Fe_2O_3$-G3-$SO_3H$).
Figure 21:
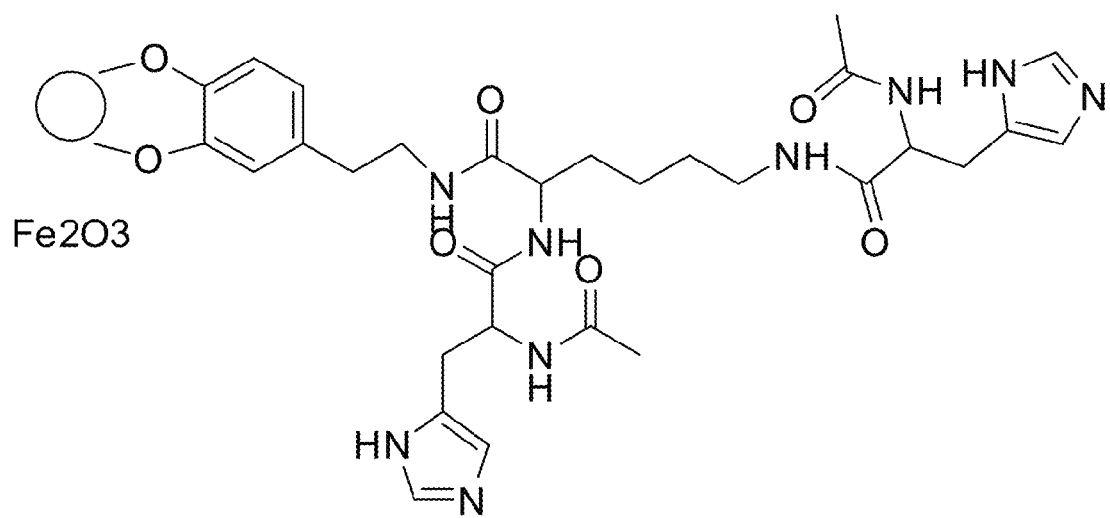
FIG. 21 is a chemical structure of a first generation imidazole dendron ($Fe_2O_3$-imidazole G1 dendron).
Figure 22:
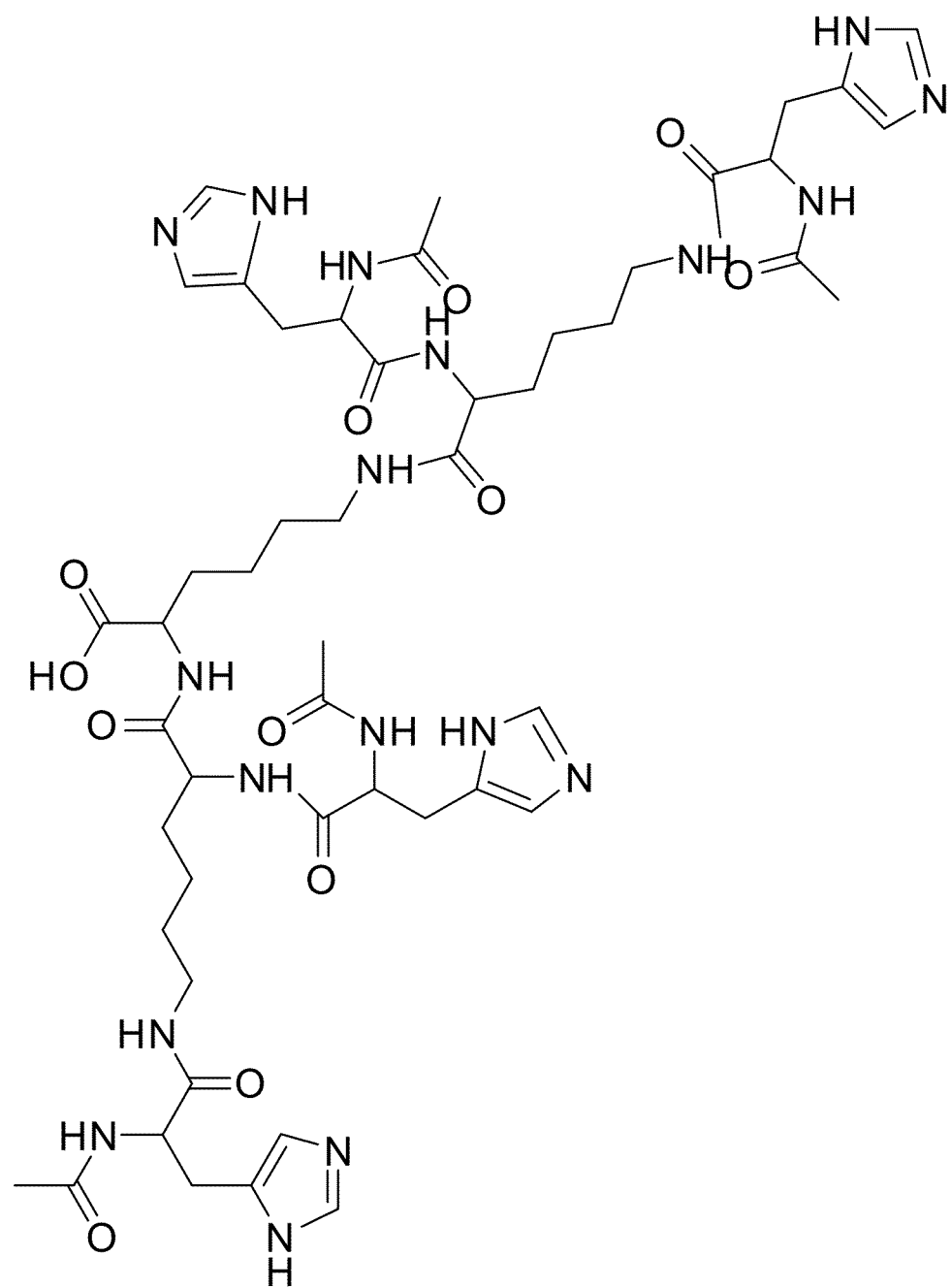
FIG. 22 is a chemical structure of a second generation imidazole dendron (imidazole G2 dendron).
Figure 23:
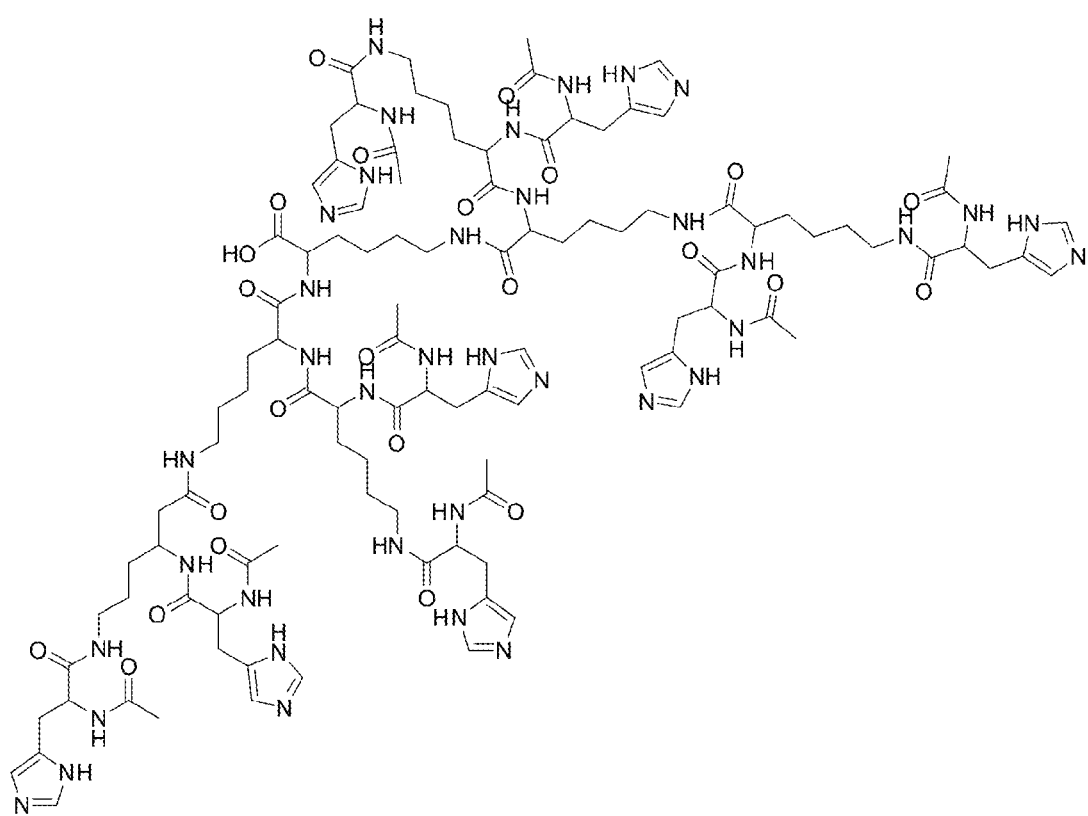
FIG. 23 is a chemical structure of a third generation (imidazole G3 dendron).

FIG. 17 schematically summarizes the various steps for creating Histidine-Lysine-dendron functionalized SPIONs (first-generation dendron, G1), which were successfully synthesized. Lysine and histidine amino acids (chosen because of their free-molecule $pK_a$s) were modified (e.g., with protecting groups). The lysine derivative was then linked to a resin (for solid-phase synthesis) and de-protected, then linked to the histidine derivative. The combined molecule was chemically severed from the resin and a dopamine derivative was covalently attached (the dopamine moiety helps provide strong attachment to the iron-oxide surfaces). In the final steps, the G1-Hys-Lys dendron molecules were attached to oleic-acid-coated SPION cores (e.g. FIG. 1) in methanol under sonication in a ligand-exchange reaction—creating G1-His-Lys dendron-SPIONs (see e.g., FIG. 17 inset). Using related approaches, synthesis of $2^{nd}$-generation histidine-lysine dopamine-linked dendron molecules (G2-His-lys; see e.g., FIG. 18) and first-generation dopamine-linked nitrilotriacetic-acid dendrons (see e.g., FIG. 19) were successful. Characterization of the aforementioned SPIONs can be performed as in the previous Examples.

Example 14

Synthesis of Third Generation Sulfonate-Functionalized SPIONs

The following describes the synthetic procedure for the synthesis of third generation sulfonate-functionalized SPIONs.

The $Fe_2O_3$-G3-$NH_2$ dendron was washed with a pH=10 buffer. The $Fe_2O_3$-G3-$NH_2$ dendron was then washed three times with H2O and then 3 times with methanol. Methanol and Sultone was added and left at 50° C. overnight under Argon. The resulting functionalized SPIONs were collected by a magnet and washed three times with methanol and stored in methanol. Characterization of the aforementioned SPIONs can be performed as in the previous Examples.

Example 15

Imidazole Dendrons

Imidazole G1 dendrons have been synthesized and functionalized onto SPIONs.

Imidazole G2 and G3 dendrons have also been synthesized.

Example 16

Synthesis of Imidazole G1, G2, G3

Imidazole G1-Iron Oxide NP Synthesis

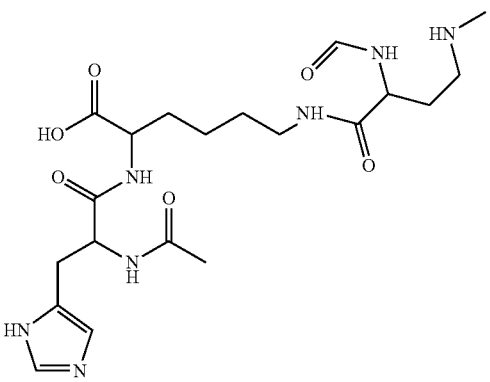 [SMILES: CNCCC(NC=O)C(=O)NCCCCC(NC(=O)C(Cc1cnc[nH]1)NC(C)=O)C(=O)O]

Synthesis of Boc-lysine-Boc

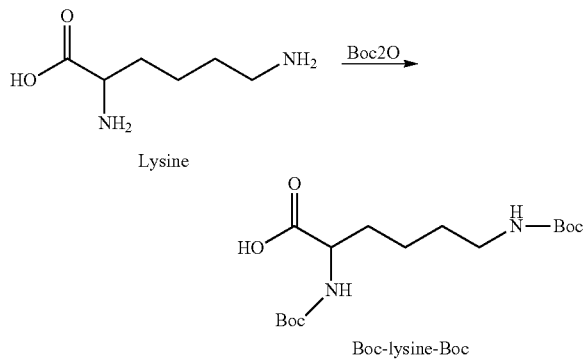

Boc-lysine-Boc

To the solution of Lysine HCl salt in 50 ml 1,4-dioxane/H2O (1:1), 1M NaOH is added until pH reaches 10-11. Then Boc anhydride in dioxane (6.0 g in 20 ml dioxane) is added by an addition funnel. The resulting solution is stirred at room temperature overnight. The mixture is concentrated in vacuo and acidified by 4M KHSO4 until pH=1-2. Extract by Ethyl acetate twice and dried in vacuo. Colorless liquid is obtained and yielding is 100%.

Synthesis of Histidine-acetate

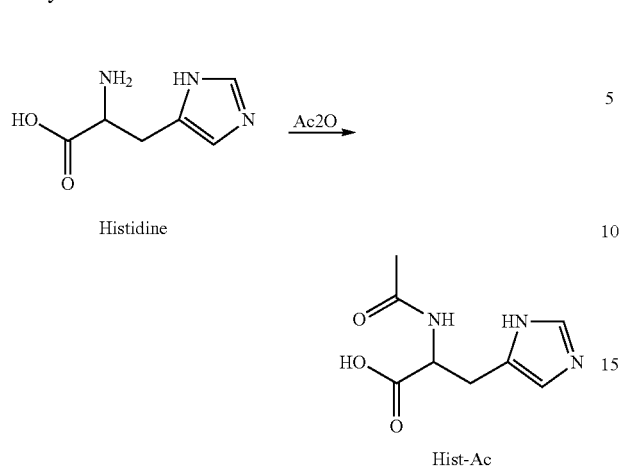

Histidine

Hist-Ac

To a Histidine HCl salt (5.2408 g, 25 mmol) in 20 ml H2O solution, 8M NaOH is added until pH=9-10. Then the temperature is cooled down to 0° C. Acetic andydride (4.72 ml, 50 ml) is dropwise added and pH is maintained at 10 in the same time. After 4 hours reaction the solution pH is adjusted by conc. HCl to 2. All solvents are removed in vacuo. White solid is obtained. Yielding 99%

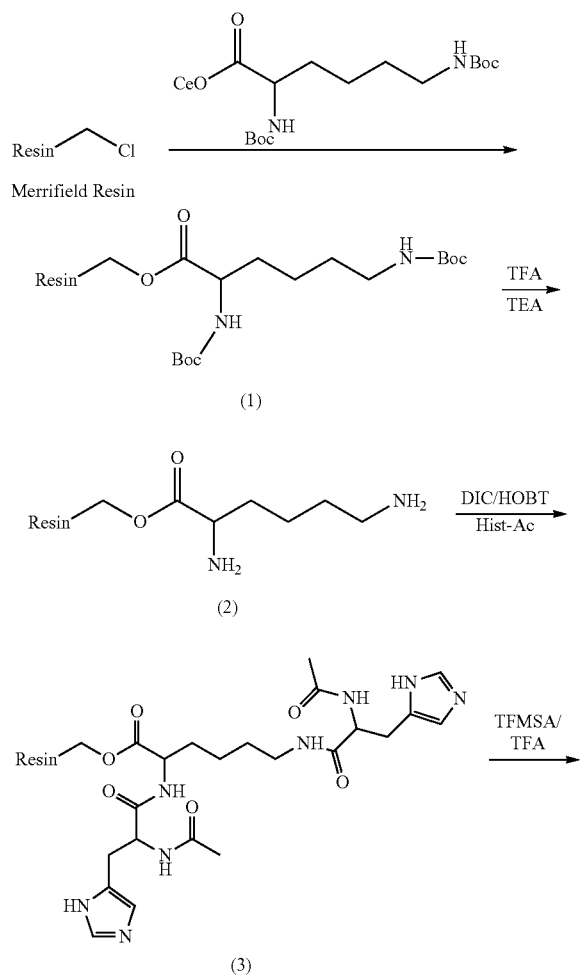

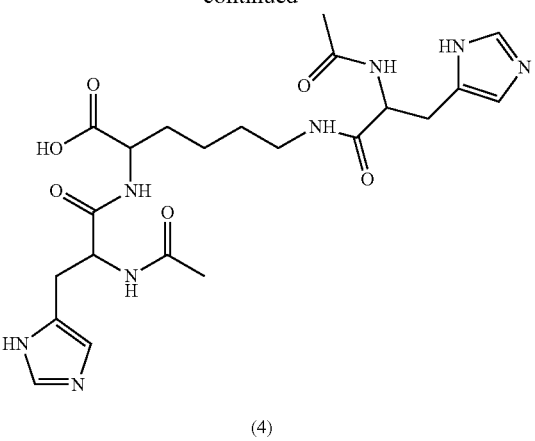

(4)

Synthesis of (1)

Boc-lys-Boc (1.1432 g, 3.3 mmol) is dissolved in 15 ml MeOH and Ce2CO3 aqueous solution (20% wt) is added to adjust pH=7.5. The mixture is stirred for 1 h and dried in vacuo first then in KOH overnight. Boc-lys-boc-Ce salt (White powder) is obtained.

Merrifield resin (Cl substitution 3.2 mmol/g, 825 mg, 2.64 mmol) is soaked in 6 ml DMF for 30 mins. 8 ml DMF is added to dissolve the previous Boc-lys-boc-Ce salt then the solution is transferred to the merrifield resin solution and stirred overnight at 50° C. The resin is washed by DMF, H2O, MeOH and CH2Cl2 and dried in vacuo overnight. 1.2327 g Boc-lys-Boc Merrifield resin is obtained. (407.7 mg, 1.18 mmol Boc-lys-Boc is grafted on the resin and for 1 g resin boc-lys-boc substitution is 0.95 mmol/g resin)

Synthesis of (2)

1.2327 g, 1.18 mmol Boc-lys-boc substituted resin (1) is added in to 8 ml TFA/dichloromethane (1:1 by volume) and stirred for 25 mins at room temperature. Then resin is washed by dichloromethane, MeOH and dichloromethane and dried in vacuo.

To the resin (1.18 mmol) 10 ml Triethylamine/dichloromethane solution (1:10 volume/volume) is added and stirred for 20 mins at room temperature. Resin(2) is washed by isopropanol and dichloromethane and dried overnight.

Synthesis of (3)

To the Histidine acetate (1.862 g, 9.44 mol) in 15 ml anhydrous DMF solution 1.446 g HOBT (Hydroxybenzotriazole) and 1.010 g DIC (diisopropylcarbodiimide) are added and stirred for 30 mins under Ar. The resulting solution is transferred to (2) resin and stirred at room temperature under Ar for 24 hours. Resin is washed by DMF and dichloromethane.

Synthesis of (4)

200 mg (3) resin is stirred for 10 mins in 20 ml TFA (trifluoroacetic acid) in ice bath and 342 mg TFMSA (Trifluoromethanesulfonic acid) is added and the resulting mixture is stirred for another 3 hours. The mixture is filtered and the filtrate is collected and concentrated in vacuo to remove most TFA. The product 4 is precipitated in 50 ml cold ether and washed by ether. 22 mg (4) is obtained as white solid.

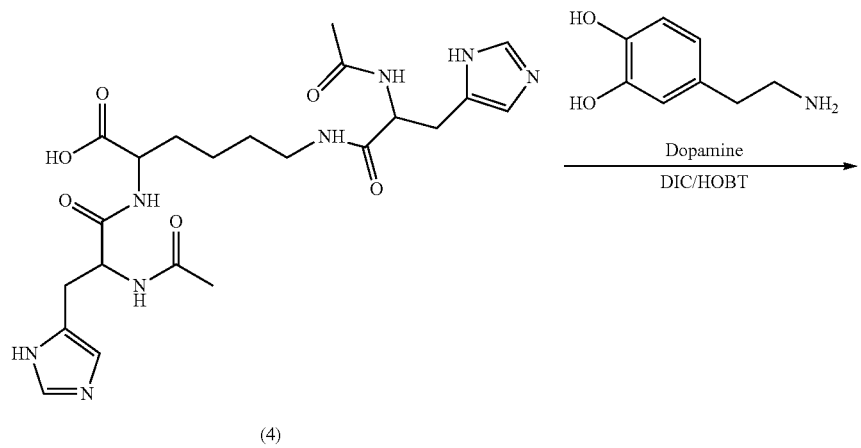

(4)

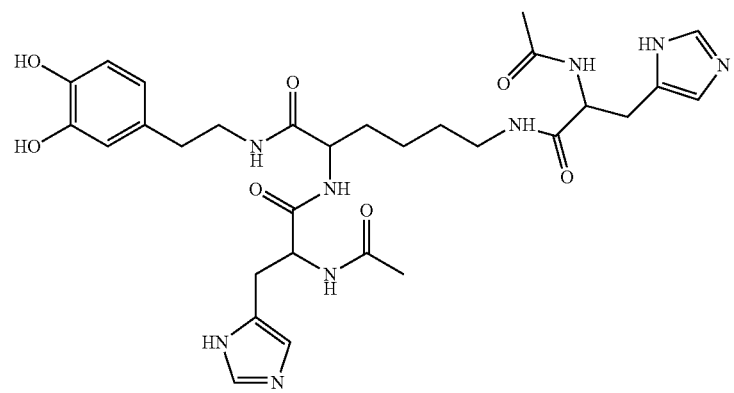

(5)

Dopamine HCl salt (23.5 mg, 0.124 mmol), (4) (100 mg (Plus acids), 0.124 mmol), diisopropylcarbodiimide, (15.65 mg, 0.124 mmol) are added into 1.5 ml DMF. Ar Purge for 30 mins. Then K2CO3 (68.55 mg, 0.496 mmol) is added. The mixture is stirred at room temperature for 14 hour sunder Ar. 1 ml H2O is added then all solvents are removed in vacuo and washed by Et2O ×2 and CHCl3 ×2. Remove all solvents and 40 mg product is obtained.

Exchange of (5) and Iron Oxide Nanoparticles

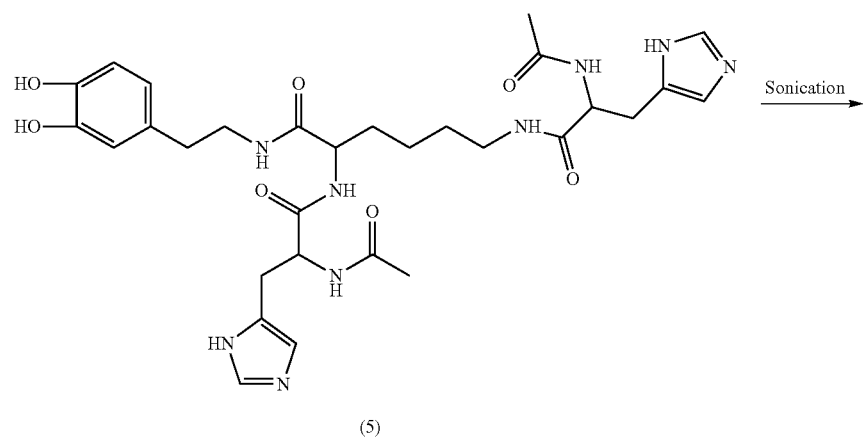

(5)

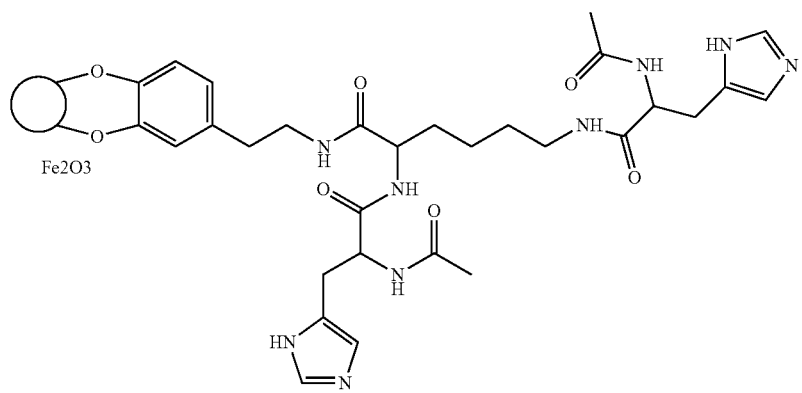
(6)
(5) 77 mg, 0.12 mmol is dissolved in 2.5 ml MeOH and mixed with 2.5 ml iron oxide nanoparticles (CHCl3, 2 mg/0.05 ml). The resulting mixture is sonicated for 14 hours under Ar. Imidazole G1-iron oxide NP is collected by magnet and washed by chloroform and methanol and kept in MeOH.
Synthesis of Imidazole G2 Dendron
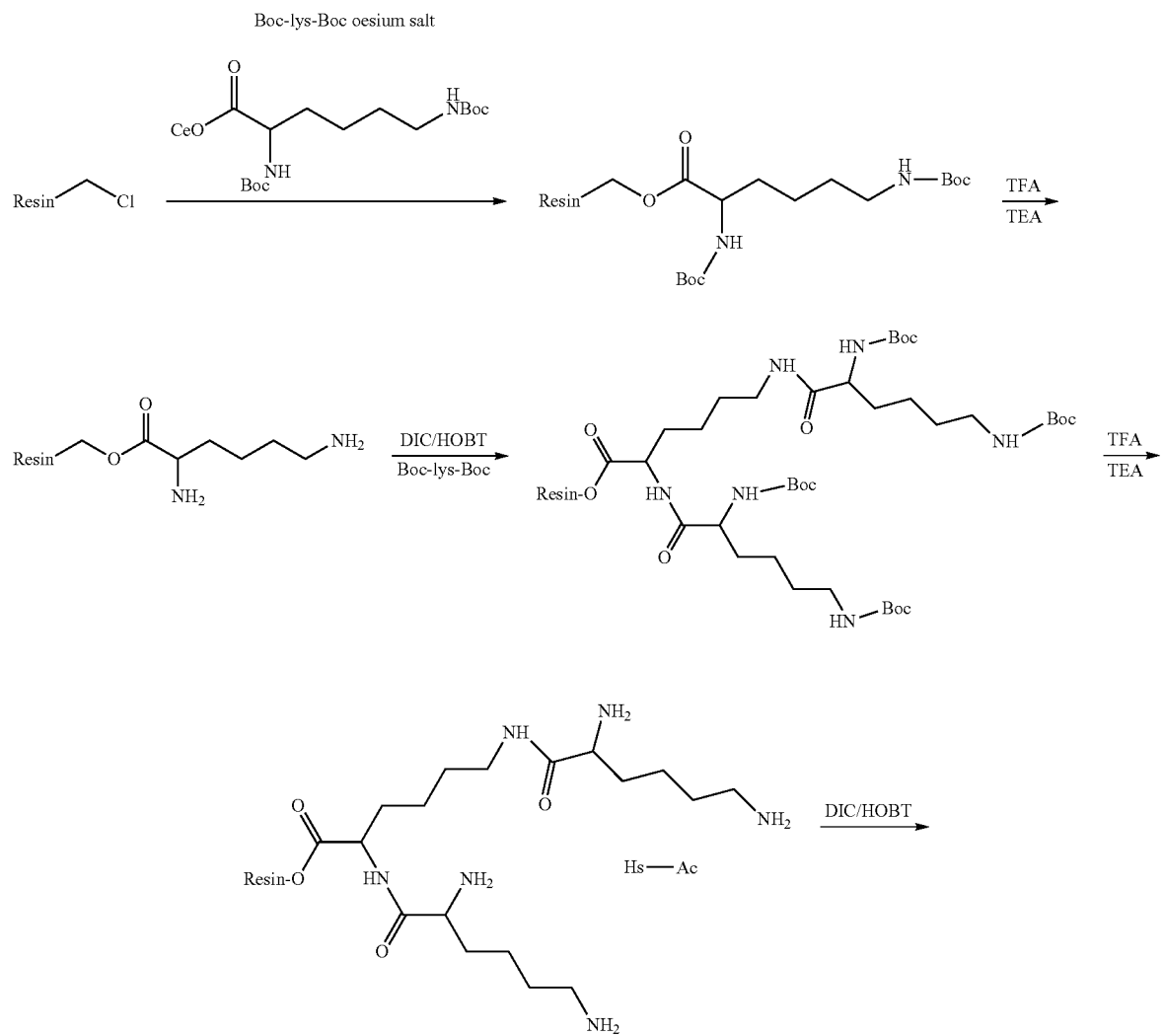

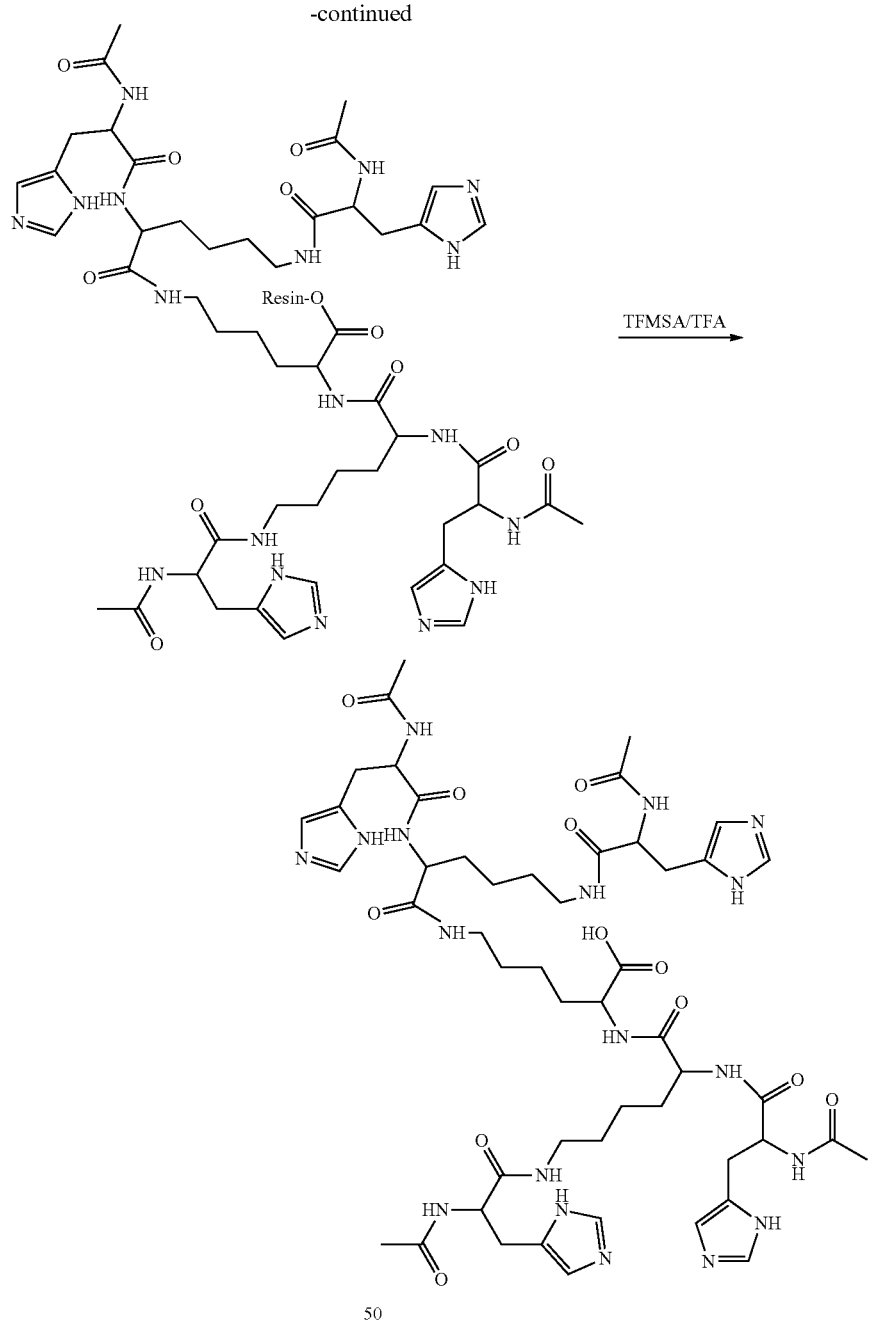
Imidazole G2 synthesis follows the similar route of Imidazole G1. After TFMSA/TFA cleavage 1H-NMR shows a lot of impurities and cannot be separated.
Synthesis of Imidazole G3 Dendron
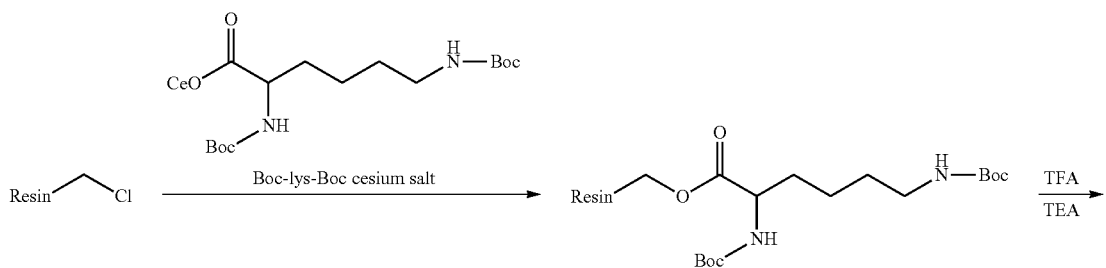

-continued
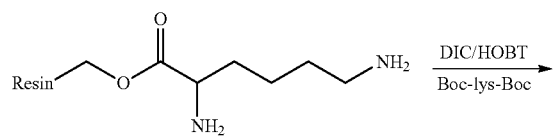
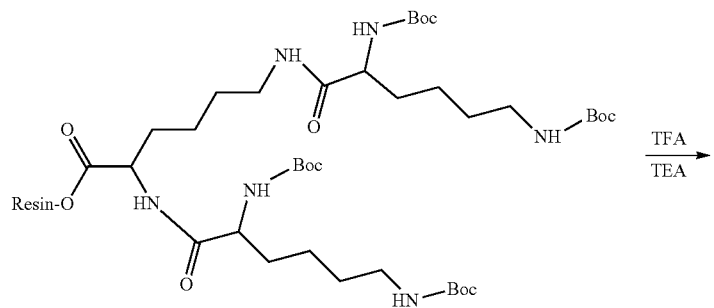
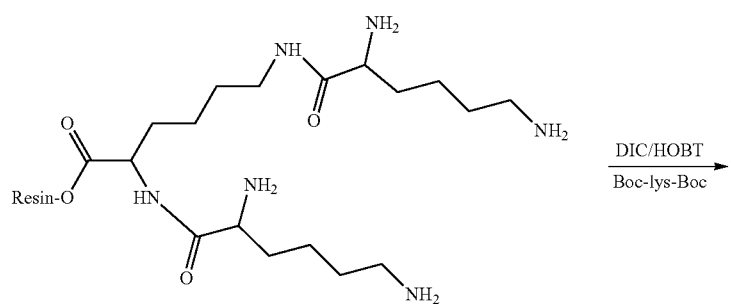
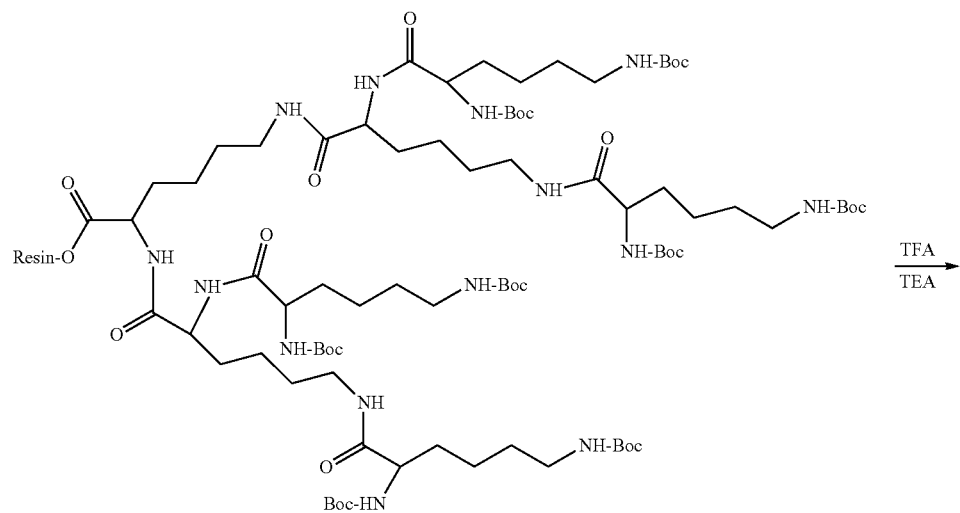

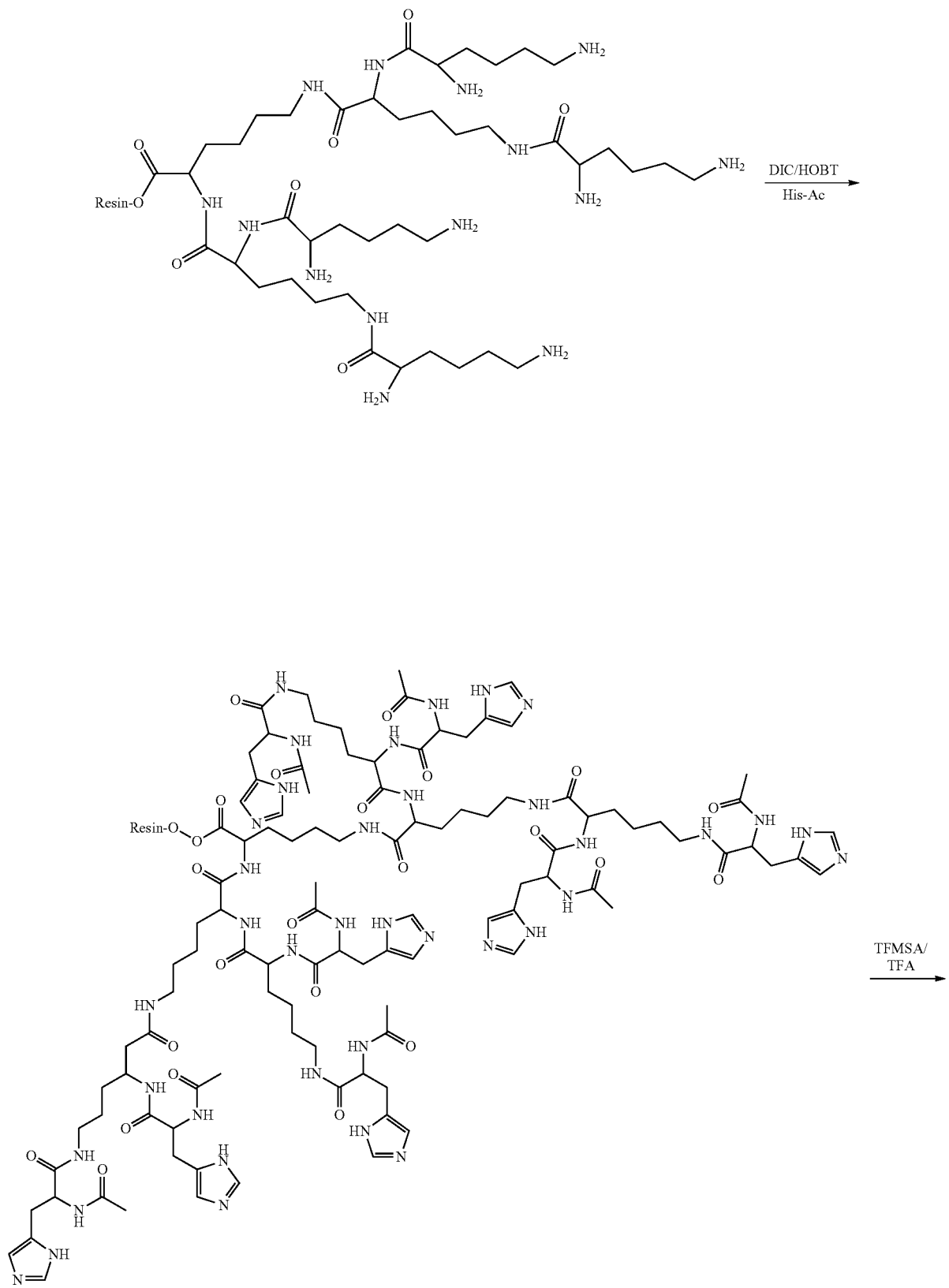

-continued

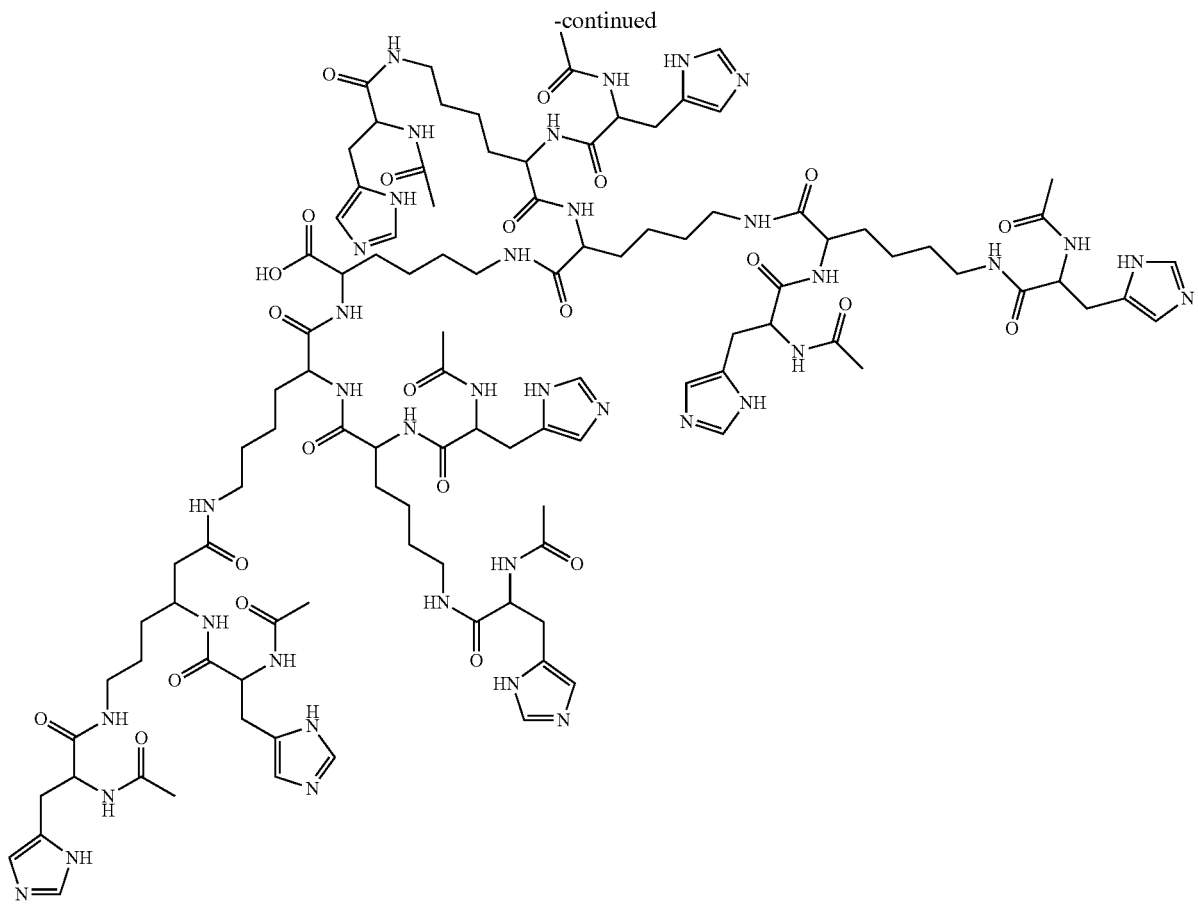

Imidazole G3 synthesis also is similar as Imidazole G1. But after TFMSA/TFA cleavage 1H-NMR shows a lot of impurities and was not separated.

REFERENCES:

(1) Weissleder, R. *Science* 2006, 312, 1168.
(2) Vaupel, P.; Rallinowski, F.; Okunieff, P. *Cancer Res.* 1989, 49, 6449
(3) Tannock, I. F.; ins, D. H. *Cancer Res.* 1989, 49, 4373
(4) Martin, G. R.; Jain, R. K. *Cancer Res.* 1994, 54, 5670.
(5) Gerweck, L. E.; Seetharaman, K. *Cancer Res.* 1996, 56, 1194.
(6) Carmeliet, P.; Jain, R. K. *Nature* 2000, 407, 249.
(7) Gillies, R. J.; Raghunand, N.; Garcia-Martin, M. L.; Gatenby, R. A. *IEEE Eng. Med. Biol. Mag.* 2004, 23, 57.
(8) Vermathen, P.; Capizzano, A. A.; Maudsley, A. A. *Magn. Reson. Med.* 2000, 43, 665.
(9) Zhou, J.; Payen, J. F.; Wilson, D. A.; Traystman, R. J.; Zijl, P. C. v. *Nature Med.* 2003, 9, 1085.
(10) Stubbs, M.; Bhujwalla, Z. M.; Tozer, G. M.; Rodrigues, L. M.; Maxwell, R. J.; Morgan, R.; Howe, F. A.; Griffiths, J. R. *NMR Biomed.* 1992, 5, 315.
(11) Gillies, R. J.; Z, Z. L.; Bhujwalla, Z. M. *Am. J. Physiol.* 1994, 267, C195.
(12) Ackerman, J. J. H.; Soto, G. E.; Spees, W. M.; Zhu, Z.; Evelhoch, J. L. *Magn. Reson. Med.* 1996, 36, 674.
(13) Soto, E.; Zhu, Z.; Evelhoch, J. L.; Ackerman, J. J. H. *Magn. Reson. Med.* 1996, 36, 698.
(14) Deutsch, C.; Taylor, J. S.; Wilson, D. F. *Proc. Natl. Acad. Sci. USA* 1982, 79, 7944.
(15) Mason, R. P. *Current Medicinal Chem.* 1999, 6, 481.
(16) Cui, W.; Otten, P. Y. J.; Kodibagkar, V.; Mason, R. P. *Proc. Intl. Soc. Magn. Reson. Med.* 2003, 11, 623.
(17) Ward, K. M.; Balaban, R. S. *Magn. Reson. Med.* 2000, 44, 799.
(18) Zhang, S.; Winter, P.; Wu, L.; Sherry, A. D. *J. Am. Chem. Soc.* 2001, 123, 1517.
(19) Aime, S.; Barge, A.; Delli, C. D.; Fedeli, F.; Mortillaro, A.; Nielsen, F. U.; Terreno, E. *Magn. Reson. Med.* 2002, 47, 639.
(20) Liu, G.; Li, Y.; Pagel, M. D. *48th Expl. NMR Conf.* 2007.
(21) Beauregard, D. A.; Parker, D.; Brindle, K. M. *Proc. Intl. Soc. Magn. Reson. Med.* 1998, 6, 53.
(22) Zhang, S.; Wu, K.; Sherry, A. D. *Angew. Chem. Intl. Ed. Engl* 1999, 38, 3192.
(23) Raghunand, N.; Howison, C.; Sherry, A. D.; Zhang, S.; Gillies, R. J. *Magn. Reson. Med.* 2003, 49, 249.
(24) Kalman, F. K.; Woods, M.; Caravan, P.; Jurek, P.; Spiller, M.; Tircso, G.; Kiraly, R.; Brucher, E.; Sherry, A. D. *Inorg. Chem.* 2007, 46, 5260.
(25) Gallagher, F. A.; Kettunen, M. I.; Day, S. E.; Hu, D. E.; Ardenkjaer-Larsen, J. H.; in 't Zandt, R.; Jensen, P. R.; Karlsson, M.; Golman, K.; Lerche, M. H.; Brindle, K. M. *Nature* 2008, 453, 940.
(26) Gallagher, F. A.; Kettunen, M. I.; Brindle, K. M. *NMR Biomed.* 2011.
(27) Hashim, A. I.; Zhang, X.; Wojtkowiak, J. W.; Martinez, G. V.; Gillies, R. J. *NMR Biomed.* 2011.
(28) Weissleder, R.; Elizondo, G.; Wittenberg, J.; Lee, A.; Josephson, L.; Brady, T. *Radiology* 1990, 175, 494.

(29) Bulte, J. W. M.; Douglas, T.; Witwer, B.; Zhang, S.-C.; Strable, E.; Lewis, B. K.; Zywicke, H. A.; Miller, B.; van Gelderen, P.; Moskowitz, B. M.; Duncan, I. D.; Frank, J. A. *Nature Biotechnol.* 2001, 1141

(30) Strable, E.; Bulte, J. W. M.; Moskowitz, B.; Vivekanandan, K.; Allen, M.; Douglas, T. *Chem. Mater.* 2001, 13, 2201.

(31) Kalish, H.; Arbab, A. S.; Miller, B. R.; Lewis, B. K.; Zywicke, H. A.; Bulte, J. W. M.; Jr., L. H. B.; Frank, J. A. *Magn. Reson. Med.* 2003, 50, 275.

(32) Frank, J. A.; Zywicke, H.; Jordan, E. K.; Mitchell, J.; Lewis, B. K.; Miller, B.; Bryant, L. H.; Bulte, J. W. *Acad. Radiol.* 2002, 9, S484.

(33) Frank, J. A.; Miller, B. R.; Arbab, A. S.; Zywicke, H. A.; Jordan, E. K.; Lewis, B. K.; Bryant, L. H.; Bulte, J. W. M. *Radiology* 2003, 228.

(34) Dahnke, H.; Liu, W.; Herzka, D.; Frank, J. A.; Schaeffter, T. *Magn. Reson. Med.* 2008, 60, 595.

(35) Atanasijevic, T.; Shusteff, M.; Fam, P.; Jasanoff, A. *Proc. Natl. Acad. Sci. USA* 2006, 103, 14707.

(36) Perez, J. M.; Josephson, L.; O'Loughlin, T.; Hogemann, D.; Weissleder, R. *Nature Biotech.* 2002, 20, 816.

(37) Perez, J. M.; Simeone, F. J.; Saeki, Y.; Josephson, L.; Weissleder, R. *J. Am. Chem. Soc.* 2003, 125, 10192.

(38) Hirt, R. C.; Schmitt, R. G. *Spectrochim. Act.* 1958, 12, 127.

(39) Lim, J.; Simanek, E. E. *Mol. Pharm.* 2005, 2, 273.

(40) Zhang, W.; Simanek, E. E. *Org. Lett.* 2000, 2, 843.

(41) Duanmu, C.; Saha, I.; Zheng, Y.; Goodson, B. M.; Gao, Y. *Chem. Mater.* 2006, 18, 5973.

(42) Park, J.; An, K.; Hwang, Y.; Park, J.-G.; Noh, H.-J.; Kim, J.-Y.; Park, J.-H.; Hwang, N.-M.; Hyeon, T. *Nature Mater.* 2004, 3, 891.

(43) Venditto, V.; Regino, C.; Brechbiel, M. *Mol. Pharm* 2005, 2, 302.

(44) Kim, M.; Chen, Y.; Liu, Y.; Peng, X. *Adv. Mater.* 2005, 17, 1429.

(45) Gao, X.; Cui, Y.; Levenson, R. M.; Chung, L. W.; Nie, S. *Nature Biotechnol.* 2004, 22, 969.

(46) Lee, H.; Lee, E.; Kim, D. K.; Jang, N. K.; Jeong, Y. Y.; Jon, S. *J. Am. Chem. Soc.* 2006, 128, 7383.

(47) Kievit, F. M., Veiseh, O., Bhattarai, N., Fang, C., Gunn, J. W., Lee, D., Ellenbogen, R. G., Olson, J. M., and Zhang, M. *Adv. Funct. Mater.* 2009, 19, 2244.

(48) LaConte, L. E. W., Nitin, N., Zurkiya, O., Caruntu, D., O'Connor, C. J., Hu, X., and Bau, G. *J. Magn. Reson. Imaging* 2007, 26, 1634.

(49) Saha, I.; He, P.; Stokes, A. M.; Chaffee, K. E.; Zielinski, L. J.; Duanmu, C.; Woods, B. M.; Gao, Y.; Goodson, B. M. to be submitted to *J. Magn. Reson.*

(50) Zielinski, L. J.; Sen, P. N. *J. Magn. Reson.* 2000, 147, 95.

(51) Yablonskiy, D. A.; Haacke, E. M. *Magn. Reson. Med.* 1994, 32, 749.

(52) Jensen, J. H.; Chandra, R. *Magn. Reson. Med.* 2000, 44, 144.

(53) Brooks, R. A.; Moiny, F.; Gillis, P. *Magn. Reson. Med.* 2001, 45, 1014.

(54) Shapiro, M. G.; Atanasijevic, T.; Faas, H.; Westmeyer, G. G.; Jasanoff, A. *Magn. Reson. Imaging* 2006, 24, 449.

(55) Matsumoto, Y.; Jasanoff, A. *Magn. Reson. Imaging* 2008, 26, 994.

(56) J. M. Berg, J. L. Tymoczko, and L. Stryer, *Biochemistry*. (W. H. Freeman, New York, 2001).

(57) N. Kohler, G. E. Fryxell, and M. Zhang, *J. Am. Chem. Soc.* 126, 7206 (2004).

(58) C. Xu, K. Xu, H. Gu, R. Zheng, H. Liu, X. Zhang, Z. Guo, and B. Xu, *J. Am. Chem. Soc.* 126, 9938 (2004).

(59) Y. Yu, Y. Yin, B. T. Mayers, and Y. Xia, *Nano Lett.* 2, 183 (2002).

(60) Y. Wang, J. F. Wong, X. Teng, X. Z. Lin, and H. Yang, *Nano Lett.* 3, 1555 (2003).

(61) J. Park, K. An, Y. Hwang, J.-G. Park, H.-J. Noh, J.-Y. Kim, J.-H. Park, N.-M. Hwang, and T. Hyeon, *Nature Mater.* 3, 891 (2004).

(62) Krause W., Contrast Agents I: Magnetic Resonance Imaging (Topics in Current Chemistry), Pt. 1, Springer, 2002, 249 page.

(63) Reimer et al., Transmission Electron Microscopy, 2008, Springer, 590 pages, Vol. 36.

What is claimed is:

1. A magnetic resonance imaging agent comprising:
   (a) a superparamagnetic core;
   (b) a linker group; and
   (c) a pH sensitive macromolecule comprising a monomer unit comprising a dendron and having a pKa between 6 and 10;
   wherein,
   the linker group is affixed to the superparamagnetic core;
   the pH sensitive macromolecule is attached to the linker group;
   the dendron comprises a melamine, an imidazole, a polyimidazole, a vinyl imidazole, a nitrilotriacetic acid, a polyethylene glycol (PEG), a histidine, a lysine, an amino carboxylate, a histidine-lysine, or an amino sulfonate;
   the imaging agent exhibits a pH sensitive magnetic resonance response; and
   the imaging agent is biocompatible.

2. The agent of claim 1, wherein the dendron comprises a melamine dendron.

3. The agent of claim 1, wherein the superparamagnetic core comprises one or more of iron oxide or iron platinum.

4. The agent of claim 3, wherein the superparamagnetic core comprises iron oxide.

5. The agent of claim 4, wherein the superparamagnetic core comprises an iron oxide nanoparticle.

6. The agent of claim 1, wherein the linker group is a dopamine, carboxylic acid, silane, 2,3-diaminopropanoic acid, ascorbic acid, lysine methyl ester, or aminopropyltrimethoxysilane (APTMS).

7. The agent of claim 1, wherein the imaging agent comprises a hyperpolarized agent.

8. The agent of claim 1, wherein the pH sensitive macromolecule is a first generation dendron, a second generation dendron, or a third generation dendron.

9. The agent of claim 1, wherein the linker group does not comprise a carboxylic acid.

10. The agent of claim 1, wherein the pH sensitive macromolecule causes a transient or reversible pH-dependent magnetic resonance response.

11. The agent of claim 10, wherein the transient or reversible pH-dependent magnetic resonance response occurs on a timescale of milliseconds or less.

12. The agent of claim 1, wherein the pH sensitive macromolecule further comprises:
   an imidazole, a polyimidazole, a vinyl imidazole, a nitrilotriacetic acid, a polyethylene glycol (PEG), a histidine, a lysine, an amino carboxylate, a histidine-lysine, an amino sulfonate;

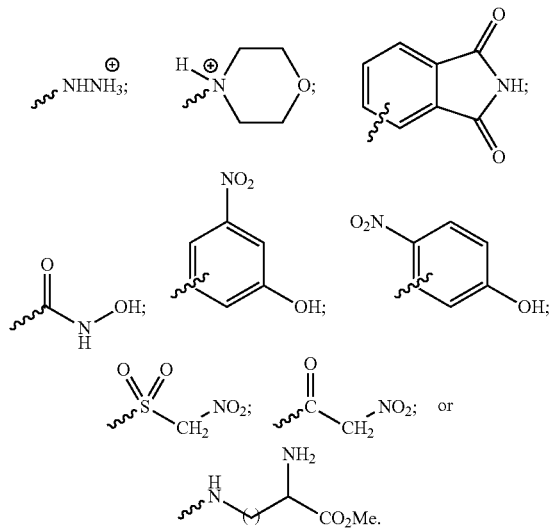

13. A method of imaging a biological tissue comprising:
administering the agent of claim 1 (i) in vivo to a subject comprising a biological tissue or (ii) to an ex vivo biological tissue; and
detecting
  (a) contrast associated with the agent in the biological tissue; or
  (b) contrast associated with pH variations in the biological tissue.

14. The method of claim 13, wherein detecting contrast comprises magnetic resonance imaging.

15. The method of claim 13, wherein detecting contrast comprises identifying changes in a magnetic resonance parameter.

16. The method of claim 15, wherein the magnetic resonance parameter is T1, T2, T2*, D, perfusion, oxygenation, $R_1$, $R_2$, $R_2^*$, $R_2^m$, or $R_2^{m*}$.

17. The method of claim 16, wherein the magnetic resonance parameter is a ratio of $R_2^m$ and $R_2^{m*}$.

18. The method of claim 15, wherein the magnetic resonance parameter is mapped onto a corresponding magnetic resonance image.

19. The method of claim 15, wherein the magnetic resonance parameter is a map or a magnetic resonance image.

20. The method of claim 19, wherein the magnetic resonance image is selected from the group consisting of density-weighted, T1-weighted, T2-weighted, and T2*-weighted magnetic resonance image, or a combination thereof.

21. The method of claim 20, wherein the magnetic resonance image is T2-weighted or T2*-weighted.

* * * * *